(12) United States Patent
Levy et al.

(10) Patent No.: US 9,161,545 B2
(45) Date of Patent: *Oct. 20, 2015

(54) PSEUDOZYMA APHIDIS AS A BIOCONTROL AGENT AGAINST VARIOUS PLANT PATHOGENS

(71) Applicant: Yissum Research Development Company of the Hebrew University of Jerusalem Ltd., Jerusalem (IL)

(72) Inventors: Marganit Levy, Rehovot (IL); Aviva Gafni, Rishon Lezion (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/173,535

(22) Filed: Feb. 5, 2014

(65) Prior Publication Data

US 2014/0141976 A1   May 22, 2014

Related U.S. Application Data

(63) Continuation of application No. 13/700,751, filed as application No. PCT/IL2011/000420 on May 31, 2011, now Pat. No. 8,975,213.

(60) Provisional application No. 61/350,217, filed on Jun. 1, 2010.

(51) Int. Cl.
  A01N 63/04       (2006.01)
(52) U.S. Cl.
  CPC ..................................... A01N 63/04 (2013.01)
(58) Field of Classification Search
  None
  See application file for complete search history.

(56) References Cited

U.S. PATENT DOCUMENTS

2013/0184154 A1   7/2013   Levy et al.

FOREIGN PATENT DOCUMENTS

WO   WO 2004/020647   3/2004
WO   WO 2011/151819   12/2011

OTHER PUBLICATIONS

Allen, T.W., et al. (2004) "Effect of Foliar Disease on the Epiphytic Yeast Communities of Creeping Bentgrass and Tall Fescue," Can. J. Microbiol. 50(10):853-860.
Avis, T.J. and Belanger, R.R. (2001) "Specificity and Mode of Action of the Antifungal Fatty Acid cis-9-Heptadecenoic Acid Produced by Pseudozyma flocculosa," Appl. Environ. Microbiol. 67(2):956-960.
Avis, T.J. and Belanger, R.R. (2002) "Mechanisms and Means of Detection of Biocontrol Activity of Pseudozyma Yeasts Against Plant-Pathogenic Fungi," FEMS Yeast Res 2(1):5-8.
Avis, T.J., et al. (2001) "Molecular and Physiological Analysis of the Powdery Mildew Antagonist Pseudozyma flocculosa and Related Fungi," Phytopathology 91(3):249-254.
Begerow, D. and Bauer, R. (2000) "Phylogenetic Placements of Ustilaginomycetous Anamorphs As Deduced From Nuclear LSU rDNA Sequences," Mycol. Res. 104:53-60.
Boekhout, T. (1995) "Pseudozyma Bandoni emend. Boekhout, A Genus for Yeast-Like Anamorphs of Ustilanginales," J. Gen. Appl. Microbiol. 41:359-366.
Buxdorf, K. et al. (2013) "The Epiphytic Fungus Pseudozyma aphidis Induces Jasmonic Acid- and Salicylic Acid/Nonexpressor of PRI-Independent Local and Systemic Resistance," Plant Pathol. 161:2014-2022.
Dik, A.J., et al. (1998) "Comparison of Three Biological Control Agents Against Cucumber Powdery Mildew (Sphaerotheca fuliginea) In Semi-Commercial-Scale Glasshouse Trials," Eur. J. Plant Pathol. 104(413-423).
Henninger, W. and Windisch, S. (1975) "A New Yeast Sterigmatomyces, S. aphidis sp. n.," Arch. Microbiol. 105:49-50.
International Search Report PCT/IL2011/000420 (2011), pp. 1-4.
Kitamoto, D. et al. (1993) "Surface Active Properties and Antimicrobial Activities of Mannosylerythritol Lipids As Biosurfactants Produced by Candida Antarctica," J. Biotechnol. 29:91-93.
Konishi, M. et al. (2007) "Production of Different Types of Mannosylerythritol Lipids As Biosurfactants by the Newly Isolated Yeast Strains Belonging to the Genus Pseudozyma," Appl. Microbiol. Biotechnol. 75:521-531.
Motita, T. and Konishi, M. (2007) "Physiological Differences in the Formation of the Glycolipid Biosurfactants, Mannosylerythritol Lipids, Between Pseudozyma antarctica and Pseudozyma aphidis," Appl. Microbiol. Biotechnol. 74:307-315.
Paulitz, T.C. and Belanger, R.R. (2001) "Biological Control in Greenhouse Systems," Annu Rev. Phytopathol. 39:103-133.
Rau, U. et al. (2005) "Formation and Analysis of Mannosylerythritol Lipids Secreted By Pseudozyma aphidis," Appl. Microbiol. Biotechnol. 66:551-559.
Rau, U. et al. (2005) "Downstream Processing of Mannosylerythritol Lipids Produced by Pseudozyma aphidis," Eur. J. Lipid Sci. Technol. 107:373-380.
Singh, P. and Cameotra, S.S. "Potential Applications of Microbial Surfactants in Biomedical Sciences," TRENDS Biotechnol. 22(3):142-146.
Spadaro, D. and Gullino, M.L. (2004) "State of the Art and Future Prospects of the Biological Control of Postharvest Fruit Diseases," Intl. J. Food Microbiol. 91:185-194.
Urquhart, E.J. and Punja, Z.K. (2002) "Hydrolytic Enzymes and Antifungal Compounds Produced by Tilletiopsis Species, Phyllosphere Yeasts That Are Antagonists of Powdery Mildew Fungi," Can. J. Microbiol. 48(3):219-229.

Primary Examiner — Alton Pryor
(74) Attorney, Agent, or Firm — AuerbachSchrot LLC; Jeffrey I. Auerbach; William C. Schrot

(57) ABSTRACT

Biocontrol agents are provided, which protect plant and plant material from pests and pathogens, and promote the growth of plants. Also provided are compositions comprising the same, methods for protecting plant and plant material and promoting growth in plants, and uses of said biocontrol agent in the preparation of a pesticidal composition and a growth-promoting composition.

29 Claims, 16 Drawing Sheets

Exp. t. UV (min)

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Primer (LePR1F)

<400> SEQUENCE: 1
tcttgtgagg cccaaaattc        20

<210> SEQ ID NO 2
<211> LENGTH: 20
<212> TYPE: DNA
<213> ORGANISM: Artificial Sequence
<220> FEATURE:
<223> OTHER INFORMATION: Primer (LePR1R)

<400> SEQUENCE: 2
atagtctggc ctctcggaca        20

<210> SEQ ID NO 3
<211> LENGTH: 20
<212> TYPE: DNA
<213> ORGANISM: Artificial Sequence

```
<220> FEATURE:
<223> OTHER INFORMATION: Primer (Le ActineF)

<400> SEQUENCE: 3
aggcacacag gtgttatggt                                                  20

<210> SEQ ID NO 4
<211> LENGTH: 20
<212> TYPE: DNA
<213> ORGANISM: Artificial Sequence
<220> FEATURE:
<223> OTHER INFORMATION: Primer (LeActineR)

<400> SEQUENCE: 4
agcaactcga agctcattgt                                                  20

<210> SEQ ID NO 5
<211> LENGTH: 22
<212> TYPE: DNA
<213> ORGANISM: Artificial Sequence
<220> FEATURE:
<223> OTHER INFORMATION: Primer (ITS forward primer)

<400> SEQUENCE: 5
cttggtcatt tagaggaagt aa                                               22

<210> SEQ ID NO 6
<211> LENGTH: 20
<212> TYPE: DNA
<213> ORGANISM: Artificial Sequence
<220> FEATURE:
<223> OTHER INFORMATION: Primer (ITS reverse primer)

<400> SEQUENCE: 6
tcctccgctt attgatatgc                                                  20

<210> SEQ ID NO 7
<211> LENGTH: 191
<212> TYPE: DNA
<213> ORGANISM: Pseudozyma aphidis L12

<400> SEQUENCE: 7
tttcgatgaa aaccttttt cttgaggtgt ggctcgcacc tgtctaacta aatcgagcta       60 ccacattta acacggttgc atcggttggc tgtcaaacag tgcgcgcggc gatttatttc      120
gcctccccgc gcattgccga gacggtcgac atttaccaaa aacactgttg ataccatagg     180
atttgaacgt a                                                          191

<210> SEQ ID NO 8
<211> LENGTH: 191
<212> TYPE: DNA
<213> ORGANISM: Pseudozyma aphidis

<400> SEQUENCE: 8
tttcgatgaa aaccttttt cttgaggtgt ggctcgcacc tgtctaacta aatcgagcta       60 ccacattta acacggttgc atcggttggc tgtcaaacag tgcgcgcggc gatttatttc      120
gcctccccgc gcattgccga gacggtcgac atttaccaaa aacactgttg ataccatagg     180
atttgaacgt a                                                          191

<210> SEQ ID NO 9
<211> LENGTH: 187
<212> TYPE: DNA
```

<213> ORGANISM: Pseudozyma rogulosa

<400> SEQUENCE: 9

```
tttcgatgaa aacctttttt cttgaggtgt tgctcgcacc tgtctaacta aatcgagcta    60
ccacatttta acacggttgc atcggttggc tgtcaaacag tgcgcgcggc gatttatttc   120
gcccaccgcg ccttgcgaga cggtcgacat ttaccaaaaa cactgttgat accataggat   180
ttgaacg                                                             187
```

<210> SEQ ID NO 10
<211> LENGTH: 189
<212> TYPE: DNA
<213> ORGANISM: Pseudozyma antarctica

<400> SEQUENCE: 10

```
tttcgatgaa aacctttttt cttgaggtgt ggctcgcacc tgtctaacta aatcgagcta    60
ccacatttta acacggttgc atcggttggc tgtcaaacag tgcgcgcggc gaattcattt   120
tcgcccgcgc tctgcgagac ggtcgacact ttaccaaaaa cactgttgat accataggat   180
ttgaacgta                                                           189
```

<210> SEQ ID NO 11
<211> LENGTH: 18
<212> TYPE: DNA
<213> ORGANISM: Artificial Sequence
<220> FEATURE:
<223> OTHER INFORMATION: Primer (LePIN1F)

<400> SEQUENCE: 11

```
cttcttccaa cttcctttt                                                 18
```

<210> SEQ ID NO 12
<211> LENGTH: 18
<212> TYPE: DNA
<213> ORGANISM: Artificial Sequence
<220> FEATURE:
<223> OTHER INFORMATION: Primer (LePIN1R)

<400> SEQUENCE: 12

```
tgttttcctt cgcacatc                                                  18
```

<210> SEQ ID NO 13
<211> LENGTH: 21
<212> TYPE: DNA
<213> ORGANISM: Artificial Sequence
<220> FEATURE:
<223> OTHER INFORMATION: Primer (AtPR1F)

<400> SEQUENCE: 13

```
gcccacaaga ttatctaagg g                                              21
```

<210> SEQ ID NO 14
<211> LENGTH: 22
<212> TYPE: DNA
<213> ORGANISM: Artificial Sequence
<220> FEATURE:
<223> OTHER INFORMATION: Primer (AtPR1R)

<400> SEQUENCE: 14

```
acctcctgca tatgatgctc ct                                             22
```

<210> SEQ ID NO 15
<211> LENGTH: 20
```

```
<212> TYPE: DNA
<213> ORGANISM: Artificial Sequence
<220> FEATURE:
<223> OTHER INFORMATION: Primer (AtPDF1.2F)

<400> SEQUENCE: 15
tcatggctaa gtttgcttcc                                            20

<210> SEQ ID NO 16
<211> LENGTH: 20
<212> TYPE: DNA
<213> ORGANISM: Artificial Sequence
<220> FEATURE:
<223> OTHER INFORMATION: Primer (PDF1.2R)

<400> SEQUENCE: 16
aatacacacg atttagcacc                                            20
```

PSEUDOZYMA APHIDIS AS A BIOCONTROL AGENT AGAINST VARIOUS PLANT PATHOGENS

CROSS-REFERENCE TO RELATED APPLICATIONS

This application claims priority to U.S. patent application Ser. No. 13/700,751 (filed Mar. 8, 2013), PCT/IL2011/000420 (filed May 31, 2011; expired) and 61/350,217 (filed Jun. 1, 2010), each of which applications is herein incorporated by reference in its entirety.

FIELD OF THE INVENTION

The present invention relates to biocontrol agent derived from *Pseudozyma Aphidis* effective against various plant pathogens. More particularly, the invention provides a composition comprising a bactericidal, fungicidal and pesticidal fungal biocontrol agent derived from *P. Aphidis*, which is also useful in enhancing plant growth, vitality and pathogen resistance, and extending the lifespan or shelf-life of produce and other organic products. The invention also relates to methods for accomplishing the same.

BACKGROUND OF THE INVENTION

All publications mentioned throughout this application are fully incorporated herein by reference, including all references cited therein.

Plant pathogens challenge efforts to maximize crop production through their ability to rapidly develop resistance to pesticides, which can result in immense yield losses on an annual basis. One of the main research goals today involves the development of new tools to control pathogens.

Fungal biocontrol agents have become an important alternative to the use of chemicals due to environmental concerns. Biological control can be achieved by one or a combination of mechanisms: antibiosis, mycoparasitism, competition and induced resistance in the host plant. These mechanisms can hinder growth and development of the pathogen, thereby reducing disease. The complex mode of action of biocontrol agents reduces the ability of the pathogens to develop resistance. The development of a biocontrol agent starts with the discovery of antagonists, followed by isolation and characterization of their potential biocontrol activity.

A few biofungicidal products are commercially available in some countries, for example AQ10, which contains conidia of *Ampelomyces quisqualis*, and Sporodex, which is based on conidia of the yeast *Pseudozyma flocculosa*, both used for the control of powdery mildew. There are also some products based on *Trichoderma* spp., such as Throcodex and Thrichopel, which are used against gray mold, root rot and root wilt. However, the use of biological control is still only moderate relative to that of chemical fungicides [Paulitz, T. C. and Belanger, R. R. (2001) Annu Rev. Phytopathol. 39:103-133].

Epiphytic yeasts colonizing different plant surfaces are thought to have biocontrol activity and to provide a natural barrier against some plant pathogens [Avis, T. J. and Belanger, R. R. (2001) Appl. Environ. Microbiol. 67(2):956-960; Urquhart, E. J. and Punja, Z. K. (2002) Can. J. Microbiol. 48(3):219-229]. Biocontrol activity of yeasts and yeast-like fungi has been demonstrated for postharvest diseases [Spadaro, D., and Gullino, M. L. (2004) International Journal of Food Microbiology 91:185-194] and diseases in the greenhouse [Paulitz, T. C. and Belanger, R. R. (2001) Annu Rev. Phytopathol. 39(103-133)]. *Pseudozyma* spp. are a small group of yeast related to the Ustilaginales [Boekhout, T. (1995) General and Applied Microbiology 41(359-366)]. They are mostly epiphytic (derive moisture and nutrients from the air and rain) or saprophytic (grow on and derive their nourishment from dead or decaying organic matter), and they are non-pathogenic to plants and animals [Avis, T. J. and Belanger, R. R. (2002) FEMS Yeast Res 2(1):5-8]. *Pseudozyma rugulosa* and *P. flocculosa* have recently been found to exhibit biological activity against the different powdery mildews with which they are associated [Dik, A. J., et al. (1998) Eur. J. Plant Pathol. 104(413-423]. *P. flocculosa* has been found to secrete an unusual fatty acid that displays antibiotic activity against several pathogens [Avis, T. J. and Belanger, R. R. (2001) Appl Environ Microbiol 67(2):956-960; Avis, T. J., et al., (2001) Phytopathology 91(3):249-254;]. On the other hand, Avis et al. [Avis, T. J., et al., (2001) Phytopathology 91(3):249-254] found no colony collapse of powdery mildew (*Sphaerotheca fuliginea* (Schlechtend.:Fr.) Pollacci) and no production of antifungal fatty acids by *Pseudozyma aphidis* isolated from aphid secretions (isolate CBS 517.83). *P. aphidis* is a close relative of *P. rugulosa* [Begerow, D. and Bauer, R. (2000) Mycol. Res. 104(53-60)], which was first isolated from aphid secretions [Henninger, W. and Windisch, S. (1975) Arch. Microbiol. 105(1):47-48] but has also been found on plant surfaces [Allen, T. W., et al., (2004) Can. J. Microbiol. 50(10):853-860].

The inventors recently isolated the epiphytic yeast *Pseudozyma aphidis* (isolate L12) from strawberry leaves. Isolate L12 was associated with the collapse of powder mildew colonies. Data presented herein demonstrates that L12 secretes extracellular metabolites which inhibit several fungal and bacterial pathogens in vitro. In addition, application of L12 spores on detached tomato leaves or whole tomato plants in the greenhouse significantly reduced *Botrytis cinerea* infection. The inventors therefore further characterize the L12 isolate of *P. aphidis*, developing it as an efficient biocontrol agent against plant pathogens. The conditions needed for mass production of active culture are characterized by testing various temperatures and media and monitoring spore concentration and activity by *B. cinerea* bioassays. The establishment and spread of *P. aphidis* on the host plant using microscopy is assayed. The inventors also assay the secreted fraction of L12 against various pathogens in vitro. In addition, *P. aphidis* L12 spores are applied on tomato plants in the greenhouse and their ability to control fungal and bacterial pathogens in vivo is verified. The new and efficient biocontrol agents provided by the invention may thus contribute to reducing the amount of chemicals required for pathogen control, and as such can genuinely benefit farmers, consumers and the environment.

The inventors herein develop the practical application of *P. aphidis* L12 as a biocontrol agent based on naturally-occurring fungi that increase plant resistance to fungal, viral, bacterial, and insect infestations as well as enhancing growth. The presented results demonstrate the high potential of *P. aphidis* L12 for the control of fungal and bacterial plant pathogens that cause major damage to crop plants. Furthermore, the novelty of the isolate is that it is easy to produce, very stable and effective in low concentration. Chemicals that have traditionally been used to control food plant pathogens are being banned or are no longer effective and organic farmers are not allowed to use them. Other control strategies are either unavailable or impracticable. Driven by environmental concerns and the growing demand for organic products, there is a pressing need for the development of new biological defense strategies.

Thus, one object of the invention is the provision of a composition comprising *Pseudozyma aphidis* cells, components or products, providing improved plant resistance to pathogenic infection. Moreover, the invention further provides compositions for the treatment, amelioration, inhibition or elimination of an established infection or infestation.

Another object of the invention is the provision of a composition comprising *Pseudozyma aphidis* cells, components or products, for the induction of plant immune response.

Yet another object of the invention is the provision of a composition comprising *Pseudozyma aphidis* cells, components or products, for improving plant growth and yield.

These and other objects of the invention will become apparent as the description proceeds.

SUMMARY OF THE INVENTION

The inventors demonstrate here the pesticidal and growth-promoting properties of *Pseudzyma aphidis* and products thereof. Accordingly, various aspects of the invention are considered.

In the first aspect, the invention relates to a pesticidal composition comprising as an active ingredient a biocontrol agent. The composition comprises at least one of:
a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e). The composition optionally further comprises carriers, diluents and excipients.

A second aspect of the invention relates to a composition for conferring resistance in plants against pests infections or infestations. The composition comprises at least one of:
a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e). The composition optionally further comprises carriers, diluents and excipients.

The invention also provides in the third aspect a composition for promoting growth in plant, comprising as an active ingredient a biocontrol agent. The composition comprises at least one of:
a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e); The composition optionally further comprises carriers diluents and excipients.

In addition to providing compositions for protecting plant or plant materials from pests and for promoting growth in plant, the invention also provides methods for accomplishing the same.

Thus, in a further aspect, the invention relates to a method of treating, preventing, ameliorating, inhibiting, eliminating or delaying the onset of bacterial, fungal or pest infestation in a plant or a plant material. The method comprises the step of applying onto a plant, to a plant material or in the vicinity of the plant or plant material a biocontrol agent or a composition comprising the same, wherein the biocontrol agent comprises at least one of:

a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e).

In another aspect, the invention provides a method for promoting growth in plant comprising the step of applying onto a plant, to a plant material or in the vicinity of the plant or plant material a biocontrol agent or a composition comprising the same. The biocontrol agent comprises at least one of:
a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e).

The inventors also contemplated the use of the biocontrol agent according to the invention in the preparation of the pesticidal and growth-promoting compositions.

Therefore, in a further aspect, the invention is directed to the use of a biocontrol agent in the manufacture of a pesticidal composition for preventing, ameliorating, inhibiting, eliminating or delaying the onset of pests infections or infestations. The biocontrol agent comprises at least one of:
a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e).

In yet a further aspect, the invention is directed to the use of a biocontrol agent in the manufacture of a composition for promoting growth in plant. The biocontrol agent comprises at least one of:
a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e).

These and other aspects of the invention will become apparent by the hand of the following figures.

BRIEF DESCRIPTION OF THE FIGURES

FIG. 1A: Cucumber cotyledons treated with distilled water (DW) or L12 spores before inoculation with powdery mildew.
FIG. 1B: L12 growing on PDA secretes pinkish metabolites into the media.

FIG. 2
*P. aphidis* Sequence Alignment with Available Database
A sequence alignment of the L12 isolate (denoted by SEQ ID NO. 5), *P. aphidis* (denoted by SEQ ID NO. 6), *P. regulosa* (denoted by SEQ ID NO. 7) and *P. Antarctica* (denoted by SEQ ID NO. 8) is shown for ITS1.

FIG. 3A: A light microscope image of *P. aphidis* after 10 days growth on PDA media. Arrows mark secretions.

FIG. 3B: Yeast-like growth shapes appear in a light microscope image taken from above of *P. aphidis* on PDA.

FIG. 3C: Synemata-like appearance of *P. aphidis* on PDA as seen in a light microscope.

FIG. 3D: *P. aphidis* mycelium/yeast-like form on PDA as seen in SEM in profile.

FIG. 3E: *P. aphidis* yeast-like form on PDA as seen in SEM from above.

FIG. 3F: *P. aphidis* after 2 days growth on tomato leaf as seen in a light microscope.

FIG. 3G: spore shape on PDB using a hemicytometer in a light microscope.

FIG. 3H: spore shape on YMPD using a hemicytometer in a light microscope.

FIGS. 3I and 3J: *P. aphidis* after 3 days growth on *A. thaliana* leaf (SEM): arrows indicate *P. aphidis*.

*P. aphidis* Survives UV Exposure $10^8$ *P. aphidis* cells inoculated onto PDA plates were exposed to UV for different amounts of time (0, 10, 20 and 30 min) and then transferred into incubator at 25° C. Photos of exposed plates were recorded after 3 weeks.

Abbreviations: Exp. t. UV (min), (Exposure time to UV (min)).

FIG. 5A-5C

*P. aphidis* Culture Optimization

Figure 5A:
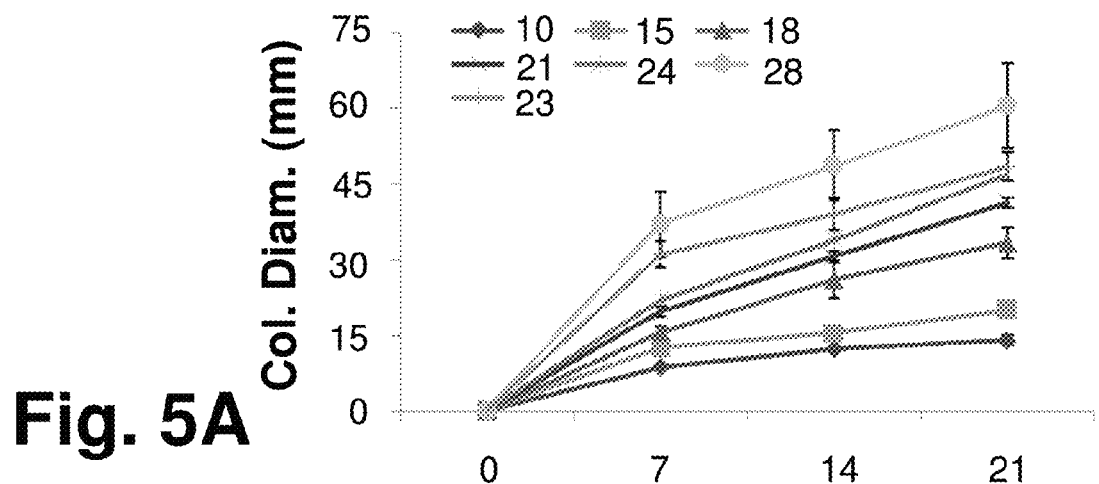

FIG. 5A: PDB-grown *P. aphidis* colony diameter as a function of culture temperature and incubation time is shown.

Figure 5B:
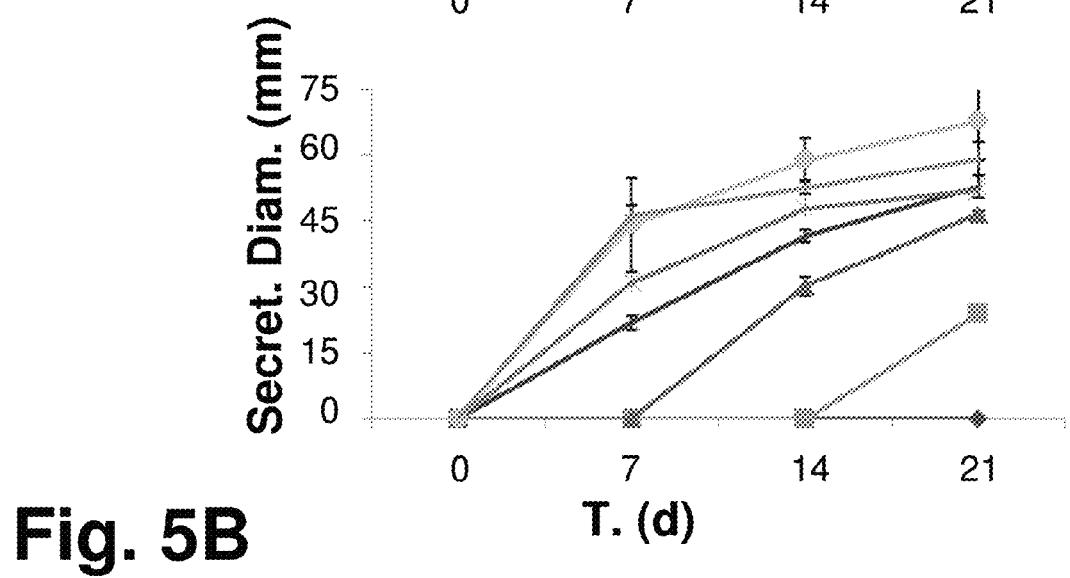

FIG. 5B: PDB-grown *P. aphidis* colony secretions diameter as a function of culture temperature and incubation time is shown.

Figure 5C:
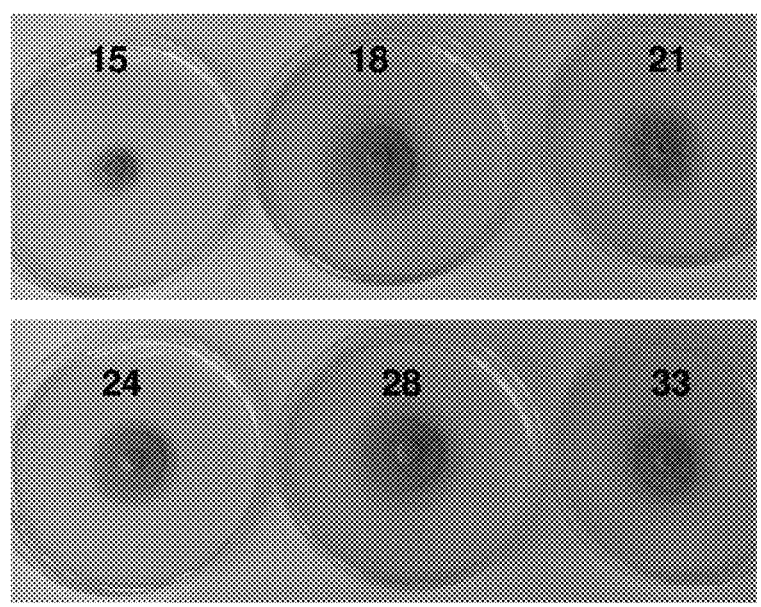

FIG. 5C: Photos of PDB-grown *P. aphidis* grown for 21 days at different temperatures is shown.

Abbreviations: Col. Diam. (mm), (colony diameter (mm)); Secret. Diam. (mm) (secretions diameter (mm)); T. (d), (time (days)).

FIG. 6

Cellulase Secretion by *P. aphidis*

*P. aphidis* was grown on tap water agar plates covered with and without cellulose membrane. Cell number was recorded 7 days post-inoculation. Averages of 10 samples are presented with standard errors bars. *(p<0.05; t-test).

Abbreviations: (M+), (plates covered with cellulose membrane); (M−), (plates without cellulose membrane)

FIG. 7A-7C

In-Vitro Inhibition of Phytopathogens by *P. aphidis* Secretions

Figure 7A:
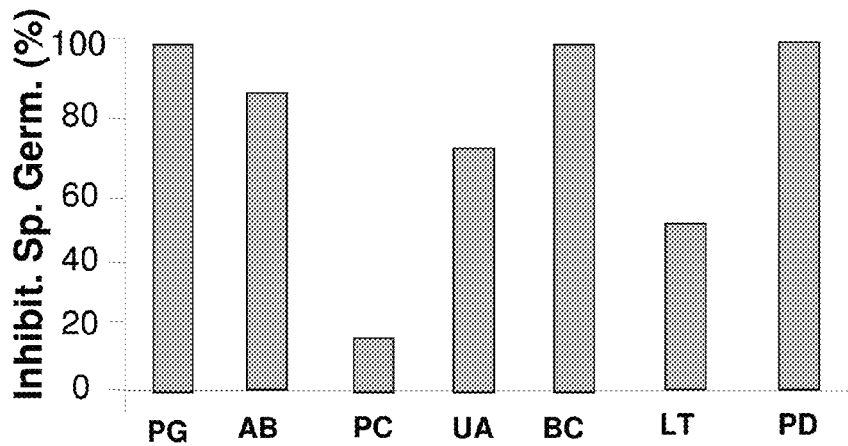

FIG. 7A: L12 were grown on dialysis tubing covering PDA plates. After 10 days, the tubing was removed together with the *P. aphidis* and the plates containing the secreted fraction were used for fungal spore germination assays Inhibition of various fungi (in mm radius) using ethyl-acetate extracts of *P. aphidis* secretions is shown.

Figure 7B:
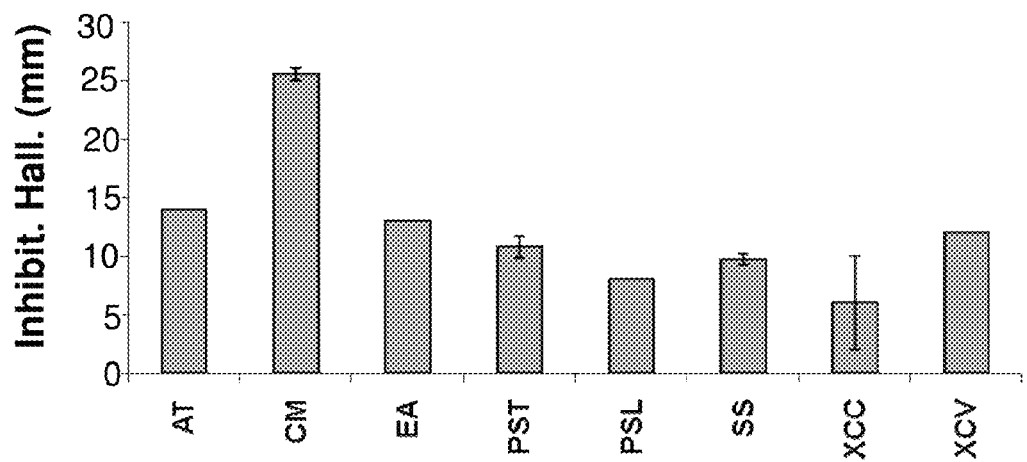

FIG. 7B: Inhibition of various bacteria (in mm radius) using ethyl-acetate extracts of *P. aphidis* secretions.

Figure 7C:
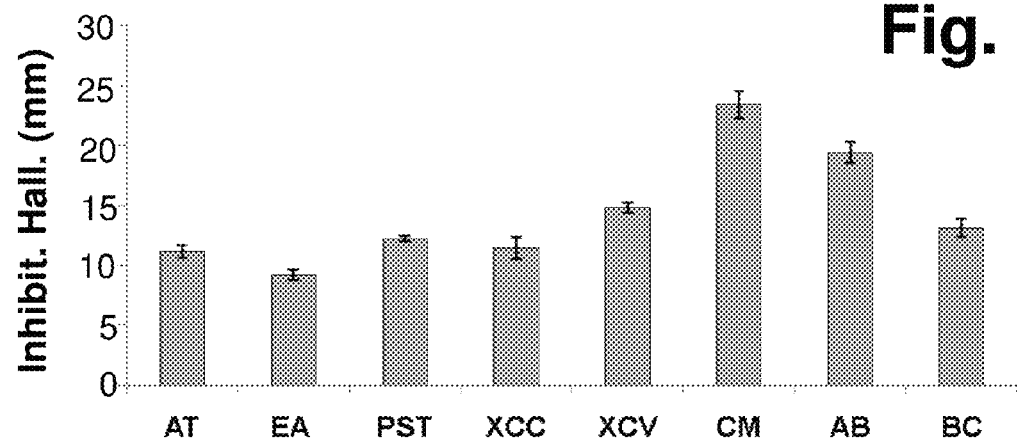

FIG. 7C: Inhibition of various bacteria and fungi (in mm radius) using hexane extracts of *P. aphidis* secretions.

Abbreviations: PG, (*Puccinia graminis*); AB, (*Alternaria brassicicola*); PC, (*Puccinia coronata*); UA, (*Uromyces appendiculatus*); BC, (*Botrytis cinerea*); LT, (*Leveillula taurica*); PD, (*Penicillium digitatum*); AT (*Agrobacterium tumefaciens*); CM (*Clavibacter michiganensis* subsp. *michiganensis*); EA (*Erwinia amylovora*); PST (*Pseudomonas syringae* pv. Tomato); PSL (*Pseudomonas syringae* pv. *Lachrymans*); SS (*Streptomyces scabies*); XCC (*Xanthomonas campestris* pv. Campestris); XCV (*Xanthomonas campestris* pv. *vesicatoria*); Inhibit. Sp. Germ. (%), (inhibition of spore germination (%)); Inhibit. Hall. (mm), (inhibition hallow (mm)).

FIG. 8

Biological Activity of Emitted Volatiles by *P. aphidis*

*P. aphidis* was grown on a compartmentalized PDA dish for 10 days prior to the addition of mycelial plug of *B. cinerea* to the other half of the divided petri dish. Colony diameters of *B. cinerea* were recorded up to 4 days post inoculation in one-half of a compartmentalized petri dish containing *P. aphidis* at the other half as compared with growth on control plates in the absence of *P. aphidis*.

Abbreviations: PA+ (petri-dish containing compartmentalized *P. aphidis*); PA− (petri-dish without *P. aphidis*); Les. Diam. (cm$^2$), (Lesion Diameter (cm$^2$)); T. P. Inoculat. (days), (time post inoculation (days)).

FIG. 9A-9F

Inhibition of Fungi by *P. aphidis* in Detached Leaves and in Planta

Figure 9A:
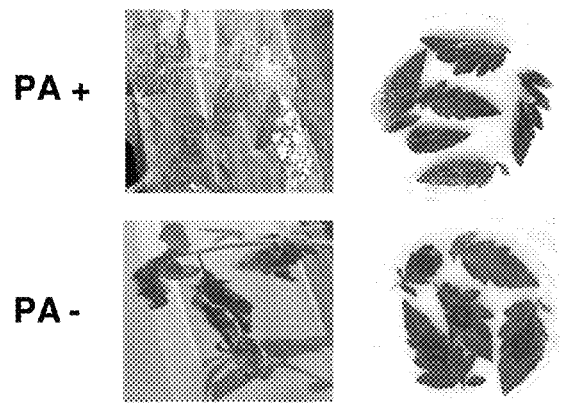

FIG. 9A: Whole tomato plants or detached leaves were sprayed with *P. aphidis* spores or with water before inoculation with *Botrytis cinerea* (7500 spores per leaflet), and infection was scored 5 days post-inoculation. Shown are photos of plants and detached leaves treated with $10^8$ spores/ml.

Figure 9B:
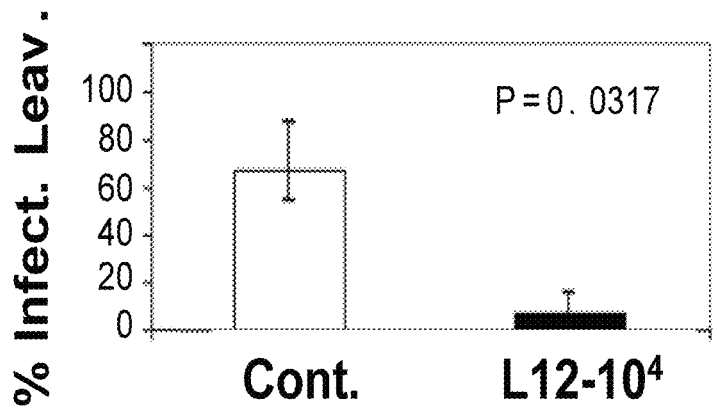

FIG. 9B: Detached tomato leaflets sprayed with *P. aphidis* spores ($10^8$ spores/ml) before inoculation with *B. cinerea* (5 ml for each leaflet; 1500 spores/ml).

Figure 9C:
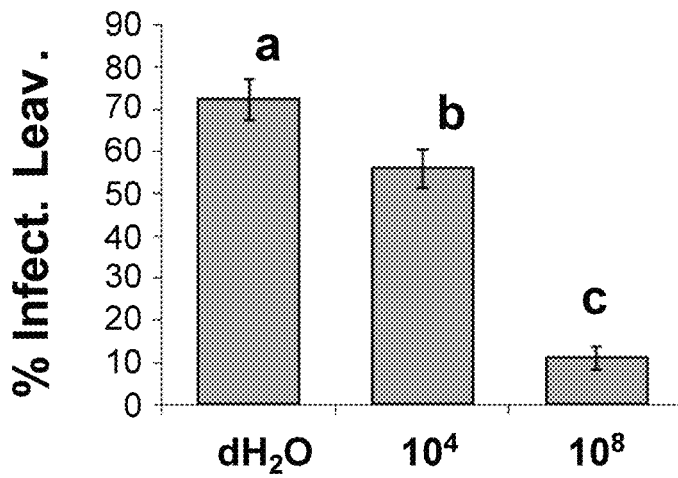

FIG. 9C: Whole tomato plants sprayed with *P. aphidis* spores ($10^4$ or $10^8$ spores/ml) before inoculation with *B. cinerea* (5 ml for each leaflet; 1500 spores/ml).

Figure 9D:
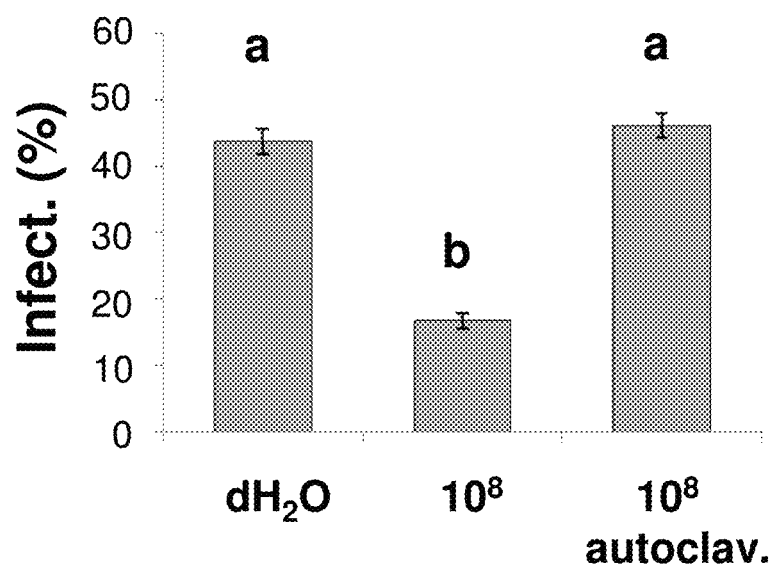

FIG. 9D: Whole tomato plants sprayed with $10^8$ spores/ml autoclaved or non-autoclaved *P. aphidis* spores before inoculation with *B. cinerea* (5 ml for each leaflet; 1500 spores/ml).

Figure 9E:
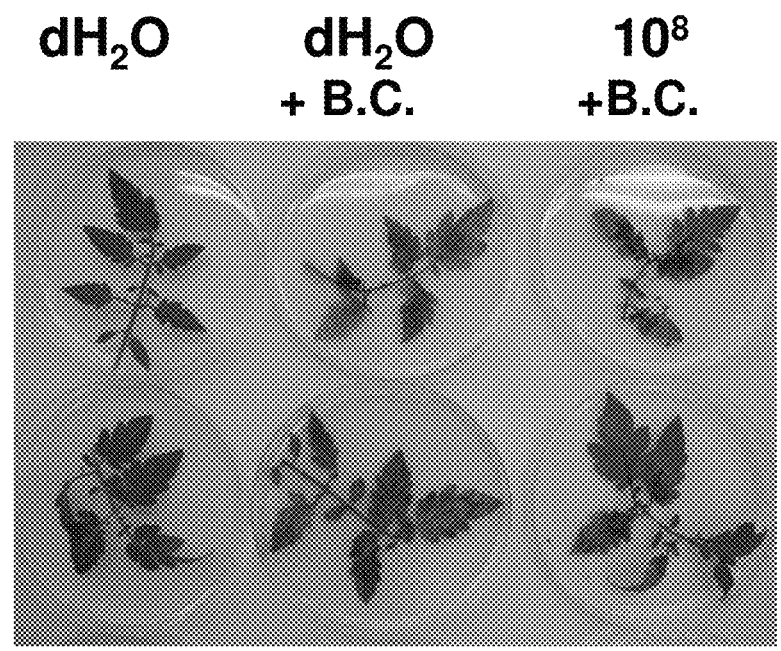

FIG. 9E: Detached tomato leaves sprayed with *P. aphidis* $10^8$ spores/ml 3 days post-infection with *B. cinerea*. Shown are photos of detached leaves 10 days post spraying with *P. aphidis*.

Figure 9F:
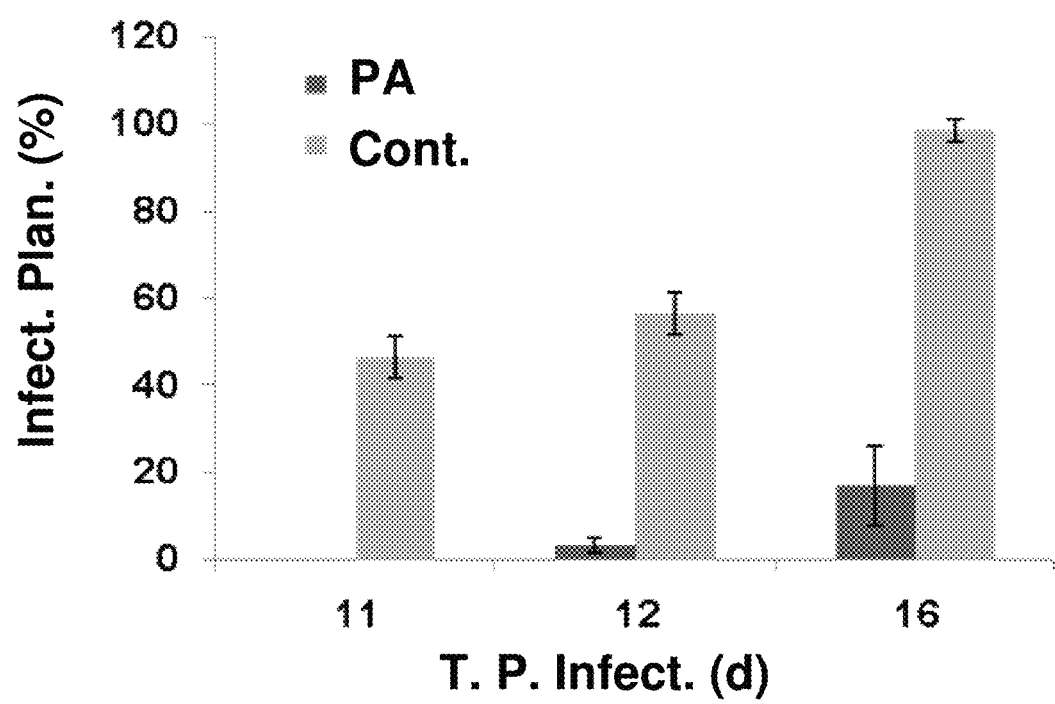

FIG. 9F: Cucumber seedlings sprayed with *P. aphidis* spores ($10^8$ spores/ml) (PA) or with water (Control) three days before inoculation with *Sphaerotheca fuliginea*. Infection was scored 11, 12 and 16 days post-inoculation.

Abbreviations: % Infect. Leav. (% infected leaves); % Infect. (% infections); Cont. (control); L12-$10^4$ (*P. aphidis* L12 $10^4$ spores/ml); L12-$10^8$ (*P. aphidis* L12 $10^8$ spores/ml); autoclave. (autoclaved); dH$_2$O (distilled water); Wh. Plan. (whole plant); Detac. Leav. (detached leaves); T. P. Infect. (d), (time post infection (days)); PA (treated with *P. aphidis*); B.C. (*B. cinerea*.).

FIG. 10A-10B

Inhibition of Bacteria by *P. aphidis* in Planta

Figure 10A:
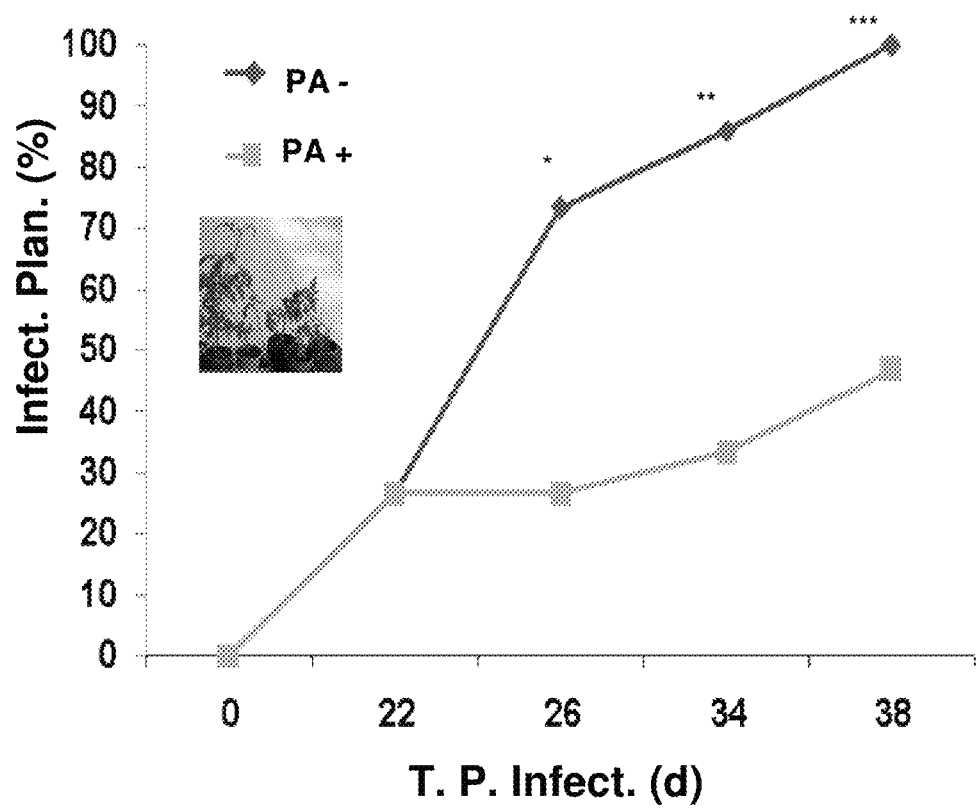

FIG. 10A: Whole tomato plants were sprayed with *P. aphidis* spores ($10^8$ spores/ml) (PA) or with water (Control) before inoculation with *Clavibacter michiganensis* (OD$_{600}$~0.9) and recorded for 38 days post-inoculation. Symptoms scored during 38 days post-inoculation.

Figure 10B:
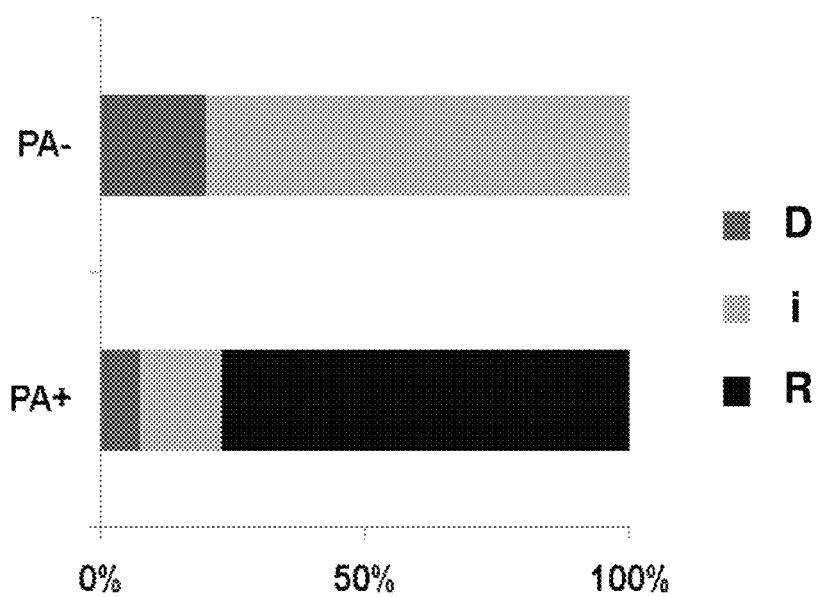

FIG. 10B: Recovery scored after 38 days post-inoculation.

Abbreviations: PA+ (treated with *P. aphidis*); PA− (untreated); T.P. Infect. (d), (time post infection (days)); Infect. Plan. (%), (infected plants (%)); D (dead); I (infected); R (recovered).

FIG. 11A-11C

Growth Promoting Effects of *Pseudozyma aphidis* Application

Figure 11A:
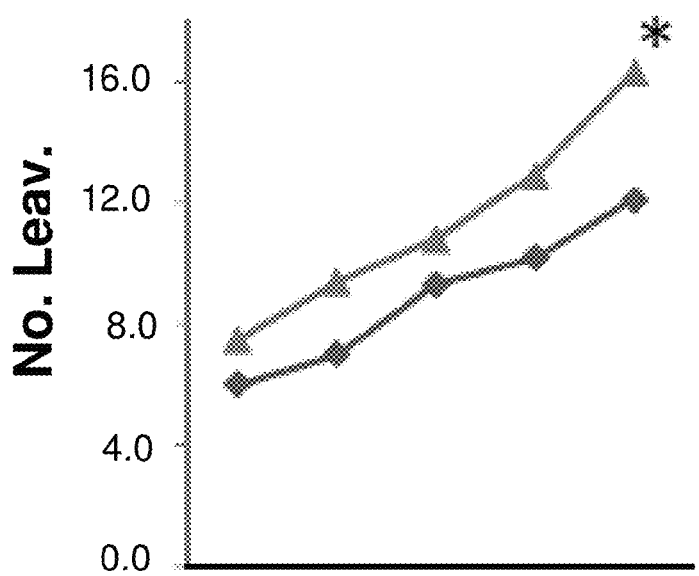
Figure 11B:
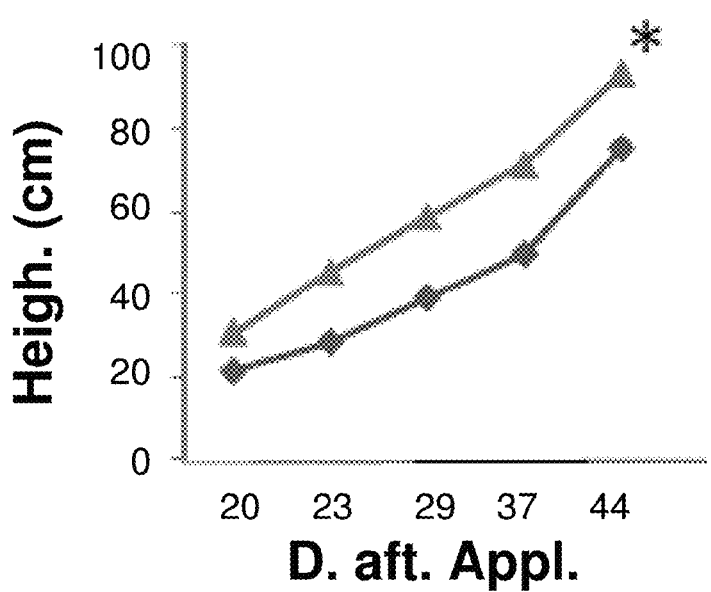
Figure 11C:
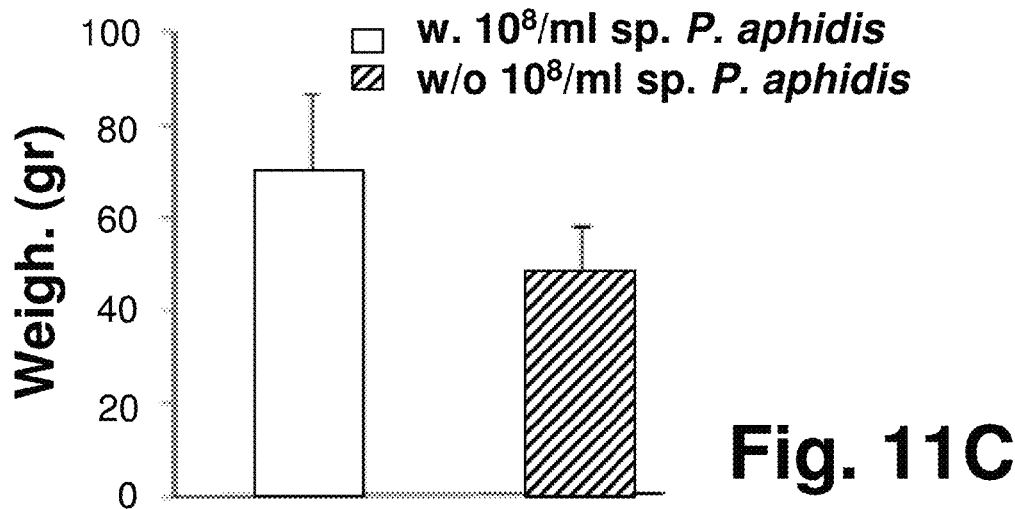

FIG. 11A: Tomato seedlings were sprayed four times with $10^8$ *P. aphidis* spores/ml at 1- to 2-week intervals and their leaf number was monitored through 7 weeks of growth after first application;

FIG. 11B: Leaf height monitored through 7 weeks of growth after first application;

FIG. 11C: Weight was monitored 7 weeks after first application.

Treated plants represented by lines with triangles or white bars, untreated plants represented by line with squares or striped bars; asterisks mean statistical different by t-test p<0.05.

Abbreviations: No. Leav. (number of leaves); Heigh. (cm) (height (cm)); Weigh. (gr) (weight (gr)); D. aft. Appl. (days after application); w. $10^8$/ml sp. *P. aphidis* (with $10^8$ *P. aphidis* spores/ml treatment); w/o $10^8$/ml sp. *P. aphidis* (without $10^8$ *P. aphidis* spores/ml treatment).

FIG. 12A-12B

L12-Induced Resistance

Figure 12A:
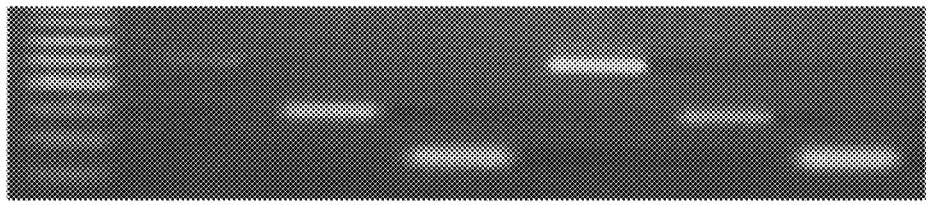

FIG. 12A: Tomato plants were sprayed with $10^8$ *P. aphidis* and PR1, PDF1.2 and PIN2 gene expression was monitored 10 days after application using semi-quantitative PCR as compared to untreated plants.

Figure 12B:
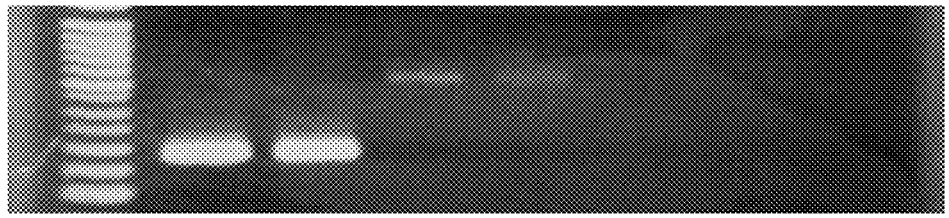

FIG. 12B: *Arabidopsis* plants were sprayed with $10^8$ *P. aphidis* and PR1 and PDF1.2 gene expression was monitored 10 days after application using semi-quantitative PCR as compared to untreated plants.

Abbreviations: Cont. (control); Treat. (treated).

FIG. 13A-13C

L12 Controls *Botrytis cinerea* on *Arabidopsis* Mutant Impaired in SA Accumulation and JA Signaling

*B. cinerea* lesion size was measured 24 to 72 h after inoculation of hormone mutants NahG (SA-deficient), jar1-1 (JA-insensitive), npr1-1 (JA-insensitive) and the WT (PA−), and compared to lesions on their counterparts sprayed with *P. aphidis* (PA+).

Figure 13A:
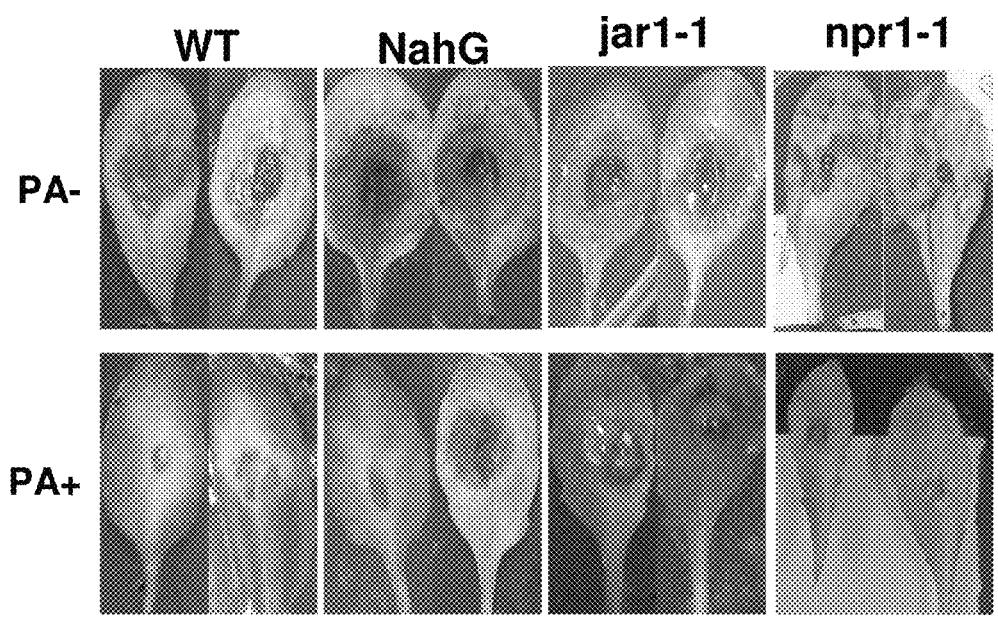

FIG. 13A: recorded photos of *Arabidopsis* WT, NahG and jar1-1 sprayed with *P. aphidis*, versus un-sprayed counterparts.

Figure 13B:
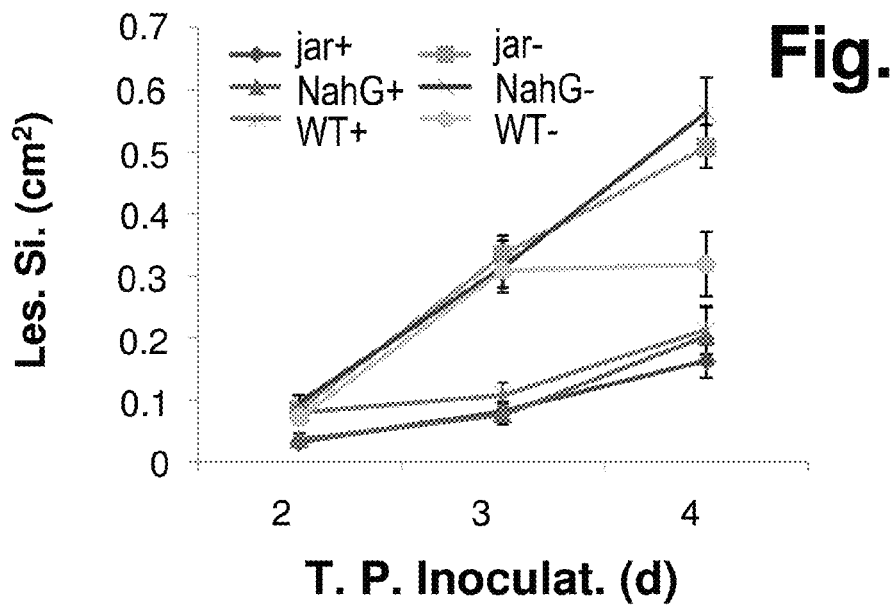

FIG. 13B: recorded lesion size of *Arabidopsis* WT, NahG and jar1-1 sprayed with *P. aphidis*, versus un-sprayed counterparts.

Figure 13C:
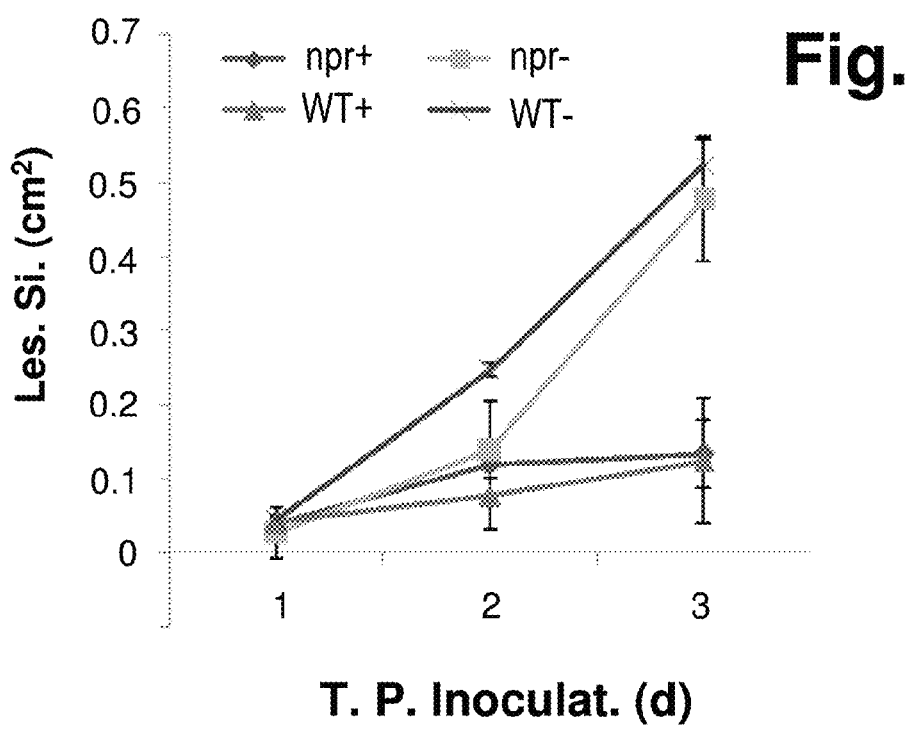

FIG. 13C: recorded lesion size of *Arabidopsis* WT and npr1-1 sprayed with *P. aphidis*, versus un-sprayed counterparts.

Abbreviations: PA+ (petri-dish containing compartmentalized *P. aphidis*); PA− (petri-dish without *P. aphidis*); Les. Si. ($cm^2$), (lesion size ($cm^2$)); T. P. Inoculat. (d), (time post inoculation (days)); W.T. (Wild type).

DETAILED DESCRIPTION OF THE INVENTION

The invention relates to a biocontrol agent comprising *Pseudozyma aphidis* cells and any preparation thereof, and their application in promoting plant growth and health. More specifically, the invention discloses bactericidal, fungicidal, anti-viral, pesticidal and plant growth-promoting compositions comprising ingredients from *Pseudozyma aphidis* cells or an preparation thereof, methods for enhancing plant resistance to phytopathogens, methods for inducing immune-related genes in plants and methods for promoting plant growth using the biocontrol agent of the invention.

Thus, in the first aspect, the invention provides a pesticidal composition comprising as an active ingredient a biocontrol agent comprising at least one of:

a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e). It should be noted that the composition optionally further comprising carriers, diluents and excipients.

The pesticidal composition is therefore effective for the protection and preservation, as well as for the treatment of infected or infested plants, humans, livestock, commercial crops, farm produce and industrial materials.

The term "pesticide" refers to a substance or mixture of substances intended for preventing, destroying or controlling any pest. Specifically, the term relates to substances or mixtures which are effective for treating, preventing, ameliorating, inhibiting, eliminating or delaying the onset of bacterial, fungal, viral, insect- or other pest-related infection or infestation, spore germination and hyphae growth. Also used as substances applied to crops either before or after harvest to protect the commodity from deterioration during storage and transport.

The term "pest" is defined herein as encompassing vectors of plant, humans or livestock disease, unwanted species of bacteria, fungi, viruses, insects, nematodes or any organism causing harm during or otherwise interfering with the production, processing, storage, transport or marketing of food, agricultural commodities, wood and wood products or animal feedstuffs.

The invention thus further provides a biocontrol agent for use as a pesticidal composition. Biological control is defined as the reduction of pest populations by natural enemies and typically involves an active human role. Biological control agents of plant diseases are most often referred to as antagonists. Successful biological control reduces the population density of the target species. The term "biocontrol agent" refers to a compound or composition which originates in a biological matter and is effective in the treatment, prevention, amelioration, inhibition, elimination or delaying the onset of at least one of bacterial, fungal, viral, insect, or any other plant pest infections or infestations and inhibition of spore germination and hyphae growth. It is appreciated that any biocontrol agent is environmentally safe, that it, it is detrimental to the target species, but does not substantially damage other species in a non-specific manner. Furthermore, it is understood that the term "biocontrol agent" also encompasses the term "biochemical control agent". Biochemical control agents are semichemicals for example, plant-growth regulators, hormones, enzymes, pheromones, allomones and kairomones, which are either naturally occurring or identical to a natural product, that attract, retard, destroy or otherwise exert a pesticidal activity.

The biocontrol agent comprised within the composition according to the invention, comprises *Pseudozyma aphidis* cells. "*Pseudozyma aphidis* cells" refers to *P. aphidis* that is dimorphic, meaning it can take a filamentous and/or a yeast form, which includes budding and blastoconidia formations. More specifically, the strain *Pseudozyma aphidis* is synonym to *Sterigmatos aphidis* which was described in detail by Henninger and Windisch [Arch. Microbiol., 1975, 105, page 49-50]. The strain was isolated from the secretions of Aphididae on leaves of *Solanum pseudocapsicum* and is able to assimilate both inositol and potassium nitrate. A broad range of carbon sources can be used by these fungi such as pentoses, hexoses, sugar alcohols, soluble starch, ethanol and organic acids. Urease reaction is positive. Staining with Dazionium Blue B salt is also positive. Initial growth on malt-extract agar at 28° C. shows elongated cells (1.4-3.6)×(4.3-11.5 μm) often pointed at one or both ends. Very long cells up to 40 Am are also observed. After growth is completed the agar is covered with a thin aerial mycelium made up of ramifying, acropetal chains of fusiform blastconidia originating from short denticles, sterigma-like structures or attenuating hyphae. Microscopically it shows septated hyphae with the cytoplasm retracted in some cells and with retraction septa. The streak culture is variable, sometimes powdery, mostly rough and flat with rough margin. The color is cream to yellow. The fungi are anamorph to Ustilaginales because the comparison of the 26S ribosomal DNA placed it in the same group with *Ustilago maydis* [Boekhout, J. Gen. Appl. Microbiol., 1995, 41, page 359-366].

It is understood that the composition of the invention may comprise *Pseudozyma aphidis* cells or any isolate or mutant thereof. The expression "isolate or mutant" is interpreted as any individual or homogenous group of individuals having substantially the same allelic complement. It is understood that in a heterogenic population of individuals, allelic heterogeneity exists, wherein some individuals carry mutations in some of their genes, such as deletions, substitutions, duplications and the likes. An individual carrying such mutations is thus a mutant. An individual removed from said heterogenic population is said to be isolated, as are genetically substantially identical progeny thereof. It is also appreciated that in the present context, "mutant" and "isolate" relates to *Pseudozyma aphidis* individuals mutated in genes so as to confer a detectable phenotype, and in specific embodiments said phenotype is related to the pesticidal or commercially-relevant characteristic of *P. aphidis*.

Still further, the composition of the invention comprises as a biocontrol agent *P. aphidis* spores. A "spore" as contemplated by the present invention refers to at least one dormant (at application) but viable reproductive unit of a bacterial or fungal species, specifically, fungal. The term "*Pseudozyma aphidis* spores" refers to cylindrical to fusiform blastoconidia. The active material can be spores, yeast-like forms, filamentous forms or a combination of some or all. On leaves, one finds the dimorphic fungal body, which includes blastoconidia on strigmata, whereas in liquid media, the yeast-like form and spores are mainly found, and in solid media filamentous and spore forms are common.

Alternatively or additionally, the composition of the invention may comprise as a biocontrol agent, culture medium of *Pseudozyma aphidis*. The terms "culture medium of *Pseudozyma aphidis*" or "conditioned medium" refers to a medium or a liquid carrier in which the *Pseudozyma aphidis* were previously grown and to which they secreted compounds. Culture filtrate metabolites are the compounds secreted into the growth media. The culture medium may be used as is, or may be further processed by at least one of filtration, centrifugation and extraction.

In yet another embodiment, the composition of the invention may comprise as active ingredient any preparation or secreted fraction of *Pseudozyma aphidis*. "*Pseudozyma aphidis* secreted fraction" refers to compounds generated and secreted from the cells.

It should be further noted that any extract or preparation of said *Pseudozyma aphidis* cells may be used as a biocontrol agent by the composition of the invention. The term "extracts" refers to any substances obtained by extracting *Pseudozyma aphidis* cells, spores, culture-filtrate or conditioned medium using organic solvents such as, for example, ethyl-acetate or hexane.

Importantly, the composition of the invention may comprise any combination of *Pseudozyma aphidis* cells, mutants, isolates, extracts or conditioned medium as described herein.

It is understood that the composition of the invention may optionally further comprise an agriculturally acceptable carrier, diluent, emulsifier or dispersant.

It is appreciated that the composition is also effective for treating, preventing, ameliorating, inhibiting, reducing or eliminating an established bacterial, fungal, viral, insect, or any other pest infection or infestation, and in treating and preventing diseases caused thereby.

As used herein in the specification and in the claims section below, the term "treat" or "treating" and their derivatives includes substantially inhibiting, slowing or reversing the progression of a condition, substantially ameliorating symptoms of a condition or substantially preventing the appearance of symptoms of a condition, said condition is brought about in plants by plant pathogens, including bacterial, fungal, viral, insect or other plant pests, spores or hyphae.

The term "prevent" and all variations of this term is intended to mean the countering in advance of bacterial, fungal, viral, insect or other pest growth, proliferation, infestation, infection, spore germination and hyphae growth. In this case it is understood that the composition is applied prior to exposure to said pathogens.

The terms "ameliorate" and "amelioration" relate to the improvement in the treated plant condition brought about by the compositions and methods according to the invention, wherein said improvement may be manifested in the forms of inhibition of fungal hyphae formation and/or its destruction, partial or full, inhibition of fungal and bacterial spore germination, inhibition of fungal, bacterial or other pests growth and proliferation, induction of plant immune responses and improvement in said diseased plant height, weight, number of leaves and root system. In general, the term refers to the improvement in a diseased plant physiological state.

It should be further indicated that in certain embodiments where the treated subject is a human or livestock, the term "treat" or "treating" and their derivatives includes substantially inhibiting, slowing or reversing the progression of a condition, substantially ameliorating symptoms of a condition or substantially preventing the appearance of symptoms of a condition, said condition is brought about in human or livestock by human or livestock pathogens, including bacterial, fungal, viral, insect or other plant pests, spores or hyphae.

The term "inhibit" and all variations of this term is intended to encompass the restriction or prohibition of bacterial, fungal, viral, insect, or any other pest growth, as well as spore germination.

The term "eliminate" relates to the substantial eradication or removal of bacteria, fungi, viruses, insects, or any other pests by contacting them with the composition of the invention, optionally, according to the methods of the invention described below.

The terms "delay", "retard" and all variations thereof are intended to encompass the slowing of the progress of bacterial, fungal, viral, insect or any other pest growth, and spore germination. The expression "delaying the onset" is interpreted as preventing or slowing the progression of bacterial, fungal, viral, insect, or any other pest growth, infestation, infection, spore germination and hyphae growth for a period of time, such that said bacterial, fungal, viral, insect, or any other pest growth, infestation, infection, spore germination and hyphae growth do not progress as far along in development, or appear later than in the absence of the treatment according to the invention.

The pesticidal composition according to the invention comprises material derived from *Pseudozyma aphidis*. It protects plants, or any other material, from the damaging effects of microorganisms such as fungi and bacteria (as shown in Examples 7-10), as well as viruses, insects, nematodes and other pests. Moreover, not only do the compositions according to the invention harm pathogenic organisms, they also enhance plant growth and induce plant pathogen resistance genes, as shown by Examples 11 and 12, respectively.

In more specific embodiments, the pesticidal composition of the invention is a bactericidal composition for treating, preventing, ameliorating, inhibiting, eliminating or delaying the onset of bacterial infections or infestations. "Bactericidal", as used herein, relates to a pesticide which is specifically effective in treating, preventing, ameliorating, inhibiting, eliminating or delaying the onset of bacterial growth and/or spore germination. The compositions of the invention can therefore serve as bactericides, as Examples 7 and 9 show. The compositions may be especially effective as bactericides for controlling *Clavibacter michiganensis* subsp. *michiganensis, Agrobacterium tumefaciens, Erwinia amylovora, Pseudomonas syringae* pv. *lachrymans, Pseudomonas syringae* pv. tomato, *Streptomyces scabies, Xanthomonas campestris* pv. *campestris* and *Xanthomonas capestris* pv. *vesicatoria*.

More specifically, it is understood that the composition is effective for treating, preventing, ameliorating, inhibiting, reducing or eliminating an established bacterial infection, and in treating and preventing diseases caused thereby.

According to other embodiments, the compositions, as well as the methods according to the invention (described herein after), are particularly effective in preventing, inhibiting or eliminating, either partially or fully, infection of plants by bacteria, non-limiting examples of which include: *Xanthomonas* species, such as, for example, *Xanthomonas campestris* pv. *oryzae; Pseudomonas* species, such as, for example, *Pseudomonas syringae* pv. *lachrymans; Erwinia* species, such as, for example, *Erwinia amylovora; Clavibacter michiganensis, Agrobacterium tumefaciens, Streptomyces scabies*.

In more specific embodiments as also demonstrated by Examples 7, 8 and 9, the bactericidal composition according to the invention, may be particularly applicable where bacterial infections are caused by at least one of: *Clavibacter michiganensis, Agrobacterium tumefaciens, Erwinia amylovora, Pseudomonas syringae* pv. *lachrymans, Pseudomonas syringae* pv. tomato, *Streptomyces scabies, Xanthomonas campestris* pv. *campestris* and *Xanthomonas capestris* pv. *vesicatoria*.

In specific embodiment, the composition of the invention is specifically effective in treating and preventing *Clavibacter michiganensis* infections and pathogenic conditions caused thereby. *Clavibacter michiganensis* is an aerobic non-sporulating Gram-positive plant pathogenic bacterium that currently constitutes the only species within the genus *Clavibacter*. *Clavibacter michiganensis* currently has five subspecies: *Clavibacter michiganensis* subsp. *insidiosus, Clavibacter michiganensis* subsp. *michiganensis, Clavibacter michiganensis* subsp. *nebraskensis, Clavibacter michiganensis* subsp. *sepedonicus* and *Clavibacter michiganensis* subsp. *tesselarius*. *Clavibacter michiganensis* subsp. *michiganensis* is the causative agent of bacterial canker of tomato.

In yet another embodiment, the bactericidal composition of the invention is effective is cases of *Agrobacterium tumefaciens* infections. *Agrobacterium tumefaciens* (updated scientific name: *Rhizobium radiobacter*) is the causal agent of crown gall disease (the formation of tumours) in over 140 species of dicot. It is a rod shaped, Gram negative soil bacterium. Symptoms are caused by the insertion of a small segment of DNA (known as the T-DNA, for 'transfer DNA') into the plant cell, which is incorporated at a semi-random location into the plant genome. *Agrobacterium tumefaciens* (or *A. tumefaciens*) is an alphaproteobacterium of the family Rhizobiaceae, which includes the nitrogen fixing legume symbionts. Unlike the nitrogen fixing symbionts, tumor producing *Agrobacterium* are pathogenic and do not benefit the plant. The wide variety of plants affected by *Agrobacterium* makes it of great concern to the agriculture industry. Economically, *A. tumefaciens* is a serious pathogen of walnuts, grape vines, stone fruits, nut trees, sugar beets, horse radish and rhubarb.

Still further, the bactericidal composition of the invention is effective is cases of *Erwinia amylovora* infections. *Erwinia amylovora* is a Gram-negative bacterium in the family Enterobacteriaceae, and is responsible to Fire blight. Fire blight is a contagious disease affecting apples, pears, and some other members of the family Rosaceae. It is a serious concern to producers of apples and pears. Under optimal conditions, it can destroy an entire orchard in a single growing season. Pears are the most susceptible, but apples, loquat, crabapples, quinces, hawthorn, cotoneaster, pyracantha, raspberry and some other rosaceous plants are also vulnerable.

*Pseudomonas syringae* that is another example of the invention is a rod shaped, Gram-negative bacterium with polar flagella. It is a plant pathogen which can infect a wide range of plant species, and exists as over 50 different pathovars. Many of these pathovars were once considered to be individual species within the *Pseudomonas* genus, but molecular biology techniques such as DNA hybridization have shown these to in fact all be part of the *P. syringae* species. *P. syringae* also produce Ina proteins which cause water to freeze at fairly high temperatures, resulting in injury to plants.

In yet another embodiment, the composition of the invention may be effective in treating *Streptomyces scabies* infections and pathogenic conditions caused thereby. *Streptomyces scabies* is one of three *streptomyces* species that causes common scab symptoms on potatoes and other root crops. *S. scabies* is present in soils in all the potato growing regions of the world and also affects other fleshy root crops. Potatoes (*Solanum tuberosum*) are the main economic host but other fleshy root crops, including beets, radish, rutabaga, turnip, carrot and parsnips, are affected.

The composition of the invention may be used for treating *Xanthomonas campestris* infections. *Xanthomonas campestris* is a bacterial species that causes a variety of plant diseases. It is a Gram-negative aerobic rod, and the causal agent of black rot, which affects crucifers such as *Brassica* and *Arabidopsis*. Symptoms include marginal leaf chlorosis and darkening of vascular tissue, accompanied by extensive wilting and necrosis. Full leaf yellowing, wilting, and necrosis occur as the disease advances.

As demonstrated by Examples 7, 15 and 16, the *P. aphidis* biocontrol agent of the invention is effective in treating, and preventing disease symptoms caused by fungal pathogens. Thus, in specific embodiments, the pesticidal composition is a fungicidal composition for treating, preventing, ameliorating, inhibiting, eliminating or delaying the onset of fungal infections or infestations.

The term "fungicidal" relates to a pesticide which is specifically effective in treating, preventing, ameliorating, inhibiting, eliminating or delaying the onset of fungal growth and/or spore germination and hyphae formation and growth. The compositions of the invention can therefore serve as fungicides, as Examples 7 and 8 demonstrate. The compositions may be especially effective as fungicides for controlling *Botrytis cinerea, Penicillium digitatum, Alternaria brassici-* cola, *Uromyces appendiculatus, Leveillula taurica, Sclerotinia sclerotiorum* and *Puccinia coronate*.

It is understood that the composition is also effective for treating, preventing, ameliorating, inhibiting or eliminating an established fungal infection, and in treating and preventing diseases caused thereby.

The composition and method according to the invention may be particularly suitable for preventing, inhibiting or eliminating, either partially or fully, fungal and fungal-like plant pathogens, non-limiting examples of which include: *Armillaria* species, such as, for example, *Armillaria borealis*; Brachybasidiaceae species; *Brasiliomyces* species; such as, for example, *Brasiliomyces malachrae; Calonectria* species, such as, for example, *Calonectria ilicicola*; Chrysanthemum white rust; *Conidiosporomyces*; Cryptobasidiaceae; Exobasidiaceae; *Fusarium* species, such as, for example, *Fusarium oxysporum* f.sp. *carthami; Gibberella* species, such as, for example, *Gibberella tricincta; Gliocladiopsis* species, such as, for example, *Gliocladiopsis tenuis*; Graphiolaceae; *Gymnosporangium* species, such as, for example, *Gymnosporangium libocedri; Nectria* species, such as, for example, *Nectria pseudotrichia; Pleuroceras; Puccinia* species, such as, for example, *Puccinia malvacearum; Thecaphora* species, such as, for example, *Thecaphora solani; Venturia* (genus) and *Westea*; fungal-like (Oomycota) species such as *Phytium, Phytopthora, albugo* and powdery mildews (*Peronospora, Bremia, Peronosclerospora, Plasmopara* and *Pseudoperonospora*).

In some embodiments of the composition of the invention, the fungal infections are caused by at least one of: *Botrytis cinerea, Penicillium digitatum, Alternaria brassicicola, Uromyces appendiculatus, Leveillula taurica, Sclerotinia sclerotiorum* and *Puccinia coronate*.

According to one specific embodiment, the composition of the invention is particularly suitable for treating *Botrytis cinerea* infections and pathologic conditions caused thereby. *Botrytis cinerea* is a necrotrophic fungus that affects many plant species, although its most notable hosts may be wine grapes. In viticulture, it is commonly known as *botrytis* bunch rot; in horticulture, it is usually called grey mould or gray mold. The fungus gives rise to two different kinds of infections on grapes. The first, grey rot is the result of consistently wet or humid conditions, and typically results in the loss of the affected bunches. The second, noble rot, occurs when drier conditions follow wetter, and can result in distinctive sweet dessert wines, such as Sauternes or the Aszú of Tokaji. *Botrytis cinerea* affects many other plants. It is economically important on soft fruits such as strawberries and bulb crops. Unlike wine grapes, the affected strawberries are not edible and are discarded. *Botrytis cinerea* is well-known cause for considerable damage in tomato, and also affects rhubarb.

According to another specific embodiment, the composition of the invention is particularly suitable for treating *Penicillium* infections and pathologic conditions caused thereby. *Penicillium* are comparable to *Aspergillus*. The genus *Penicillium* falls into the order Eurotiales. In this order, organisms produce asci within cleistothecia. *Penicillium* is often referred to as Deuteromycetes, or *Fungi imperfecti*. The name *Penicillium* comes from the word "brush"; this refers to the appearance of spores in *Penicillium digitatum Pencillium* fungi are versatile and opportunistic. They are post-harvest pathogens. *Penicillium* species are one of the most common causes of fungal spoilage in fruits and vegetables. *Penicillium italicum* and *Penicillium digitatum* are the most common attackers of citrus fruits, while *Penicillium expansum* is known to attack apples. *P. digitatum* works by producing ethylene to accelerate ripening. It the covers the fruit with green conidia, causing the fruit to shrivel and dry out. *P. italicum* causes slimy rot and produces blue-green conidia. These species like cooler temperatures, which explains why they are usually found on foods left too long in the refrigerator. Many species produce mycotoxins; for example, *P. expansum* produces one called patulin. Most of these species resemble each other in color characteristics, style of decay, and infection symptoms; they fall under a general category called blue mold. *P. expansum* is one of the most aggressive species. These fungi live a long time and are quite durable, even under adverse conditions. Sometimes, *P. italicum* and *P. expansum* will adhere to each other to create synnemata. Synnemata also occurs in *Penicillum claviforme. Penicillium* growth typically occurs as a result of wound infections in produce. The most common treatment is to use fungicide on harvested produce. *Penicillium* species attack more than just fruit. For example, *Penicillium verrucosum* grows on cereal products.

According to another specific embodiment, the composition of the invention is particularly suitable for treating *Alternaria* infections and pathologic conditions caused thereby. The genus *Alternaria* is comprised of many common saprophytic (derive nutrients from dead and/or decaying organic matter) and plant pathogenic species. *Alternaria* spores can be typically found in the air, soil, decaying plant material, wood, and foods. *Alternaria brassicicola* is a ubiquitous plant pathogenic fungus but also exists as a saprophyte. *Alternaria brassicicola* causes black spot disease (also called dark leaf spot) on virtually every important cultivated *Brassica* species including broccoli, cabbage, canola, and mustard. It is of worldwide economic importance resulting occasionally in 20-50% yield reductions in crops such as canola, mustard or rape.

According to another specific embodiment, the composition of the invention is particularly suitable for treating *Uromyces appendiculatus* infections and pathologic conditions caused thereby. The common bean rust disease is caused by the basidiomycete fungus *Uromyces appendiculatus* (Pers.: Pers.) Unger. It is an obligate parasitic fungus that cannot live independently of its common bean host. This fungus cannot be cultured on artificial media in the laboratory. The rust pathogen completes its entire life cycle on the common bean host; thus, this rust is autoecious. The common bean rust disease has a worldwide distribution and it occurs in most dry and snap bean productions areas of the world, and most especially in locations where humid to moderately humid conditions, long dew periods, and cool conditions prevail during the bean growing season.

According to another specific embodiment, the composition of the invention is particularly suitable for treating *Leveillula taurica* infections and pathologic conditions caused thereby. Tomato Powdery Mildew is caused by the fungus *Leveillula taurica*. The disease can be very devastating in commercially grown tomatoes where yield losses may exceed 50% in heavily infected fields. The extent of loss depends on environmental conditions, date of disease onset, and effectiveness of fungicide control. Hot, dry days with an occasional rainstorm are conducive to disease development.

In yet another embodiment, composition of the invention is particularly suitable for treating *Sclerotinia sclerotiorum* infections. *Sclerotinia sclerotiorum* is a plant pathogenic fungus and can cause a disease called white mold if conditions are correct. *S. sclerotiorum* is also known as cottony rot, watery soft rot, stem rot, drop, crown rot and blossom blight. A key characteristic of this pathogen is its ability to produce black resting structures known as sclerotia and white fuzzy growths of mycelium on the plant it infects. These sclerotia give rise to a fruiting body in the spring that produces spores in a sac, hence the term sac fungi (Ascomycetes). This pathogen can occur on many continents and has a wide host range of plants. When *S. sclerotiorum* is onset in the field by favorable environmental conditions, losses can be great. White mold affects a wide range of hosts. It is known to infect 408 plant species. Its diverse host range and ability to infect plants at any stage of growth makes white mold a very serious disease. The fungus can survive on infected tissues, in the soil, and on living plants. It affects young seedlings, mature plants, and fruit in the field or in storage. White mold can spread quickly in the field from plant to plant. It can also spread in a storage facility throughout the harvested crop. Some crops it affects commonly are soybeans, green beans, sunflowers, canola, and peanuts.

Still further, the composition of the invention is intended for treating *Puccinia coronata* infections. *Puccinia coronata* is a plant pathogen and causal agent of oat crown rust and barley crown rust. The pathogen occurs worldwide infecting both wild and cultivated oats. Since 1993, outbreaks of crown rust have occurred on barley and forage grasses at several localities in this region. The extent of yield losses in barley caused by this disease have not been determined. Crown rust posed a threat to barley production, because the first infections in barley occur early in the season from local inoculum.

It is noted that the fungicidal composition of the invention may inhibit at least one of fungal spore germination and hyphae formation.

"Germination", in a general sense, can imply anything expanding into greater being from a small existence or germ. As referred to herein, "germination" relates to the process in which a fungus emerges from a spore, and begins growth. An example of germination is the growth of a sporeling from a spore. Germination can also refer to the emergence of cells from resting spores and the growth of sporeling hyphae or thalli from spores in fungi, algae and some plants. Conidia are asexual reproductive spores of fungi which germinate under specific conditions.

A hypha (plural hyphae) is a long, branching filamentous structure of a fungus, and also of unrelated Actinobacteria. In most fungi, hyphae are the main mode of vegetative growth, and are collectively called a mycelium; yeasts are unicellular fungi that do not grow as hyphae. A hypha consists of one or more cells surrounded by a tubular cell wall. In most fungi, hyphae are divided into cells by internal cross-walls called "septa" (singular septum). Some fungi have aseptate hyphae, meaning their hyphae are not partitioned by septa. Hyphae grow at their tips. During tip growth, cell walls are extended by the external assembly and polymerization of cell wall components, and the internal production of new cell membrane. The spitzenkörper is an intracellular organelle associated with tip growth. It is composed of an aggregation of membrane-bound vesicles containing cell wall components. The spitzenkörper is part of the endomembrane system of fungi, holding and releasing vesicles it receives from the Golgi apparatus. These vesicles travel to the cell membrane via the cytoskeleton and release their contents outside the cell by the process of exocytosis, where it can then be transported to where it is needed. Vesicle membranes contribute to growth of the cell membrane while their contents form new cell wall. The spitzenkörper moves along the apex of the hyphal strand and generates apical growth and branching; the apical growth rate of the hyphal strand parallels and is regulated by the movement of the spitzenkörper. As a hypha extends, septa may be formed behind the growing tip to partition each hypha into individual cells. Hyphae can branch through the bifurcation of a growing tip, or by the emergence of a new tip from an established hypha.

The terms "hyphae formation" and "hyphae growth" as used herein relate to the processes of hyphae outgrowth from spores, also interchangable with the term "spore germination", and the processes of extension and/or bifurcation of growing hyphae tips. It is understood that the treatment of fungi or bacteria with the composition of the invention may inhibit hyphae formation and growth by at least about 5%-95%, about 10%-90%, about 15%-85%, about 20%-80%, about 25%-75%, about 30%-70%, about 35%-65%, about 40%-60% or about 45%-55%. Said inhibition of hyphae formation and growth may also be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100%.

More specifically, the term "inhibit" or "inhibition", as used herein, means the restriction, retardation, reduction, decrease or diminishing of a process, a phenomenon or a phenotype by at least about 1%-100%, about 5%-95%, about 10%-90%, about 15%-85%, about 20%-80%, about 25%-75%, about 30%-70%, about 35%-65%, about 40%-60% or about 45%-55%. Said restriction, retardation, reduction, decrease or diminishing of a process, a phenomenon or a phenotype may also be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100%.

It is also noted that the pesticidal composition of the invention may additionally serve as an anti-viral composition for treating, preventing, ameliorating, inhibiting, eliminating or delaying the onset of viral infections. Non-limiting examples of plant-pathogenic viruses include: Rhabdovirus, Alfalfa enation virus (AEV); Alfamovirus, Alfalfa mosaic virus (AMV)); Luteovirus, Bean leaf roll virus (BLRV); Potyvirus, Bean yellow mosaic virus (BYMV); Cucumovirus, Cucumber mosaic virus (CMV); Nepovirus, Lucerne Australian latent virus (LALV); Comoviridae, Lucerne Australian symptomless virus (LASV); Sobemovirus, Lucerne transient streak virus (LTSV); Carlavirus, Pea streak virus (PSV); Carlavirus, Red clover vein mosaic virus (RCVMV); Ilarvirus, Tobacco streak virus (TSV); Tobacco etch virus; Potexvirus, White clover mosaic virus (WCMV); Arabis mosaic virus; Artichoke Italian latent virus; phytoplasma; Bratislava mosaic virus; Broad bean wilt virus; Grapevine Virus B; Grapevine fanleaf virus; Peach rosette mosaic virus; Petunia asteroid mosaic virus; Raspberry ringspot virus; Sowbane mosaic virus; Strawberry latent ringspot virus; Tobacco mosaic virus; Tobacco necrosis virus; Tobacco ringspot virus; Tomato black ring virus; and Tomato ringspot virus.

According to certain embodiments, the pesticidal composition of the invention may be particularly suitable for treating, preventing, ameliorating, inhibiting, eliminating or delaying the onset of at least one of bacterial, fungal, viral, insect, or any other pest infection or infestation in humans.

In other embodiments, the pesticidal composition of the invention may be particularly suitable for treating, preventing, ameliorating, inhibiting, eliminating or delaying the onset of at least one of bacterial, fungal, viral, insect, or any other pest infection or infestation in livestock.

In more specific embodiments, the pesticidal composition of the invention may be useful for treating, preventing, ameliorating, inhibiting, eliminating or delaying the onset of a bacterial infection in humans or livestock caused by at least one of *Mycobacterium tuberculosis, Staphylococcus, Streptococcus, Pseudomonas, Shigella, Campylobacter, Burkholderia cenocepacia, Mycobacterium avium* and *Salmonella*.

In further specific embodiments, the pesticidal composition of the invention may be useful for treating, preventing, ameliorating, inhibiting, eliminating or delaying the onset of a fungal infection in humans or livestock caused by at least one of *Candida, Aspergillus, Phycomyces, Zygomyces, Rhizopus, Mucor, Absidia, Piedraia hortae, Trichosporon beigelii, Exophiala werneckii, Microsporum, Cladosporium, Fonsecaea, Fusarium, Penicillium, Epidermophyton, Microsporum, Trichophyton, Malassezia furfur, Pityriasis versicolor, Coccidioides immitis, Histoplasma capsulatum, Blastomycoses dermatitidis, Cryptococcus neoformans, Sporothrix schenckii*.

In more specific embodiments, the pesticidal composition of the invention may be useful for treating, preventing, ameliorating, inhibiting, eliminating or delaying the onset of a viral infection in humans or livestock caused by at least one of the virus families of: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae.

In another aspect, the invention provides a composition that confers resistance in plants against pests, infections or infestations. The composition comprises at least one of:
a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d);
f. a combination of at least two of the biocontrol agents defined in (a) to (e). The composition optionally further comprises carriers, diluents and excipients.

According to various embodiments of the invention, the compositions of the invention confer resistance in treated plants.

The term "resistance" relates to the ability of plants to withstand bacterial, fungal, viral, insect or other pest infections or infestations, that is, said plants may demonstrate better survival rates during and after such infections or infestations as compared with non-treated plants, it may show lesser symptoms as compared with non-treated plants, or it may not be infected or infested in as high a rates as non-treated plants.

For example, a plant treated with the composition of the invention may be resistant to pest infections or infestations and infection or infestation rate would by about 1%-100%, about 5%-95%, about 10%-90%, about 15%-85%, about 20%-80%, about 25%-75%, about 30%-70%, about 35%-65%, about 40%-60% or about 45%-55% lower than non-treated plants, or at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% lower than non-treated plants.

Treated plants survival rate may by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% higher than non-treated plants.

Pathologic symptoms caused by such infections or infestations may be inhibited or reduced by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% as compared to non-treated plants.

Furthermore, the conferring of resistance on treated plants may also be due to the induction of immune-related genes that promote plant immune response, and therefore resistance to pathogens. Such genes may include, for example, and defensin and/or pathogenesis-related genes, or any other immune-related gene. More specifically, at least one of PR1 and PDF1.2 expression may be induced by about 1%-1000%, about 5%-95%, about 10%-90%, about 15%-85%, about 20%-80%, about 25%-75%, about 30%-70%, about 35%-65%, about 40%-60% or about 45%-55% as compared to non-treated plants, or at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% as compared to non-treated plants.

Relative to a disease- or pest-susceptible plant, plant resistance to disease or pest is often defined as reduction of pathogen growth on or in the plant. Thus, a resistant plant will be less adversely affected by said pathogen, or even immune to its detrimental effects, as compared to a susceptible plant. This may be accomplished, for example, by induction of the plant immune genes.

Indeed, in one embodiment, the composition of the invention up-regulates or induces the expression of plant immune-related genes. In more specific embodiments, said plant immune-related genes encode at least one of pathogenesis-related proteins family and defensins family.

Generally, when used, the term "induce expression" or "induction of expression" of genes relates to the induction of an increase of at least one of: transcription rate, translation rate, protein and/or mRNA stability, gene product quantity and protein and/or mRNA maturation. More specifically, when inducing the expression of said gene/s, the increase of at least one of: transcription rate, translation rate, protein and/or mRNA stability, gene product quantity and protein and/or mRNA maturation increases by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% as compared to corresponding rates in control, non-treated (non-induced) organisms.

In a specific embodiment, the member of the pathogenesis-related proteins family may be PR1 and the member of the defensins family may be PDF1.2.

PDF1.2 is also known as LCR77; Low-Molecular-Weight Cysteine-Rich 77; MFC16.8; MFC16_8; PDF1.2; PDF1.2A; Plant Defensin 1.2 and Plant Defensin 1.2A. PDF1.2 encodes an ethylene- and jasmonate-responsive plant defensin, and belongs to the plant defensin (PDF) family with the following members: At1g75830/PDF1.1, At5g44420/PDF1.2a, At2g26020/PDF1.2b, At5g44430/PDF1.2c, At2g26010/PDF1.3, At1g19610/PDF1.4, At1g55010/PDF1.5, At2g02120/PDF2.1, At2g02100/PDF2.2, At2g02130/PDF2.3, At1g61070/PDF2.4, At5g63660/PDF2.5, At2g02140/PDF2.6, At5g38330/PDF3.1 and At4g30070/PDF3.2.

In another specific embodiment, the composition of the invention induces the expression of PR1 in said plant.

PR1 (Pathogenesis-Related Gene 1), is also known as AtPR1; Pathogenesis-Related Gene 1; Pathogenesis-Related Protein 1; PR 1; PR1; T6B13.15 and T6B13_15. PR1 gene expression is induced in response to a variety of pathogens. It is a useful molecular marker for the SAR response. Expression of this gene is salicylic-acid responsive (SAR).

"Pathogenesis-related proteins" (PRs) have been defined as "proteins encoded by the host plant but induced only in pathological or related situations". To be included among the PRs, a protein has to be newly expressed upon infection but not necessarily in all pathological conditions. Pathological situations refer to all types of infected states, not just to resistant, hypersensitive responses in which PRs are most common; they also include parasitic attack by nematodes, insects and herbivores. Induction only by abiotic stress conditions is not a sufficient criterion for inclusion as a PRs. Members of the PR group include, for example: PR 1a, PR 1b, PR 1c, PR 2a, PR 2b, PR 3, PR 4, PR 5a, PR 5b, 16 kD, Gluc.b, Ch.32, Ch.34 and Osmotin.

In yet another specific embodiment, composition of the invention induces the expression of PDF1.2 in said plant.

In a further specific embodiment, the composition of the invention induces the expression of PR1 and PDF1.2 in said plant, optionally said composition induces the expression of at least one additional immune-related gene.

In certain embodiments, such genes include, for example, the *Arabidopsis* genes AtBGL2, AtVSP1, AtThi2.1, AtLox, and their equivalents in other plant species. Still further, these genes may be the tomato genes Protein inhibitor 1 (Pin1) and Pin2.

In specific embodiments, the composition of the invention enhances, increases or induces the expression of plant immune-related genes, thereby increasing plant resistance to pests including at least one of fungal, viral, bacterial, nematode and insect infections or infestations.

In yet another embodiment, the pesticidal compositions and methods of the invention may be applicable for conferring resistance against and/or treating pathologic conditions caused by Nematodes. Non-limiting examples of plant-pathogenic nematodes include: *Ditylenchus dipsaci, Aphelenchoides ritzemabosi, Heterodera* spp., *Heterodera trifolii, Heterodera schachtii, Xiphinema americanum, Pratylenchus* spp., *Pratylenchus vulnus, Pratylenchus neglectus, Pratylenchus penetrans, Longidorus* spp., *Paratylenchus* spp., *Paratylenchus hamatus, Rotylenchulus* spp., *Meloidogyne* spp., *Meloidogyne arenaria, Meloidogyne chitwoodi, Meloidogyne hapla, Meloidogyne incognita, Meloidogyne javanica, Helicotylenchus* spp., *Paratrichodorus* spp., *Tylenchorhynchus* spp., *Belonolaimus longicaudatus, Tylenchulus semipenetrans, Criconemella xenoplax, Helicotylenchus* spp., and *Tylenchorhynchus* spp.

In yet another embodiment, the pesticidal compositions and methods of the invention may be applicable for conferring resistance against and/or treating pathologic conditions caused by insects. Non-limiting examples of plant pest insects who predate upon said plant include: *Acalymma, Acleris variegana*, African armyworm, Africanized bee, Agromyzidae, *Agrotis munda, Agrotis porphyricollis, Aleurocanthus woglumi, Aleyrodes proletella, Anasa tristis, Anisoplia austriaca, Anthonomus pomorum, Anthonomus signatus, Aonidiella aurantii*, Aphid, *Aphis fabae, Aphis gossypii*, Apple maggot, Argentine ant, Army cutworm, *Arotrophora arcuatalis, Asterolecanium coffeae*, Australian plague locust, *Bactericera cockerelli, Bactrocera, Bactrocera correcta, Bagrada hilaris*, Banded hickory borer, Banksia Boring Moth, Beet armyworm, Bogong moth, Boll weevil, *Brevicoryne brassicae*, Brown locust, Brown marmorated stink bug, Brown planthopper, Cabbage Moth, Cabbage worm, *Callosobruchus maculatus*, Cane beetle, Carrot fly, Cecidomyiidae, *Ceratitis capitata*, Cereal leaf beetle, *Chlorops pumilionis*, Citrus long-horned beetle, *Coccus viridis*, Codling moth, Coffee borer beetle, Colorado potato beetle, Confused flour beetle, *Crambus*, Cucumber beetle, *Curculio nucum*, Cutworm, Dark Sword-grass, Date stone beetle, *Delia* (genus), *Delia antiqua, Delia floralis, Delia radicum*, Desert locus, *Diabrotica*, Diamondback moth, *Diaphania indica, Diaphania nitidalis, Diaphorina citri, Diaprepes abbreviatus*, Differential grasshopper, *Dociostaurus maroccanus, Drosophila suzukii, Erionota thrax, Eriosomatinae, Eumetopina flavipes*, European Corn Borer, *Eurydema oleracea, Eurygaster integriceps*, Forest bug, *Frankliniella occidentalis, Frankliniella tritici, Galleria mellonella*, Garden Dart, Greenhouse whitefly, *Gryllotalpa orientalis, Gryllus pennsylvanicus*, Gypsy moths in the United States, *Helicoverpa armigera, Helicoverpa zea, Henosepilachna vigintioctopunctata*, Hessian fly, Japanese beetle, Khapra beetle, *Lampides boeticus*, Large White, Leaf miner, *Lepidiota consobrina, Lepidosaphes ulmi, Leptoglossus zonatus, Leptopterna dolabrata*, Lesser wax moth, *Leucoptera* (moth), *Leucoptera caffeina*, Light brown apple moth, Light brown apple moth controversy, *Lissorhoptrus oryzophilus*, Long-tailed Skipper, *Lygus, Maconellicoccus hirsutus, Macrodac-*

*tylus subspinosus, Macrosiphum euphorbiae,* Maize weevil, *Manduca sexta, Mayetiola hordei,* Mealybug, Moth, Leek moth, *Myzus persicae, Nezara viridula,* Olive fruit fly, Opomyzidae, *Papilio demodocus, Paracoccus marginatus, Paratachardina pseudolobata,* Pea aphid, Pentatomoidea, *Phthorimaea operculella, Phyllophaga* (genus), Phylloxera, Phylloxeroidea, Pink bollworm, *Platynota idaeusalis,* Plum curculio, *Pseudococcus viburni, Pyralis farinalis,* Red imported fire ant, Red locust, *Rhagoletis cerasi, Rhagoletis indifferens, Rhagoletis mendax, Rhynchophorus ferrugineus, Rhyzopertha dominica,* Rice Moth, Russian wheat aphid, San Jose scale, Scale insect, Sciaridae, *Scirtothrips dorsalis,* Scutelleridae, Serpentine leaf miner, Silverleaf whitefly, Small hive beetle, Soybean aphid, *Spodoptera cilium, Spodoptera litura,* Spotted cucumber beetle, Squash vine borer, *Stenotus binotatus, Sternorrhyncha, Strauzia longipennis,* Striped flea beetle, Sunn pest, Sweetpotato bug, Tarnished plant bug, *Thrips, Thrips palmi, Toxoptera citricida, Trioza erytreae, Tuta absoluta,* Varied carpet beetle, *Virachola isocrates,* Waxworm, Western corn rootworm, Wheat weevil, Winter Moth and *Xyleborus glabratus.*

In a particular embodiment, the composition of the invention is effective in preventing, ameliorating, inhibiting, eliminating or delaying the onset of pests infections or infestations, spore germination and hyphae growth in farm and industrial produce. The composition of the invention thereby is efficient in extending the shelf-life or storage time of such produce.

It should be noted that farm and industrial produce include any one of a plant, plant material including roots, bulbs, tubers, corms, leaves, flowers, seeds, stems, callus tissue, nuts, grains, fruit (for example, grapes), cuttings, root stock, scions, harvested crops including roots, bulbs, tubers, corms, leaves, flowers, seeds, stems, callus tissue, nuts, grains, fruit, cuttings, root stock or scions.

Furthermore, it is thus appreciated that the pesticidal composition may be effective in preventing, ameliorating, inhibiting, eliminating or delaying the onset of pests infections or infestations, spore germination and hyphae growth in farm and industrial produce which is not plant material, such as meat and dairy products and any industrial material susceptible to said pests.

The term "shelf life" is defined as the amount of time a product remains acceptable for organoleptic, nutritional, and/or safety purposes, for the consumer or the retailer. The composition of the invention is particularly useful for extending product shelf life, as demonstrated in Example 10, which shows a 50% decrease in decay in grapes treated with said composition as compared to control grapes after 2.5 months in 0° C. and three days in 20° C. The shelf life of industrial and farm products treated with the composition of the invention may be extended by at least 1 day, 2 days, 3 days, 4 days, 5 days, 6 days, 7 days, 8 days, 9 days, 10 days, 15 days, 20 days, 25 days, 30 days, two months, three months, four months, five months, six month, a year, two years, five years, ten years or even more.

In the protection of materials, the composition according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by the composition according to the invention from microbial, fungal, viral or insect change or destruction can be adhesives, sizes, paper and board, textiles, leather, wood, paints and plastic articles, cooling lubricants and other materials which can be infected with, or destroyed by, such pests. Parts of production plants, for example cooling-water circuits, which may be impaired by the proliferation of microorganisms, may also be mentioned within the scope of the materials to be protected.

It should be appreciated that in certain embodiments, the composition of the invention may further comprise an agriculturally acceptable carrier. The term "agriculturally acceptable carrier" intended to include any material that facilitates application of a composition of the invention to the intended subject, which may for example be a Plant, plant material or equipment, or that facilitates storage, transport or handling. Carriers used in compositions for application to plants and plant material are preferably non-phytotoxic or only mildly phytotoxic. A suitable carrier may be a solid, liquid or gas depending on the desired formulation. In one embodiment preferred carriers include polar liquid carriers such as water, mineral oils and vegetable oils.

As used herein, the term "subject" is intended to include any target surface to which a compound or composition of the invention may be applied, for example to a plant, plant material including roots, bulbs, tubers, corms, leaves, flowers, seeds, stems, callus tissue, nuts, grains, fruit, cuttings, root stock, scions, harvested crops including roots, bulbs, tubers, corms, leaves, flowers, seeds, stems, callus tissue, nuts, grains, fruit, cuttings, root stock, scions, or any surface that may contact harvested crops including harvesting equipment, packaging equipment and packaging material.

Compositions used as such for agricultural and industrial purposes, as well as compositions for promoting growth in plant as described below are commonly formulated accordingly. The antimicrobial, antifungal, pesticidal and plant growth-promoting compositions according to the invention may be formed using the active ingredients as described herein in an inert carrier. If formulated as a solid, the ingredients may be mixed with such typical carriers as Fuller's earth, kaolin clays, silicas or other wettable inorganic diluents. Free-flowing dusts formulations may also be utilized by combining the dry active ingredients with finely divided solids such as talc, kieselguhr, pyrophyllite, clays, diatomaceous earth and the like.

The powders may also be applied as a suspension or solution, depending on the solubility in the liquid carrier. Pressurized sprays, typically aerosols with the active ingredient dispersed in a low-boiling dispersant solvent carrier may be used. Percentages of weight may vary according to the manner in which the composition is to be applied and formulation used. In general, the active ingredient will comprise 0.005% to 95% of the active ingredient by weight in the antimicrobial composition. The biocontrol composition may be applied with other ingredients including growth regulators, insecticides, herbicides, fertilizers and the like. Formulation of the active ingredients to assist applicability, ease, handling, maintain chemical stability and increase effectiveness may require addition of various materials. Solvents may be chosen on the basis of affecting the solubility of the active ingredient, fire hazard, and flash point, emulsifiability, specific gravity and economic considerations.

According to another embodiment of the present invention, any adjuvant may be added to enhance the active ingredients and can include surfactants which are anionic, cationic or nonionic. Stabilizers and antifreeze compounds will prolong storage. Additionally, synergists, stickers, spreaders and deodorant compounds can be added to improve the handling characteristics of the commercial formulation.

The inventive pesticidal composition of the present invention may be employed also as antimicrobial agents useful in inhibiting the growth of microorganisms present or eradicating microorganisms on a surface or in a medium outside a living host. The inventive compositions may be employed, for example, as disinfectants for a variety of solid and liquid media susceptible to microbial growth. Suitable amounts of the inventive composition may be determined by methods known to the skilled artisan.

The compositions may be prepared in any known manner, e.g. by supplementing the active ingredient with agriculturally acceptable carriers, auxiliaries or diluents, such as solvents, emulsifiers and dispersants or surfactants.

Solvents suitable for use in the invention and its various products include, but are not limited to, aromatics, e.g. xylene; chlorinated aromatics, e.g. chlorobenzenes; paraffins, e.g. mineral oil fractions; alcohols, e.g. methanol and butanol; ketones, e.g. cyclohexanone; amines, e.g. ethanolamine and dimethylformamide; and water, preferably deionized. When water is used, other organic solvents may also be used as co-solvents.

Carriers suitable for use in the compositions of the invention and its products include, but are not limited to, ground natural or synthetic minerals, e.g. kaolins, clays, talc, chalk, silica, silicates, and the like.

Emulsifiers suitable for use in the compositions of the invention include, but are not limited to, nonionic and anionic emulsifiers, e.g. polyoxyethylene fatty alcohol ethers, alkylsulfonates, arylsulfonates, and the like.

Dispersants suitable for use in the compositions of the invention include, but are not limited to, lignosulfite waste liquors and methylcellulose; and the like.

Suitable surfactants include, but are not limited to, lignophenol-, naphthalene- and dibutylnaphthalenesulfonic acid, fatty acids, alkyl- and alkylarylsulfonates, alkyl lauryl ether and fatty alcohol sulfates, salts of sulfated hexa-, hepta- and octadecanols and of fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated iso-octyl-, octyl- or nonylphenol, alkylphenol polyglycol ethers, tributylphenyl polyglycol ether, alkylauryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

For the purpose of application, the compositions of the invention in the form of suspension can be used directly or formulated as compositions suitable for spraying, atomizing, dusting, spreading or pouring. For instance, the compositions can be formulated as ready-to-spray solutions, powders, suspensions, highly concentrated aqueous, oily or other suspensions or dispersions, emulsions, oil dispersions, pastes, dusts, or granules.

The non-toxic aqueous compositions may also contain various additives such as antioxidants, preservatives, pH neutralizers and/or clarifiers.

In use, the non-toxic aqueous compositions are diluted and sprayed or misted on the infested host. In some cases, repeated applications may be required.

To enhance the efficiency of the application, the pesticidal, specifically, fungicidal/bactericidal/antiviral and plant growth-promoting compositions of the invention may also comprise other active ingredients, such as herbicides, insecticides, growth stimulators, fertilizers and the like.

Additionally, the liquid form of the compositions can be placed on or embedded in a wipe, said wipe preferably being made of paper or cloth, or provided as a cleaning reagent for use in sanitation.

The compositions according to the invention are also suitable for increasing the yield of crops. Moreover, it has reduced toxicity and is tolerated well by plants.

The fact that the composition is well tolerated by plants at the concentrations required for controlling plant diseases, as shown in Example 6, permits the treatment of above-ground parts of plants, of propagation stock and seeds, and of the soil.

Assessment of a composition of the invention or a composition of the invention including or delivered with an additional agricultural agent such as an additional fungicide may include assessment of:

(1) Degree of control of target microbes without stimulating growth of undesirable non-target microbes or harming beneficial organisms.
(2) Durability of control.
(3) Degree of phytotoxicity and effects on plant development when used repeatedly throughout a portion or the entirety of a growing season.
(4) Compatibility with other control products used in the industry.

In one embodiment, a composition of the invention is mildly phyto-toxic and preferably the composition is not phyto-toxic.

As used herein, the term "mildly phyto-toxic" is intended to mean that the level of phyto-toxicity does not substantially effect plant yield or quality and preferably means that a composition of the invention may cause small blemishes (5-15 $mm^2$) on plant leaves, and may cause necrotic or chlorotic patches (>15 $mm^2$) and leaf distortion, but preferably should not kill more than 30%, preferably not more than 20% of a leaf on a plant to which a composition of the invention is applied. The term "plant yield" is intended to refer to the product yield of a plant or population of plants. In one embodiment the yield may be the yield of a product including but not limited to one or more of whole plants or plant parts such as roots, bulbs, corms, tubers, leaves, cuttings, flowers, stems, fruits and seeds or other propagative material.

In the third aspect, the invention provides a composition for promoting growth in plant. The composition of the invention comprises as an active ingredient a biocontrol agent comprising at least one of:

a. *Pseudozyma aphidis* cells or any isolate or mutant thereof;
b. *Pseudozyma aphidis* spores;
c. conditioned culture medium of *Pseudozyma aphidis;*
d. secreted compounds from *Pseudozyma aphidis;*
e. any extracts or preparations of any of (a) to (d); and
f. a combination of at least two of the biocontrol agents defined in (a) to (e); said composition optionally further comprises carriers diluents and excipients.

The term "promoting growth" refers to the fact that the mass of at least one plant part is significantly larger in a plant treated with the composition as compared to a control untreated plant after sufficient time in treatment.

More specifically, according to one embodiment, the composition induces an increase in at least one of: plant weight, plant height, number of plant leaves, root system, plant thickness and plant biomass.

It is appreciated that the composition may promote plant growth in various plant parts. The term "plant parts" as referred to herein is directed to any one of leaf disks, roots, stems, shoots, leaves, pollen, seeds, embryos, cotyledons, hypocotyls, megagametophytes, callus tissue, meristematic tissue and various forms of cells and culture such as single cells, protoplast, embryos, and callus tissue. The plant tissue may be in plants or in organ, tissue or cell culture.

In one embodiment, the part with increased mass is a part that contributes to the plant commercial yield (fruits, grains, roots, flower and leaves).

It should be appreciated that the composition of the invention may increase the thickness, biomass and rigidity of woody plants and therefore may be applicable in the paper industry.

Specifically, the plant growth enhancing composition may increase plant height by between about 1% to about 99.9%, more specifically, at least about 1%, about 3%, about 5%, about 7%, about 9%, about 11%, about 13%, about 15%, about 17%, about 19%, about 20%, about 21%, about 23%, about 25%, about 27%, about 29%, about 30%, about 31%, about 33%, about 35%, about 37%, about 39%, about 41%, about 43%, about 45%, about 47%, about 49%, about 51%, about 53%, about 55%, about 57% or about 60%. More specifically, the treatments may increase plant height by at least about 15% to about 25%.

Furthermore, the composition may increase plant weight by between about 1% to about 99.9%, more specifically, at least about 1%, about 3%, about 5%, about 7%, about 9%, about 11%, about 13%, about 15%, about 17%, about 19%, about 21%, about 23%, about 25%, about 27%, about 29%, about 30%, about 31%, about 33%, about 35%, about 37%, about 39%, about 41%, about 43%, about 45%, about 47%, about 49%, about 51%, about 53%, about 55%, about 57% or about 60%. More specifically, the treatments may increase plant weight by at least about 25% to about 35%.

With respect to the number of leaves per plant, the composition may increase said number by between about 1% to about 99.9%, more specifically, at least about 1%, about 3%, about 5%, about 7%, about 9%, about 11%, about 13%, about 15%, about 17%, about 19%, about 20%, about 21%, about 23%, about 24%, about 25%, about 26%, about 27%, about 29%, about 30%, about 31%, about 33%, about 35%, about 37%, about 39%, about 41%, about 43%, about 45%, about 47%, about 49%, about 51%, about 53%, about 55%, about 57% or about 60%. More specifically, the treatments may increase plant leaf number by at least about 20% to about 30%.

Examples of such enhancements may be found in Example 11 and FIGS. 11A-11C.

The composition may also enhance the plant root system, as manifested in an increase in the weight of the underground parts of said plant. In some embodiments, the weight of the underground parts of said plant increases between about 1% to about 99.9%, more specifically, at least about 1%, about 3%, about 5%, about 7%, about 9%, about 11%, about 13%, about 15%, about 17%, about 19%, about 20%, about 21%, about 23%, about 24%, about 25%, about 26%, about 27%, about 29%, about 30%, about 31%, about 33%, about 35%, about 37%, about 39%, about 41%, about 43%, about 45%, about 47%, about 49%, about 51%, about 53%, about 55%, about 57% or about 60%.

The composition may also increase the plant stalk thickness. In some embodiments, the thickness of the stalk of said plant increases between about 1% to about 99.9%, more specifically, at least about 1%, about 3%, about 5%, about 7%, about 9%, about 11%, about 13%, about 15%, about 17%, about 19%, about 20%, about 21%, about 23%, about 24%, about 25%, about 26%, about 27%, about 29%, about 30%, about 31%, about 33%, about 35%, about 37%, about 39%, about 41%, about 43%, about 45%, about 47%, about 49%, about 51%, about 53%, about 55%, about 57% n about 60%, about 70%, about 80%, about 90% or about 100%.

Furthermore, the composition of the invention also renders the plant more wooden (upright), as reflected by a decrease in the angle between the plant and an upright line (perpendicular to the ground). This decrease may be of at least about 0.1°, about 0.2°, about 0.4°, about 0.8°, about 1.0°, about 2.0°, about 3.0°, about 4.0°, about 5.0°, about 6.0°, about 8.0°, about 10°, about 12°, about 14°, about 16°, about 18°, about 20°, about 22°, about 24°, about 28°, about 30° or about 35°.

The composition may increase the plant biomass by between about 1% to about 99.9%, more specifically, by at least about 1%, about 3%, about 5%, about 7%, about 9%, about 11%, about 13%, about 15%, about 17%, about 19%, about 20%, about 21%, about 23%, about 24%, about 25%, about 26%, about 27%, about 29%, about 30%, about 31%, about 33%, about 35%, about 37%, about 39%, about 41%, about 43%, about 45%, about 47%, about 49%, about 51%, about 53%, about 55%, about 57% or about 60%.

In another embodiment, the compositions of the invention may further comprise an additional agricultural agent selected from the group consisting of: herbicide, insecticide, growth stimulator, and fertilizer.

A herbicide, also known as a weedkiller, is a type of pesticide used to kill unwanted plants. Selective herbicides kill specific targets while leaving the desired crop relatively unharmed. Some of these act by interfering with the growth of the weed and are often synthetic imitations of plant hormones. Herbicides used to clear waste ground, industrial sites, railways and railway embankments are non-selective and kill all plant material with which they come into contact. Smaller quantities are used in forestry, pasture systems, and management of areas set aside as wildlife habitat.

Herbicides can be grouped by activity, use, chemical family, mode of action, or type of vegetation controlled.

By activity, herbicides may be contact herbicides which destroy only the plant tissue in contact with the chemical, or systemic herbicides which are translocated through the plant, either from foliar application down to the roots, or from soil application up to the leaves.

By use, herbicides may be pre-plant incorporated, i.e. they are soil applied prior to planting and mechanically incorporated into the soil. The objective for incorporation is to prevent dissipation through photodecomposition and/or volatility. They may be preemergent herbicides, which are applied to the soil before the crop emerges and prevent germination or early growth of weed seeds, or they may be post-emergent herbicides which are applied after the crop has emerged.

Their classification by mechanism of action (MOA) indicates the first enzyme, protein, or biochemical step affected in the plant following application. The main mechanisms of action are:

ACCase inhibitors are compounds that kill grasses. Acetyl coenzyme A carboxylase (ACCase) is part of the first step of lipid synthesis. Thus, ACCase inhibitors affect cell membrane production in the meristems of the grass plant. The ACCases of grasses are sensitive to these herbicides, whereas the ACCases of dicot plants are not.

ALS inhibitors: the acetolactate synthase (ALS) enzyme (also known as acetohydroxyacid synthase, or AHAS) is the first step in the synthesis of the branched-chain amino acids (valine, leucine, and isoleucine). These herbicides slowly starve affected plants of these amino acids which eventually leads to inhibition of DNA synthesis. They affect grasses and dicots alike. The ALS inhibitor family includes sulfonylureas (SUs), imidazolinones (IMIs), triazolopyrimidines (TPs), pyrimidinyl oxybenzoates (POBs), and sulfonylamino carbonyl triazolinones (SCTs). ALS is a biological pathway that exists only in plants and not in animals thus making the ALS-inhibitors among the safest herbicides.

EPSPS inhibitors: The enolpyruvylshikimate 3-phosphate synthase enzyme EPSPS is used in the synthesis of the amino acids tryptophan, phenylalanine and tyrosine. They affect grasses and dicots alike. Glyphosate (Roundup) is a systemic EPSPS inhibitor but inactivated by soil contact.

Synthetic auxin inaugurated the era of organic herbicides. They were discovered in the 1940s after a long study of the plant growth regulator auxin. Synthetic auxins mimic this plant hormone. They have several points of action on the cell membrane, and are effective in the control of dicot plants. 2,4-D is a synthetic auxin herbicide.

Photosystem II inhibitors reduce electron flow from water to NADPH2+ at the photochemical step in photosynthesis. They bind to the Qb site on the D1 protein, and prevent quinone from binding to this site. Therefore, this group of compounds cause electrons to accumulate on chlorophyll molecules. As a consequence, oxidation reactions in excess of those normally tolerated by the cell occur, and the plant dies. The triazine herbicides (including atrazine) and urea derivatives (diuron) are photosystem II inhibitors, Photosystem I inhibitors steal electrons from the normal pathway through FeS-Fdx-NADP leading to direct discharge of electrons on Oxygen. As result ROS (reactive oxygen species) are produced and oxidation reactions in excess of those normally tolerated by the cell occur leading to plant death.

Examples of herbicides include, but are not limited to: tralkoxydim, quizalofop, diclofop, clodinafop, sethoxydim, fenoxyprop, clethodim, difenzoquat, triallate, pendimethalin, trifluralin, ethalfluralin, imazamethabenz, sulfesulfuron, flucarbazone, metsulfuron, triasulfuron, tribenuron, chlorsulfuron, thifensulfuron, prosulfuron, imazapic, imazathapyr. Imazamox, glyphosate, sulfosate, paraquat, dicamba, clopyralid 2,4-D, quinclorac, fluoxypyr, clopyralid, picloram, pyridate and bromoxynil.

In yet another embodiment, as an additional active agent, the compositions of the invention may further comprise an insecticide.

An insecticide is a pesticide used against insects. They include ovicides and larvicides used against the eggs and larvae of insects, respectively. Insecticides are used in agriculture, medicine, industry and the household. The use of insecticides is believed to be one of the major factors behind the increase in agricultural productivity in the 20th century.

Systemic insecticides are incorporated by treated plants. Insects ingest the insecticide while feeding on the plants.

Contact insecticides are toxic to insects brought into direct contact. Efficacy is often related to the quality of pesticide application, with small droplets (such as aerosols) often improving performance.

Natural insecticides, such as nicotine, pyrethrum and neem extracts are made by plants as defenses against insects. Nicotine based insecticides have been barred in the U.S. since 2001 to prevent residues from contaminating foods.

Plant-Incorporated Protectants (PIP) are insecticidal substances produced by plants after genetic modification. For instance, a gene that codes for a specific Baccilus thuringiensis biocidal protein is introduced into a crop plant's genetic material. Then, the plant manufactures the protein. Since the biocide is incorporated into the plant, additional applications at least of the same compound, are not required.

Inorganic insecticides are manufactured with metals and include arsenates, copper compounds and fluorine compounds, which are now seldom used, and sulfur, which is commonly used.

Organic insecticides are synthetic chemicals which comprise the largest numbers of pesticides available for use today.

Examples of insecticides include, but are not limited to: (E)-7-dodecenyl acetate/(E)-8-dodecenyl acetate/(Z)-8-dodecenyl acetate, (E,E)-8,10 dodecadien-1-ol, 1,3 dichloropropene, 3(S) methyl-6-isopropenyl-9-docadien-1yl acetate, abamectin, acephate, acetamiprid, aldicarb, *Allium sativum*, alpha cypermethrin, aluminium phosphide, amitraz, azadirachtin, azinphos methyl, *Bacillus thuringiensis* subsp *israelensis, Bacillus thuringiensis* var *aiziwai kurstaki, Beauveria bassiana*, benfuracarb, beta-cyfluthrin, beta-cypermethrin, bifenthin/myclobutanil, bifenthrin, borax, *Bradyrhizobium japonicum*, brodifacoum, bromopropylate, buprofenzin, cadusafos, canola oil/garlic extract/pyrethrum, carbaryl, carbofuran, carbon dioxide/ethylene oxide, carbosulfan, cartap hydrochloride, chlorphenapyr, Chlorpyrifos, citronella oil, clofentezine, codlimone (E,E-8,10-dodecadiene-1-ol), codlimone [(E,E)-8,10 dodecadiene-7-ol], copper, copper oxychloride/sulfur, coumatetralyl, *Cryptophlebia leucotreta*, cyanophos, cyfluthrin, cyhexatin, cypermethrin, cyromazine, d-allethrin, dazomet, deltamethrin, demeton-S-methyl, diazinon, dichlorvos, dicofol, difenacoum, diflubenzuron, dimethoate, Dimilin, disulfoton, d-phenothrin/tetramethrin, E,E-8,10-dodecadien-1-ol/dodecadienol/tetradecadenol, E,E-8,10 dodecadien-1-ol, EDB, emamectin, endosulfan, esfenvalerate, ethoprophos, ethylene dibromide, etoxazole, fenamiphos, fenazaquin, fenbutatin, fenitrohion, fenoxycarb, fenpyroximate, fenthion, fenvalerate, ferric sodium EDTA, fipronil, flufenoxuron, flumethrin, formetanate, fosthiazate, fumagillin, furfural, gamma-BHC, gamma-cyhalothrin, garlic extract, hydramethylnon, imidacloprid, lambda-cyhalothrin, lavandulyl senecioate, lufenuron, magnesium phosphide, mancozeb, maple lactone, mercaptothion, metaldehyde, metam-sodium, *Metarhizium anisopliae* var *acridium* isolate IMI 330 189, metham-sodium, methamidophos, methidathion, methidathion, methiocarb, methomyl, methyl bromide, mevinphos, milbemectin, mineral oil, novaluron, omethoate, ortho-phenylphenol, oxamyl, oxydemeton-methyl, *Paecilomyces lilacinus* strain 251, parathion, permethrin, phenothoate, phorate, pirimicarb, polysulphide sulphur, potassium salts of fatty acids, profenofos, propargite, prothiofos, pyrethrins, pyriproxyfen, quinalphos, rape oil, *Rhizobium leguminosarum* biovar phaseoli, rotenone, sodium fluosilicate, Spinosad, spirodiclofen, sulfur, tartar emetic, tau-fluvalinate, tebufenozide, temephos, terbufos, tetrachlorvinphos, tetradecenyl acetate, tetradifon, thiacloprid, thiamethoxam, thiodicarb, thiram, trichlorfon, *Trichoderma harzianum*, triflumuron, trimedlure, Z-8 dodecen-1-yl acetate/E-8 dodecen-1-yl acetate/Z-8 dodecen-1-ol and zinc phosphide.

Still further, as an additional active agent, the compositions of the invention may further comprise growth stimulators. The term "growth stimulators", or "plant growth stimulators" as used herein, relates to substances that induce an increase in at least one of: plant biomass, root system bifurcations and length, plant weight, number of leaves, stalk thickness, plant height and number of flowers and/or fruit. Said stimulators may be of biologic, organic or inorganic origin and may be solid or liquid. Non-limiting examples of such stimulators include: Bov-A-MuraC© (sprayable soluble manure), FeRROMEC®, Launch® Biostimulant (contains plant hormones from cold-water kelp extract along with humic and fulvic acids), Solu-Cal® (ground pelletized calcium carbonate (38%) impregnated with a proprietary organic acid), Viga-ROOT™ Stimulator (dry-soluble combination of chelated iron, chelated manganese, chelated zinc, natural humic substance, seaweed extract, yucca and a proprietary blend of natural sugars, vitamins, amino acids and beneficial bacteria), Sprint® 330 FE Iron (10% fully chelated DTPA iron).

The compositions of the invention may further comprise fertilizers. The term "fertilizer" relates to any organic or inorganic material of natural or synthetic origin (other than liming materials) that is added to a soil to supply one or more plant nutrients essential to the growth of plants. A recent assessment found that about 40 to 60% of crop yields are attributable to commercial fertilizer use.

Mined inorganic fertilizers have been used for many centuries, whereas chemically synthesized inorganic fertilizers were only widely developed during the industrial revolution. Inorganic fertilizer use has also significantly supported global population growth—it has been estimated that almost half the people on the Earth are currently fed as a result of synthetic nitrogen fertilizer use. Organic fertilizers include naturally occurring organic materials, (e.g. manure, worm castings, compost, seaweed, guano), or naturally occurring mineral deposits (e.g. saltpeter).

Fertilizers typically provide, in varying proportions:
Six macronutrients: nitrogen (N), phosphorus (P), potassium (K), calcium (Ca), magnesium (Mg), and sulfur (S); and six micronutrients: boron (B), chlorine (Cl), copper (Cu), iron (Fe), manganese (Mn), molybdenum (Mo), and zinc (Zn).

Non-limiting examples for fertilizers include: Ammonium Nitrate 33.5% N, Ammonium 21% N, Ammonium Sulfate Nitrate 26% N, Calcium Ammonium Nitrate (CAN) 27%, Calcium Nitrate 15.5% N, Sodium Nitrate (Natural Chilesalpeter) 16% N, Urea 46% N, Low Biuret Urea, Basic Slag 10% P205, Rock Phosphate 30/32% P205, Single Super phosphate 18/20% P205 (powder/granular), Triple Super phosphate 46% P205 granular 43% (water soluble), Muriate of Potash 60% K20, Sulphate of Potash 48/52% K20, Diammonium Phosphate (DAP) 18-46-0, Mono Ammonium Phosphate (MAP)12-52-0, Alfalfa meal, bat and bird guano, bloodmeal, bonemeal, chicken manure, fish meal, seaweed (liquid), worm castings/vermicompost, cottonseed meal and others.

In another aspect, the invention relates to a method of treating, preventing, ameliorating, inhibiting, eliminating or delaying the onset of bacterial, fungal or pest infestation in a plant or a plant material. The method of the invention comprises the step of applying onto a plant, to a plant material or in the vicinity of the treated plant or plant material a biocontrol agent or a composition comprising the same. In a specific embodiment, the biocontrol agent comprising at least one of:
a. *Pseudozyma aphidis* cells or any isolate or mutant thereof;
b. *Pseudozyma aphidis* spores;
c. conditioned culture medium of *Pseudozyma aphidis;*
d. secreted compounds from *Pseudozyma aphidis;*
e. any extracts or preparations of any of (a) to (d); and
f. a combination of at least two of the biocontrol agents defined in (a) to (e).

It should be appreciated that the method of the invention is applicable in treating and preventing infection or infestation of any plant pathogen and any pathologic condition causes thereby.

As used herein, the term "disease" or "condition" refers to a state in which there is a disturbance of normal functioning. A "disease" is any abnormal condition of the plant that causes dysfunction or damages said plant taste, fragrance, appearance or texture. It should be noted that the terms "disease", "disorder" and "condition" are equally used herein. In specific cases, a disease is caused by pathogens, including bacteria, fungi, viruses, nematodes, insects or other pests.

The terms "prevention" or "prophylaxis" as used herein refer to prevention of the emergence of a plant pathology, either symptomatic or not. As such, the methods of the invention may be employed to prevent deleterious plant-pathogen mediated conditions from occurring, and may therefore be used to improve or stabilise health of any plant. Application of the biocontrol agent of the invention or any composition thereof, to the plant, or any plant part, tissue or cell culture, in order to prevent a bacterial, fungal, viral, insect, nematode, or any other pest infection or infestation, or to treat established one, may be single or multiple, and may take place over an extended period of time. For example, in one embodiment of a method of the invention, the biocontrol agent of the invention or any composition thereof may be applied at least about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, 90, 120, 150 or 180 days. In another embodiment the biocontrol agent or a composition thereof may be applied about every 1 to about every 7 days, about every 1 to about every 14 days, about every 1 to about every 21 days, about every 1 to about every 28 days or about every 1 to about every 35 days. In one embodiment the biocontrol agent or a composition thereof may be applied about every 1 to about every 30 days, about every 1 to about every 60 days or about every 1 to about every 90 days. In another embodiment the biocontrol agent or a composition thereof may be applied about every 1 to about every 7 days, about every 7 to about every 14 days, about every 14 to about every 21 days, about every 21 to about every 28 days or about every 28 to about every 35 days.

In fact, the biocontrol agent or a composition thereof may be applied periodically for the duration of the plant life, or even applied to the vicinity of the plant periodically beyond the life cycle of the treated plant.

The biocontrol agent of the invention or any composition thereof is applied onto a plant or a plant material. It is noted that the term "plant material" used herein encompasses roots, bulbs, tubers, corms, leaves, flowers, seeds, stems, callus tissue, nuts, grains, fruit, cuttings, root stock, scions, harvested crops including roots, bulbs, tubers, corms, leaves, flowers, seeds, stems, callus tissue, nuts, grains, fruit, cuttings, root stock, scions, or any surface that may contact harvested crops including harvesting equipment, packaging equipment and packaging material.

In other embodiments, the biocontrol agent of the invention or any composition thereof may be applied in the vicinity of the treated plant or plant material. The expression "vicinity of the treated plant or plant material" relates to the perimeter surrounding said plant or plant material onto which the composition according to the invention may be applied in order to treat or prevent plant, or plant material infection or infestation. Therefore, it is understood that the "vicinity of said plant or plant material" encompasses all objects present within a range of up to at least about 1 cm, 2 cm, 3 cm, 4 cm, 5 cm, 6 cm, 7 cm, 8 m, 9 m, 10 cm, 20 cm, 30 cm, 40 cm, 50 cm, 60 cm, 70 cm, 80 cm, 90 cm, 1 m, 2 m, 3 m, 4 m, 5 m, 6 m, 7 m, 8 m, 9 m, 10 m, 11 m, 12 m, 13 m, 14 m, 15 m, 16 m, 17, m 18 m, 19 m, 20 m, 30 m, 40 m or even 50 m of said plant or plant material. The term "vicinity of said plant or plant material" also relates to objects to which the composition of the invention is applied to prior to their placement in said range of the treated plant or plant material. For example, a fertilizer or any other supplement may be augmented with the composition of the invention prior to its application to said plant.

It is appreciated that the compositions of the invention are particularly suited for the treatment and prophylaxis of plant diseases, and thus may be useful for protecting crops and other commercially-important plants, or any other plants.

In one embodiment, the method of the invention is for treating, inhibiting, eliminating or delaying the onset of bacterial infections or infestations.

It is understood that said bacterial infections may be caused by at least one of: *Clavibacter michiganensis, Agrobacterium*

*tumefaciens, Erwinia amylovora, Pseudomonas syringae* pv. *lachrymans, Pseudomonas syringae* pv. *tomato, Streptomyces scabies, Xanthomonas campestris* pv. *campestris* and *Xanthomonas capestris* pv. *vesicatoria*.

Non-limiting examples of plant bacterial diseases and their instigators include: Bacterial leaf spot (*Xanthomonas campestris* pv. *alfalfae*); Bacterial sprout rot (*Erwinia chrysanthemi* pv. *chrysanthemi*); Bacterial wilt (*Clavibacter michiganensis* subsp. *insidiosus*); Crown gall (*Agrobacterium tumefaciens*); Crown and root rot complex (*Pseudomonas viridiflava*); Dwarf (*Xylella fastidiosa*); Syringae leaf spot (*Pseudomonas syringae* pv. *syringae*); Bacterial canker (*Clavibacter michiganensis* subsp. *michiganensis*); and Bacterial wilt (*Ralstonia solanacearum*).

In one specific embodiment, the method of the invention may be used for the treatment *Clavibacter michiganensis* associated pathologic conditions, for example, of bacterial canker of tomato.

In yet another specific embodiment, the method of the invention may be used for the treatment of crown gall disease (the formation of tumors) in over 140 species of dicot, specifically, a disease caused by *Agrobacterium tumefaciens*.

Another embodiment relates to the method of the invention for treating Fire blight caused by *Erwinia amylovora*. Fire blight is a contagious disease affecting apples, pears, and some other members of the family Rosaceae. It is a serious concern to producers of apples and pears. Under optimal conditions, it can destroy an entire orchard in a single growing season.

Still further, the method of the invention may be applicable for treating *Pseudomonas syringae* associated pathologic conditions, for example, the production of Ina proteins by said pathogen, cause water to freeze at fairly high temperatures, resulting in injury to plants.

In another embodiment, the method of the invention is applicable in treating *Streptomyces scabies* associated pathologic conditions, for example scab symptoms on potatoes and other root crops.

In another embodiment, the method of the invention may be applicable for treating plant diseases caused by *Xanthomonas campestris*. More specifically, symptoms of said diseases include marginal leaf chlorosis and darkening of vascular tissue, accompanied by extensive wilting and necrosis. Full leaf yellowing, wilting, and necrosis occur as the disease advances.

In more specific embodiments, the method may be applicable for treating, inhibiting, eliminating or delaying the onset of fungal infections.

In such embodiments, the fungal infections may be caused by at least one of: *Botrytis cinerea, Penicillium digitatum, Alternaria brassicicola, Uromyces appendiculatus, Leveillula taurica, Sclerotinia sclerotiorum* and *Puccinia coronate*.

Non-limiting examples of plant fungal diseases and their instigators include:

Acrocalymma root and crown rot (*Acrocalymma medicaginis, Massarina walkeri*); Anthracnose (*Colletotrichum trifolii*); Aphanomyces root rot (*Aphanomyces euteiches*); Black patch (*Rhizoctonia leguminicola*); Black root rot (*Thielaviopsis basicola, Chalara elegans*); Blossom blight (*Botrytis cinerea, Botryotinia fuckeliana, Sclerotinia sclerotiorum*); Brown root rot (*Phoma sclerotioides*); Crown and root rot complex (*Fusarium acuminatum, Gibberella acuminata, Fusarium avenaceum, Gibberella avenacea, Fusarium equiseti, Fusarium oxysporum, Fusarium sambucinum, Fusarium solani, Nectria haematococca, Fusarium* spp., *Phoma medicaginis, Pythium* spp., *Rhizoctonia solani, Thanatephorus cucumeris, Thielaviopsis basicola, Chalara elegans*); Charcoal rot (*Macrophomina phaseolina*); Common leaf spot (*Pseudopeziza medicaginis*); Corky root rot (*Xylaria* sp.); Crown wart (*Physoderma alfalfae*); Cylindrocarpon root rot (*Cylindrocarpon magnusianum, Nectria ramulariae*); Cylindrocladium root and crown rot (*Cylindrocladium crotalariae, Calonectria crotalariae*); Damping-off (*Fusarium acuminatum, Gibberella acuminata, Mycoleptodiscus terrestris, Phytophthora medicaginis, Phytophthora megasperma* f.sp. *medicaginis, Pythium* spp., *Pythium debaryanum, Pythium irregulare, Pythium splendens, Pythium ultimum, Rhizoctonia solani, Thanatephorus cucumeris*); Downy mildew (*Peronospora trifoliorum*); Fusarium wilt (*Fusarium oxysporum* f.sp. *medicaginis*); Lepto leaf spot (*Leptosphaerulina trifolii*); Marasmius root rot (*Marasmius* sp.); Mycoleptodiscus crown and root rot (*Mycoleptodiscus terrestris*); Myrothecium root rot (*Myrothecium roridum, Myrothecium verrucaria*); Phymatotrichum root rot (*Phymatotrichopsis omnivore*), Phytophthora root rot (*Phytophthora medicaginis, Phytophthora megasperma* f.sp. *medicaginis*); Powdery mildew (*Erysiphe pisi, Leveillula taurica*); Rhizoctonia root rot and stem blight (*Rhizoctonia solani, Thanatephorus cucumeris*); Rhizopus sprout rot (*Rhizopus stolonifer*); Rust (*Uromyces striatus*); Sclerotinia crown and stem rot (*Sclerotinia trifoliorum, Sclerotinia sclerotiorum*); Southern blight (*Sclerotium rolfsii, Athelia rolfsii*); Spring black stem and leaf spot (*Phoma medicaginis*); Stagonospora leaf spot and root rot (*Stagonospora meliloti, Phoma meliloti, Leptosphaeria pratensis*); Stemphylium leaf spot (*Pleospora* spp., *Stemphylium alfalfae, Pleospora alfalfae, Stemphylium botryosum, Pleospora tarda, Stemphylium globuliferum, Stemphylium herbarum, Pleospora herbarum, Stemphylium vesicarium* species complex); Summer black stem and leaf spot (*Cercospora medicaginis*); Verticillium wilt (*Verticillium albo-atrum, Verticillium dahliae*); Violet root rot (*Helicobasidium brebissonii, Rhizoctonia crocorum*); Winter crown rot (*Coprinus psychromorbidus*); Black shoulder (*Alternaria alternate*); and Yellow leaf blotch (*Leptotrochila medicaginis, Sporonema phacidioides*).

According to one embodiment, the method of the invention is applicable in treating *Botrytis cinerea* associated pathogenic conditions. For example, this fungus gives rise to two different kinds of infections on grapes, the first, grey rot, is the result of consistently wet or humid conditions, and typically results in the loss of the affected bunches. The second, noble rot, occurs when drier conditions follow wetter, and can result in distinctive sweet dessert wines, such as Sauternes or the Aszú of Tokaji. *Botrytis cinerea* affects many other plants. It is economically important on soft fruits such as strawberries and bulb crops.

According to another embodiment, the method of the invention may be suitable for treating fungal spoilage in fruits and vegetables and any other pathologic condition caused by *Penicillium italicum, Penicillium digitatum, Penicillium expansum*. For example, slimy rot and production of blue-green conidia and production of mycotoxins (for example, *P. expansum* produces one called patulin).

According to another embodiment, the method of the invention may be useful for treating black spot disease (also called dark leaf spot) on virtually every important cultivated *Brassica* species including broccoli, cabbage, canola, and mustard, and any other pathogenic condition caused by the genus *Alternaria*.

Still further, the method of the present invention may be applicable for treating common bean rust disease caused by the basidiomycete fungus *Uromyces appendiculatus* (Pers.: Pers.) Unger.

In yet another embodiment, the method of the invention may be used for treating Tomato Powdery Mildew caused by the fungus *Leveillula taurica*.

Another embodiment relates to the method of the invention for treating white mold caused by *Sclerotinia sclerotiorum*.

According to certain embodiments, the method of the invention may be used for treating oat crown rust and barley crown rust caused by *Puccinia coronata*.

This anti-fungal method may be particularly suited to inhibiting at least one of spore germination and hyphae formation.

In certain embodiments, the methods of the invention may be applicable for treating nematode associated conditions. Non-limiting examples of plant nematode diseases and their instigators include: Bulb and stem nematode (*Ditylenchus dipsaci*); Chrysanthemum foliar nematode (*Aphelenchoides ritzemabosi*); Cyst nematode (*Heterodera trifolii*); Dagger nematode (*Xiphinema americanum*); Lesion nematode (*Pratylenchus* spp., *Pratylenchus neglectus*, *Pratylenchus penetrans*); Needle nematode (*Longidorus* spp.); Pin nematode (*Paratylenchus* spp., *Paratylenchus hamatus*); Reniform nematode (*Rotylenchulus* spp.); Root-knot nematode (*Meloidogyne* spp., *Meloidogyne arenaria*, *Meloidogyne chitwoodi*, *Meloidogyne hapla*, *Meloidogyne incognita*, *Meloidogyne javanica*); Spiral nematode (*Helicotylenchus* spp.); Stubby-root nematode (*Paratrichodorus* spp.); and Stunt nematode (*Tylenchorhynchus* spp.).

Still further, the methods and compositions of the invention may be used for treating pathologic conditions caused by viral pathogens. Non-limiting examples of plant viral diseases and their instigators include: Alfalfa enation (genus Rhabdovirus, Alfalfa enation virus (AEV)); Alfalfa mosaic (genus Alfamovirus, Alfalfa mosaic virus (AMV)); Bean leaf roll (genus Luteovirus, Bean leaf roll virus (BLRV)); Bean yellow mosaic (genus Potyvirus, Bean yellow mosaic virus (BYMV)); Cucumber mosaic (genus Cucumovirus, Cucumber mosaic virus (CMV)); Lucerne Australian latent (genus Nepovirus, Lucerne Australian latent virus (LALV)); Lucerne Australian symptomless (genus Comoviridae, Lucerne Australian symptomless virus (LASV)); Lucerne transient streak (genus Sobemovirus, Lucerne transient streak virus (LTSV)); Pea streak (genus Carlavirus, Pea streak virus (PSV)); Red clover vein mosaic (genus Carlavirus, Red clover vein mosaic virus (RCVMV)); Tobacco streak (genus Ilarvirus, Tobacco streak virus (TSV)); Tomato etch (Tobacco etch virus); and White clover mosaic (genus Potexvirus, White clover mosaic virus (WCMV)).

According to certain embodiments, the method of the invention protects plants from pathogen by conferring resistance in plants against pests infections or infestations. More specifically, the method of the invention comprises the step of applying onto a plant, to a plant material or in the vicinity of said plant or plant material a biocontrol agent or a composition comprising the same. In specific embodiments, the biocontrol agent of the invention comprises at least one of:

a. *Pseudozyma aphidis* cells or any isolate or mutant thereof;
b. *Pseudozyma aphidis* spores;
c. conditioned culture medium of *Pseudozyma aphidis*;
d. secreted compounds from *Pseudozyma aphidis*;
e. any extracts or preparations of any of (a) to (d); and
f. a combination of at least two of the biocontrol agents defined in (a) to (e).

According to various embodiments of the invention, the methods of the invention confer resistance in treated plants. The term "resistance" relates to the ability of plants to withstand bacterial, fungal, viral, insect or other pest infections or infestations, that is, said plants may demonstrate better survival rates during and after such infections or infestations as compared with non-treated plants, it may show lesser symptoms as compared with non-treated plants, or it may not be infected or infested in as high a rates as non-treated plants.

The concentration of the biocontrol agent to be used for the compositions and methods of the present invention varies depending on differences in objective crops, use method, preparation form, application amount, application time, kinds of harmful pathogens and the like, and cannot necessarily be defined.

In one embodiment, the method up-regulates or induces the expression of plant immune-related genes.

In a more specific embodiment, the plant immune-related genes encode at least one of pathogenesis-related proteins family and defensins family.

The pesticidal compositions of the invention are effective in the treatment, amelioration, prevention, elimination, delay of pathogens or confer resistance against pathogens which include but are not limited to viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal, fungal-like and viral pathogens for the major crops include: Soybeans: *Phytophthora megasperma* sp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium debaryanum*, Tomato spotted wilt virus, *Heterodera glycines Fusarium solani*; Canola: *Albugo candida*, *Alternaria brassicae*, *Leptosphaeria maculans*, *Rhizoctonia solani*, *Sclerotinia sclerotiorum*, *Mycosphaerella brassiccola*, *Pythium ultimum*, *Peronospora parasitica*, *Fusarium roseum*, *Alternaria alternata*; Alfalfa: *Clavibacter michiganensis* subsp. *insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium*, *Xanthomonas campestris* p.v. *alfalfae*, *Aphanomyces euteiches*, *Stemphylium herbarum*, *Stemphylium alfalfae*; Wheat: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondite* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea*, *Tilletia tritici*, *Tilletia laevis*, *Ustilago tritici*,

*Tilletia indica, Rhizoctonia solani, Pythium arrhenomanes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *carotovora, Cephalosporium acremonium, Phytophthora cryptogea, Albugo tragopogonis*; Corn: *Fusarium moniliforme* var. *subglutinans, Erwinia stewartii, Fusarium verticilloides, Fusarium moniliforme, Gibberella zeae (Fusarium graminearum), Stenocarpella maydis (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudomonas avenae, Erwinia chrysanthemi* pv. *zea, Erwinia carotovora*, Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Periconia circinate, Fusarium moniliforme, Alternaria alternate, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthora macrospora, Peronosclerospora sorghi, Peronosclerospora philippinensis, Sclerospora graminicola, Fusarium graminearum, Fusarium oxysporum, Pythium arrhenomanes, Pythium graminicola*; Rice *Magnaporthe grisea, Rhizoctonia solani*, etc.

It is also noted that the method of the invention is effective for preventing, ameliorating, inhibiting, eliminating or delaying the onset of pests infections or infestations in farm and industrial produce thereby extending the shelf-life or storage time of said produce.

In the fifth aspect, the invention is directed to a method for promoting growth in plant. The method of the invention comprises the step of applying onto a plant, to a plant material or in the vicinity of said plant or plant material a biocontrol agent or a composition comprising the same. In specific embodiments, the biocontrol agent of the invention comprises at least one of:

a. *Pseudozyma aphidis* cells or any isolate or mutant thereof;
b. *Pseudozyma aphidis* spores;
c. conditioned culture medium of *Pseudozyma aphidis;*
d. secreted compounds from *Pseudozyma aphidis;*
e. any extracts or preparations of any of (a) to (d); and
f. a combination of at least two of the biocontrol agents defined in (a) to (e).

In a particular embodiment, this method leads to an increase in at least one of: plant weight, plant height, number of plant leaves, root system, plant thickness and plant biomass.

It should be noted that all the method of the invention involves application into a plant or in the vicinity of the treated plant.

The method may suitably involve applying the composition of the invention to a growing medium, such as soil, peat, sand or water, in an area where said plant or plant material exist. For example, the composition may be applied to or mixed with a growing medium, such as soil, peat, sand or water, that is to have plants planted in it or may be applied to or mixed with a growing medium, such as soil, peat, sand or water, that has plants planted in it, especially when the plants are those that are vulnerable to the pests described herein.

The composition may, for example, be applied through irrigation, spraying, direct application into said growing medium prior to planting said plants and impregnating towels, wipes, tissues an the like with said composition prior to their use in contact with the plant or plant material to be protected In the sixth aspect, the invention provides the use of a biocontrol agent in the manufacture of a pesticidal composition for preventing, ameliorating, inhibiting, eliminating or delaying the onset of pests infections or infestations. The biocontrol agent of the invention may comprise at least one of:

a. *Pseudozyma aphidis* cells or any isolate or mutant thereof;
b. *Pseudozyma aphidis* spores;
c. conditioned culture medium of *Pseudozyma aphidis;*
d. secreted compounds from *Pseudozyma aphidis;*
e. any extracts or preparations of any of (a) to (d); and
f. a combination of at least two of the biocontrol agents defined in (a) to (e).

In some embodiments, the biocontrol agent of the invention may be used for preparing pesticidal compositions, specifically, bactericidal compositions, for treating, preventing, ameliorating, inhibiting, eliminating or delaying the onset of bacterial infections or infestations.

These bacterial infections may be caused by at least one of: *Clavibacter michiganensis, Agrobacterium tumefaciens, Erwinia amylovora, Pseudomonas syringae* pv. *lachrymans, Pseudomonas syringae* pv. tomato, *Streptomyces scabies, Xanthomonas campestris* pv. *campestris* and *Xanthomonas capestris* pv. *vesicatoria.*

In yet another embodiment, the use of the biocontrol agent provided by the invention, results in a fungicidal composition for treating, preventing, ameliorating, inhibiting, eliminating or delaying the onset of fungal infections or infestations.

This fungicidal composition may be particularly suited for treating fungal infections caused by at least one of: *Botrytis cinerea, Penicillium digitatum, Alternaria brassicicola, Uromyces appendiculatus, Leveillula taurica, Sclerotinia sclerotiorum* and *Puccinia coronate.*

More than simply acting versus plant pathogens, the pesticidal composition produced using the biocontrol agent confers resistance in plants against pests infections or infestations.

The invention further provides the use of the biocontrol agent of the invention in the preparation of any pesticidal composition for example, an antiviral composition, an antinematode composition or any composition that may be used for treating insects associated pathologic conditions.

In one embodiment, the pesticidal composition produced using the biocontrol agent up-regulates or induces the expression of plant immune-related genes. In more specific embodiments, said plant immune-related genes encode at least one of pathogenesis-related proteins family and defensins family.

In more specific embodiments, the plant immune-related genes encode at least one of pathogenesis-related proteins family and defensins family.

In a specific embodiment, the member of the pathogenesis-related proteins family may be PR1 and the member of the defensins family may be PDF1.2.

In another specific embodiment, the pesticidal composition induces the expression of PR1 in said plant.

In yet another specific embodiment, the pesticidal composition induces the expression of PDF1.2 in said plant.

In a further specific embodiment, the pesticidal composition induces the expression of PR1 and PDF1.2 in said plant, optionally said composition induces the expression of at least one additional immune-related gene.

Furthermore, this composition is also suited for preventing, ameliorating, inhibiting, eliminating or delaying the onset of pests infections or infestations in farm and industrial produce thereby extending the shelf-life or storage time of said produce.

In addition, in some embodiments the use according to the invention is for preparing a composition for promoting growth in plants.

Still further, the invention provides a biocontrol agent as defined by the invention, for use in the treatment, prevention, amelioration, inhibition, elimination or delaying the onset of pests infections or infestations. Specifically, in the treatment, prevention, amelioration, inhibition, elimination or delaying the onset of bacterial, fungal or viral, infections or infestations.

In some embodiments, the invention provides a biocontrol agent as defined by the invention, for use in conferring resistance in plants against pests infections or infestations.

In other embodiments, the invention provides a biocontrol agent as defined by the invention, for use in preventing, ameliorating, inhibiting, eliminating or delaying the onset of pests infections or infestations in farm and industrial produce thereby extending the shelf-life or storage time of said produce.

Still further, the invention provides a biocontrol agent as defined by the invention, for use in promoting growth in plant.

A further aspect of the invention relates to a composition for use in treating, preventing, ameliorating, inhibiting, eliminating or delaying the onset of bacterial, fungal or pest infestation in a plant or a plant material.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley; Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998). "Nucleic Acid Hybridization" Hames, B. D., and Higgins S. J., eds. (1985); "Transcription and Translation" Hames, B. D., and Higgins S. J., Eds. (1984); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials
    Potato dextrose agar (Difco)
    Potato dextrose broth (Difco)
    Nutrient agar medium (Difco)
Equipment and Kits
    EZ Fungal DNA extraction kit (Eisenberg Bros. Ltd., Israel)
    Qiangen RNeasy kit (Invitrogen, San Diego, Calif.)
    EZ-First strand cDNA synthesis kit (Biological industries, Israel)
    Multigen fermentor (New Brunswick)
    Biolog SF-N plates (Biolog, Hayward, Calif., U.S.A)
    Sep-Pak C18 cartridges (Waters)
    Rotor evaporator (Buchi, Flawil, Switzerland)
    E5150 Sputter Coater (Polaron Equipment Ltd., War-ford Hertfordshire WD1, UK)
    Scanning electron microscope (JSM-5410LV; JEOL Ltd, Tokyo, Japan)
Experimental Procedures
P. aphidis Culture
    P. aphidis isolate L12 was maintained in solid culture on potato dextrose agar (PDA) at 26° C. and transferred to fresh medium monthly. Liquid cultures were maintained in potato dextrose broth (PDB) for 7-10 days at 26° C. on a rotary shaker set at 150 rpm. After 10 days in liquid culture, $10^8$ conidia/ml were obtained.

DNA Extraction

Cells were cultured in PDB on a rotary shaker (150 rpm) at 26° C. The fungal biomass was centrifuged at 10,000 rpm for 20 min, and the culture medium was discarded. Fungal cells were washed twice with sterile distilled water and centrifuged for an additional 20 min at 10,000 rpm. The water was discarded, and the fungal biomass was transferred to sterile 1.5-ml Eppendorf microtubes and lyophilized. Genomic DNA was prepared from lyophilized 10 mg of fungal material using EZ Fungal DNA extraction kit according to the manufacturer's directions.

DNA Sequence

Figure 2:
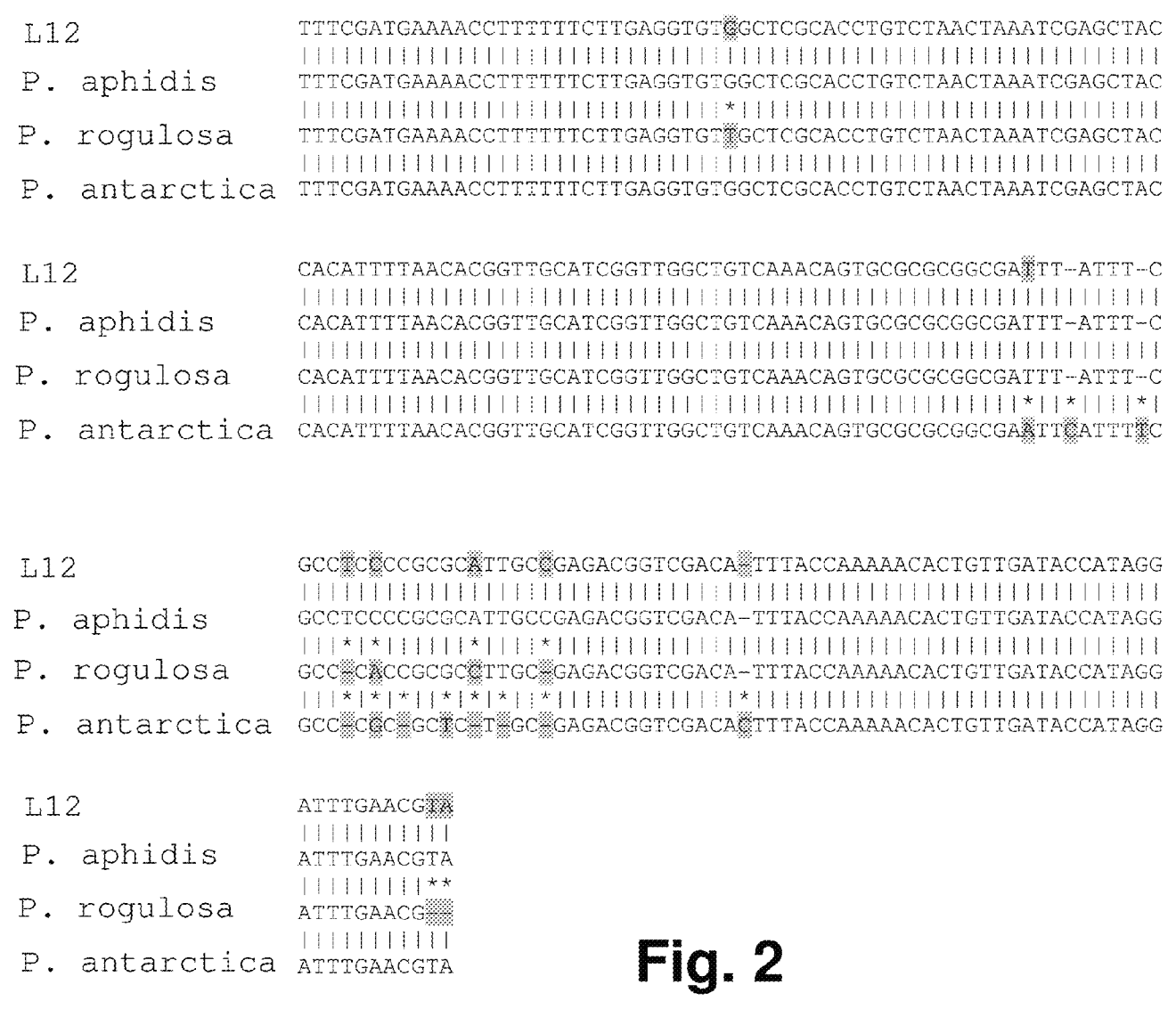

Extracted DNA was used for PCR with specific primers for entire ITS (ITS1f 5'-CTTGGTCATTTAGAGGAAGTAA-3' (also denoted by SEQ ID NO. 5) and ITS4r 5'-TCCTCCGCT-TATTGATATGC-3', (also denoted by SEQ ID NO. 6). PCR reactions were carried out by the Readymix Taq DNA polymerase system (Sigma) in volumes of 25 μl and 1 μl of the template DNA. Amplifications were performed in a thermal cycler (BioRad Inc., Hercules, Calif.) programmed for an initial denaturation step at 95° C. for 3 min, 35 cycles at 92° C. for 30 s, 58 (ITS) or 52° C. (nSSU) for 30 s, and 72° C. for 1 min. The amplifications were completed with a 10-min final extension at 72° C. The amplified bands were sent to sequencing and sequences were aligned with databases. The sequences are presented in FIG. 2 and denoted as SEQ ID NO.: 7, 8, 9 AND 10, corresponding to L12, *P. aphidis*, *P. rogulosa* and *P. Antarctica*, respectively.

RNA Isolation and RT-PCR Analysis

Total RNA was isolated from untreated tomato or *Arabidopsis* plants and from plants 10 days post-treatment with $10^8$ *P. aphidis* spores/ml with Qiangen RNeasy kit according to the manufacturer's instructions. DNase treatment was done on RNeasy Qiagen columns, according to manufacture instructions (Invitrogen, San Diego, Calif.). 1 μg of total RNA was reverse-transcribed with EZ-First strand cDNA synthesis kit. RT-PCR was performed using the thermal cycling program as follows: 96° C. for 2 min.; 27-33 cycles of 95° C. for 15 sec., 55° C. for 20 sec and 72° C. for 30 sec. Primers were as follows: LePR1F-5' TCTTGTGAGGCCCAAAATTC 3' (denoted as SEQ ID NO.: 1); LePR1R-5' ATAGTCTGGC-CTCTCGGACA 3' (denoted as SEQ ID NO.: 2); LeActineF-5' AGGCACACAGGTGTTATGGT 3' (denoted as SEQ ID NO.: 3) and LeActineR-5' AGCAACTCGAAGCTCATTGT 3' (denoted as SEQ ID NO.: 4), LePIN1F-5' CTT CTTC-CAACTTCCTTT G 3' (denoted as SEQ ID NO.: 11); and LePIN1R-5' TGTTTTCCTTCGCACATC 3' (denoted as SEQ ID NO.: 12); AtPR1F-5' GCCCACAAGAT-TATCTAAGGG 3' (denoted as SEQ ID NO.: 13); and AtPR1R-5' ACCTCCTGCATATGATGCTCCT 3' (denoted as SEQ ID NO.: 14); AtPDF1.2F-TCATG-GCTAAGTTTGCTTCC (denoted as SEQ ID NO.: 15); and PDF1.2R-5' AATACACACGATTTAGCACC 3' (denoted as SEQ ID NO.: 16).

Isolation of *P. aphidis*-Secreted Fraction for Inhibition Assays In Vitro

*P. aphidis* was placed on PDA covered with dialysis tubing and incubated at 26° C. for 10 days. The tubing containing the fungi was then removed and the plates with the *P. aphidis*-secreted fraction were used for inhibition assays with different fungal pathogens. The plates were inoculated with the different pathogens, incubated at their optimum temperature and their spore germination and hyphal linear growth measured for several days. In addition, metabolites were extracted from PDB culture filtrate using ethyl acetate and hexane. More specifically, *P. aphidis* was grown in PDB medium at 26° C. for 10 days in Erlenmeyer flasks at a constant agitation of 150 rpm. The fungal cells were spun down (20 min at 10,000 rpm). The supernatant, consisting of culture filtrate, was titrated to pH 2.0 using 1 N HCl and extracted with an equivalent volume of ethyl-acetate using separating funnels. The ethyl-acetate fraction was collected and evaporated in a rotor evaporator at 42° C. [Paz, Z., et al., (2007) J. Appl. Microbiol. 103(6):2570-2579]. Where hexane was used, the collected ethyl-acetate fraction was re-extracted with hexane and evaporated in a rotor evaporator at 42° C. as indicated above. The dry fraction was reconstituted in methanol and used for in vitro experiments after application on Whatman paper discs (6 mm diameter). The discs were placed in the center of the PDA plates inoculated with the different bacteria.

Propagation of Plants and Pathogens

*Botrytis cinerea* (B05.10), *Penicillium digitatum*, *Alternaria brassicicola*, and *Sclerotinia sclerotiorum* were grown on PDA medium at 22-27° C. under 12-h daily illumination. *Leveillula taurica* was maintained on pepper plants at 25° C. *Puccinia graminis* and *Uromyces appendiculatus* were maintained on wheat and beans plants, respectively, at 25° C.

*Clavibacter michiganensis* subsp. *michiganensis* (CMM44), *Xanthomonas campestris* pv. *vesicatoria*, *X. campestris* pv. *campestris*, *Agrobacterium tumefaciens*, *Erwinia amylovora*, *Pseudomonas syringae* pv. tomato, *P. syringae* pv. *lachrymans* and *Streptomyces scabies* were grown on nutrient agar medium (NA) in complete darkness at 28-37° C. All pathogens are from local collections.

Tomato plants (*Lycopersicon esculentum*, ecotype 870) were grown at 25° C. and 40% relative humidity in the greenhouse.

Inhibition of *B. cinerea* on Tomato Plants

To examine inhibition of *B. cinerea* on detached leaves and on whole plants, tomato leaves/plants were sprayed with different concentrations ($10^4$ and $10^8$ spores/ml) of *P. aphidis* to flowing, and were allowed to establish for 3 days on the leaves/plants. The plants were then inoculated with the pathogen (a total of 15,000 spores) and disease symptoms in treated plants and control plants treated with water were monitored.

Inhibition of *C. michiganensis* on Tomato Plants

Tomato plants were sprayed with different concentrations ($10^4$ and $10^8$ spores/ml) of *P. aphidis*. The *P. aphidis* was allowed to establish for 2-3 days on the plants, after which they were inoculated with *C. michiganensis* by cutting the first leaf with scissors dipped in bacterial suspension ($OD_{600}$~0.9). Disease symptoms in treated plants and in control plants sprayed with water were monitored. Some experiments involved additional applications of *P. aphidis* post-*C. michiganensis* inoculation as described in Example 6.

Inhibition of *Sphaerotheca fuliginea* on Cucumber Plants

Cucumber seedlings (*Cucumis sativus* cultivar 'Saphi') were sprayed with *P. aphidis* spores ($10^8$ spores/ml) or with water (ten seedlings for each treatment) three days before inoculation with *Sphaerotheca fuliginea*, and infection was scored 11, 12 and 16 days post-inoculation. For inoculation, spores from a donor plant carrying inoculum were blown directly onto healthy seedlings from four sides. Infection was scored by determination of percentage of leaves coverage with powdery mildew symptoms using scales of 1-5%, 5-25%, 25-50% and 50-100%.

Inhibition of Decay on Post-Harvested Grapes

Thompson seedless grapes from the vineyard of Yuval in Moshav Lachis harvested and packed in 1.25 kg from 3 clusters (32 replicates). One day after, the grapes were sprayed with water or *P. aphidis* ($10^6$ or $10^8$ spores/ml) and transferred into storage at 0° C. 2.5 months later, the grapes were transferred to 20° C. for three days and decay were monitored. The amount of decayed grapes (in grams) was determined for each replicate. Due to sample variability, the results of two consecutive replicates were pooled together to give a sample size of 2.5 kg. Average decay was determined and significance was calculated using Instat with Student-Newman Keuls posthoc test at P value of 0.01.

Electron Microscopy

To preserve and examine fungal spores and hyphae on *Arabidopsis* leaves, a vapor fixation procedure was employed in this study as described in Kim, (2007) [Kim, K. W. (2007), J. Phytopathology 156:125-128] with minor changes. *Arabidopsis* leaves were attached in a well-ventilated fume hood to a vial lead four days after treatment with *P. aphidis*. The specimens were exposed in a closed vial to the vapor of 2% (w/v) osmium tetroxide for at least 2 h and then remained in the fume hood overnight. Squares (each 5×5 $mm^2$) of osmicated leaves were then excised using a razor blade and mounted on a metal stub (10 mm in diameter). They were sputter-coated with gold (approximately 30 nm thick) using an E5150 Sputter Coater and examined with a scanning electron microscope at an accelerating voltage of 20 kV.

Assay of Biological Activity of Emitted Volatiles

*P. aphidis* was grown on PDA in one-half of a commercially-produced compartmentalized petri dish for 10 days at 25° C. prior to the addition of mycelial plug of *B. cinerea* at the other half of the compartmentalized petri dish. Colony diameters of *B. cinerea* were recorded up to 4 days post-inoculation and compared with growth on a control plates in the absence of *P. aphidis*.

Cellulose Activity

*P. aphidis* was grown on tap water agar plates (8%) covered with autoclaved cellulose membrane. Cell number was recorded seven days post-inoculation.

*P. aphidis* exposure to UV

PDA plates were inoculated with $10^8$ *P. aphidis* cells and were subjected to UV exposure for different periods (0, 10, 20 and 30 min). Plates were then transferred into incubator at 25° C. and were recorded after 72 h with digital camera.

Example 1

Isolation of *P. aphidis*

The inventors isolated a strain of *P. aphidis* (isolate L12) from strawberry leaves. The L12 isolate was associated with the collapse of powdery mildew colonies seen on FIG. 1A. The L12 isolate was identified as *P. aphidis* using specific primers for the entire rDNA region of the internal transcribed spacer (ITS1) and for the partial sequence of the mitochondrial large subunit (mtLSU) and nuclear small subunit (nSSU) as described in the Experimental procedures above [Avis, T. J., et al. (2001) Phytopathology 91(3):249-254]. Sequences showed 100% identity to *P. aphidis*, as shown in Table 1 and FIG. 2.

TABLE 1

*P. aphidis* sequences identification

|  | % of similarity to *P. aphidis* |
|---|---|
| ITS[a,b] | 100 |
| nSSU[b] | 100 |
| mtLSU[a,b] | 100 |

[a] performed by Boekhout Teun,
[b] performed by Levy Maggie as Described in Avis et al., 2001

Example 2

*P. aphidis* is an Epiphytic Yeast-Like Fungus

The inventors further characterize the L12 isolate. Scanning electron microscopy shown in FIG. 3) revealed that *P. aphidis* L12 isolate is a dimorphic epiphytic fungus. The fungus can have a yeast-like form (FIG. 3E) and synemata-like structure (FIG. 3C) on PDA and also can form hyphae (FIG. 3D). The isolated fungus can grow and cover tomato and *Arabidopsis* leaves surface, as shown in FIGS. 3F, 3I and 3J. Sectioning leaves inoculated with *p. aphidis* did not reveal any fungal structures within the tissue. The inventors concluded that, under the specific experimental conditions used, *P. aphidis* is only found as an epiphyte; however, it cannot be excluded as an endophyte since *P. aphidis* was identified on leaves surface following the sterilization of said surface using 1% sodium hypochlorite and even using naked flame. Furthermore, as FIG. 4 clearly shows, *P. aphidis* survived up to 30 minutes of UV exposure, and therefore, it cannot be excluded that the fungus identified on hypochlorite- and flame-sterilized leaf surfaces withstood these harsh procedures.

Example 3

Optimal Temperature for *P. aphidis* L12 Isolate Growth

A common medium potato dextrose agar (PDA) was used to study the growth of *P. aphidis* at various temperatures. A 25 to 28° C. range was determined as the optimal temperature range for colony linear growth (shown in FIGS. 5A and 5C) and fungal secretions (shown in FIGS. 5B and 5C).

Example 4

*P. aphidis* Secrete Cellulase

Figure 6:
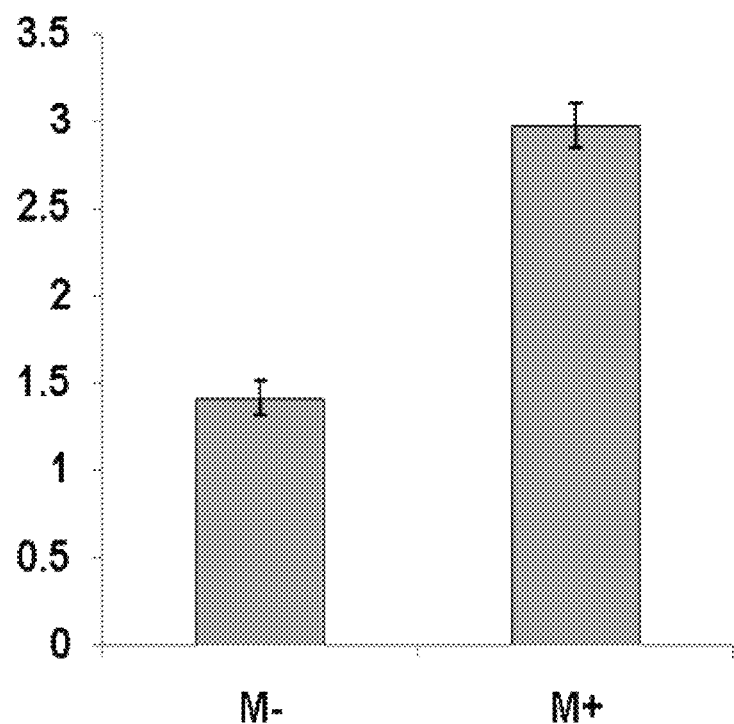

In order to verify that *P. aphidis* secretes cellulase, the inventors incubated the fungus on water agar plates supplemented with cellulose membrane. As FIG. 6 demonstrates, *P. aphidis* grew better on cellulose-supplemented plates, suggesting it secretes cellulase.

Example 5

*P. aphidis* Colonization, Proliferation and Maintenance on Tomato Plants

The inventors examined the ability of *P. aphidis* to colonize and proliferate on tomato plants. *P. aphidis* spores were sprayed on the plants and their population dynamics determined. The leaves were visualized under a light microscope to verify the presence of *P. aphidis* spores, and leaf samples were applied to PDA plates to verify viability. *P. aphidis* was observed on the leaves below and above the spraying point and also on newly emerging leaves. *P. aphidis* was found on all of the leaves up to 21 days post-application.

Example 6

Pathogenicity of *P. aphidis*

Foliar application of *P. aphidis* at two different concentrations ($10^4$ and $10^8$ spores/ml) on tomato and *Arabidopsis* plants and detached leaves showed no evidence of pathogenicity or symptoms of plant sensitivity up to 4 weeks post-application. Similarly, there was no evidence of pathology associated with tomato plants after drenching the root system with the biocontrol agent suspension (for example chlorosis or any other symptoms, data not shown).

Example 7

In Vitro Impact of *P. aphidis* Secretions on Plants Pathogens

Impact of *P. aphidis* Secretions on Fungal Pathogens

Figures 1A, 1B:
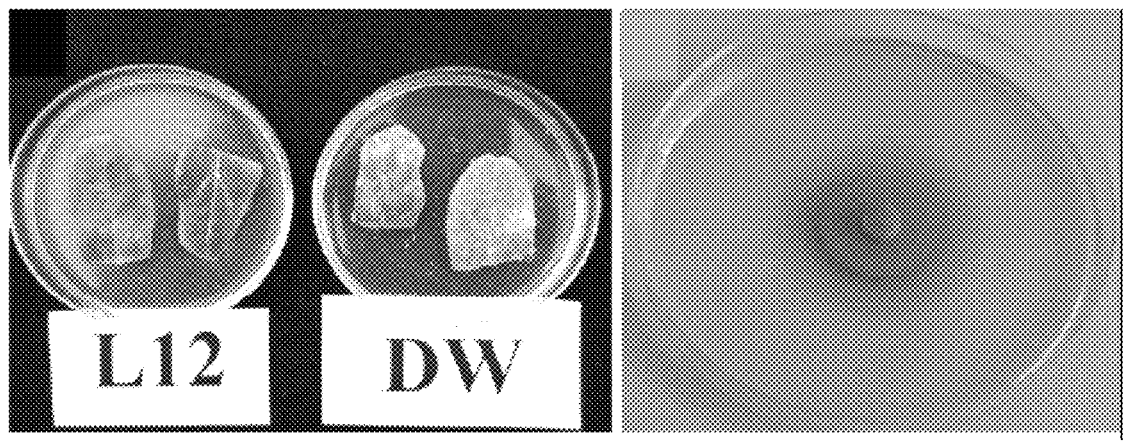
FIG. 1A-1B
Isolation of *Pseudozyma aphidis* L12
Figures 3A, 3B:
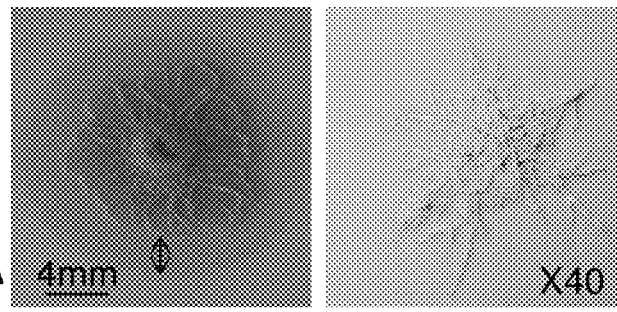
FIG. 3A-3J
*P. aphidis* Growth on PDA Plate and on Plants
Figures 3C, 3D:
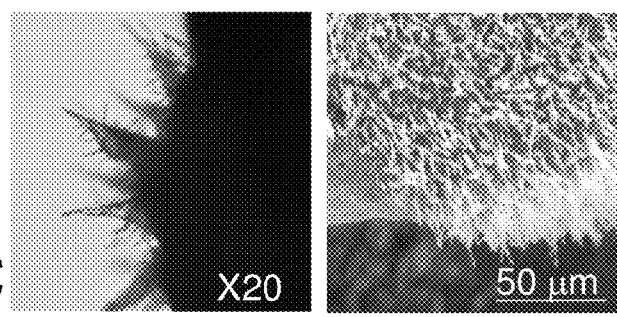
Figures 3E, 3F:
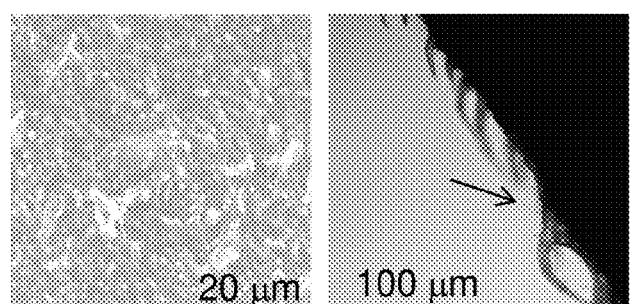
Figures 3G, 3H:
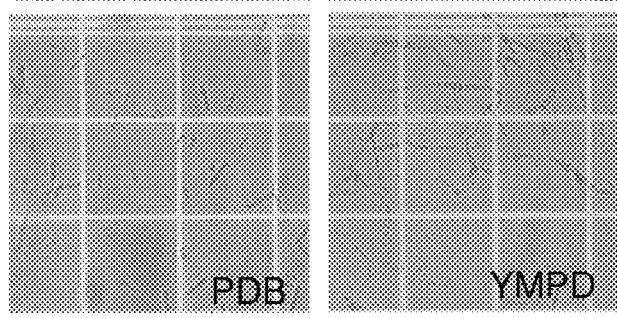
Figures 3I, 3J:
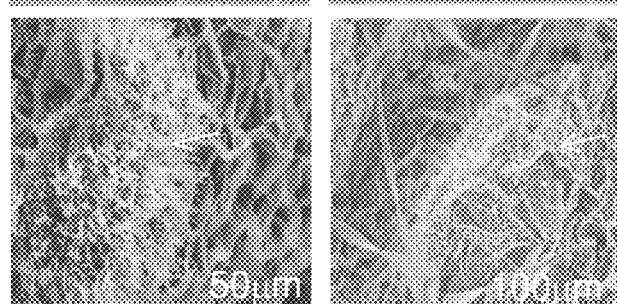
Figure 4:
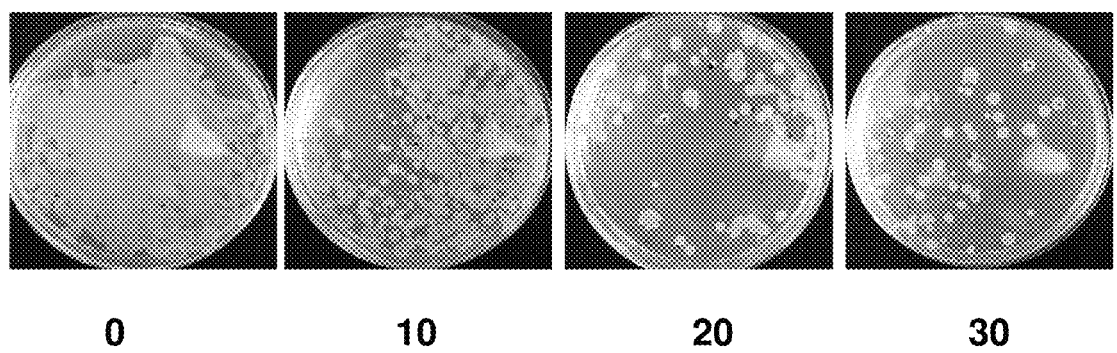
FIG. 4

Shown in FIG. 1B and FIG. 3A, the *P. aphidis* L12 isolate secretes extracellular, pinkish-colored metabolites. Those secretions were found to inhibit spore germination of several fungal pathogens in vitro, as demonstrated in FIG. 7A. They completely inhibited spore germination of the gray mold-causing agent *Botrytis cinerea*, of *Puccinia graminis* which causes stem rust of small cereal grains (wheat, barley, oat, and rye) and of *Penicillium digitatum* causing green mold in citrus. *Alternaria brassicicola*, which causes *Brassica* dark leaf spot on most *Brassica* species, was inhibited by 85 to 90%, *Uromyces appendiculatus*, the casual agent of bean rust, was inhibited by 70% and *Leveillula taurica*, which causes powdery mildew on tomatoes and pepper, was inhibited by 45%. The secretions also completely inhibited sclerotial germination of *Sclerotinia sclerotiorum*, whereas they only slightly inhibited (10%) spore germination in *Puccinia coronata*, the causal agent of oat crown rust and barley crown rust, shown in FIG. 7A.

Figure 8:
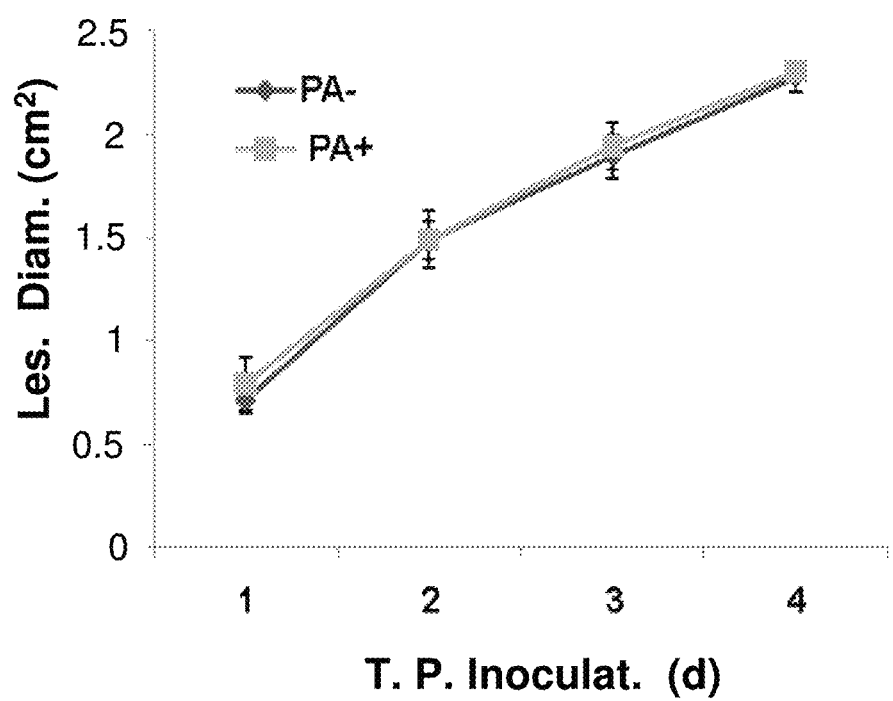

The inhibition of *Sclerotinia sclerotiorum* sclerotia germination and mycelium linear growth of *B. cinerea*, *A. brassicicola* and *S. sclerotiorum* persisted even when autoclaved *P. aphidis* secretions were used (data not shown). In a further assay, the inventors used divided petri-dishes with *P. aphidis* limited to one side of said plates, and either *B. cinerea*, *A. Brassicicola* or *S. sclerotiorum* on the other. As depicted in FIG. 8, no pathogen inhibition was detected under these conditions, suggesting that the secretions responsible for pathogen inhibition are not volatile.

Impact of *P. aphidis* Secretions on Bacterial Pathogens

The growth-inhibitory effect of *P. aphidis* extracts on various bacteria was determined by measuring haloes of decay around filters saturated with ethyl-acetate or hexane extracts of *P. aphidis* L12 isolate culture-filtrate metabolites (as demonstrated by FIG. 7B). The inventors found inhibition of several bacterial pathogens in vitro using ethyl-acetate extract, as illustrated by FIG. 7B. The most significant inhibition was of *Clavibacter michiganensis* subsp. *michiganensis* (26 mm), which causes bacterial canker of tomato plants (*Lycopersicon esculentum*), and of *Agrobacterium tumefaciens* (25 mm), which causes crown gall disease. Other bacterial pathogens *Erwinia amylovora*, *Pseudomonas syringae* pv. *lachrymans*, *Pseudomonas syringae* pv. tomato, *Streptomyces scabies*, *Xanthomonas campestris* pv. *campestris* and *Xanthomonas capestris* pv. *vesicatoria*-displayed moderate inhibition (7-15 mm).

The inhibition of several bacterial and fungal pathogens using hexane extract is shown in FIG. 7C. In the case of hexane, the most significant inhibition was also of *C. michiganensis* subsp. *michiganensis* (24 mm), and of *X. capestris* pv. *vesicatoria* (15 mm). Other bacterial pathogens such as *A. tumefaciens*, *E. amylovora*, *P. syringae* pv. Tomato and *X. campestris* pv. *Campestris* showed moderate inhibition (9-12 mm). Furthermore, hexane extracts inhibited the analyzed fungi *B. cinerea* (13 mm) and *A. brassicicola* (19 mm).

Example 8

Impact of *P. aphidis* on Fungal Infection on Detached Leaves and in Planta

Detached tomato leaves were sprayed with *P. aphidis* ($10^4$ or $10^8$ spores/ml) three days pre-inoculation with *B. cinerea* (1600 or 16,000 spores in total). FIGS. 9A and 9B show that infection was significantly reduced by 55 to 70% and by almost 100% when detached leaves were sprayed with $10^4$ or $10^8$ spores/ml of *P. aphidis*, respectively, as compared to leaves sprayed with water. Application of *P. aphidis* on detached leaves infected with *B. cinerea* stopped the infection's spread (FIG. 9E).

As shown in FIG. 9C, application of $10^4$ *P. aphidis* spores/ml or $10^8$ *P. aphidis* spores/ml to tomato plants in the greenhouse 3 days before inoculation with *B. cinerea* reduced infection by 15 to 50% and by 45 to 80%, respectively. Autoclaving of *P. aphidis* abolished the inhibitory effects on *B. cinerea* infection, as illustrated in FIG. 9D.

FIG. 9F shows the effect of *P. aphidis* spores powdery mildew in cucumber seedlings. Application of $10^8$ *P. aphidis* spores/ml to cucumber seedlings in the greenhouse 3 days before inoculation with a powdery mildew causing fungi *Sphaerotheca fuliginea* reduced infection by 77 to 97%.

Example 9

Biocontrol Activity of *C. michiganensis* by *P. aphidis* in Planta

Application of $10^8$ *P. aphidis* spores/ml to tomato plants in the greenhouse three days prior to inoculation with *C. michiganensis* was 27 to 53% effective at preventing *C. michiganensis* symptoms (FIG. 10A), thus, demonstrating a protecting potential of the biocontrol agent of the invention. When the inventors added three more applications, given once a week, post-*C. michiganensis* infection, a 70 to 80% symptom reduction was obtained. As illustrated by FIG. 10B, the inventors also observed 50% recovery of plants after showing first symptoms. It appears that this is the first report on recovering ability of biological control agent on infected plants. The mechanisms by which plants can recover are still unknown. Without being bound by theory, the inventors speculate that there is a correlation between recovery and induced resistance. To evaluate this hypothesis, a time course analysis of PR gene induction is conducted before, during and after the recovery.

Example 10

Biocontrol Activity of *P. aphidis* on Post-Harvested Grapes Decay

Thompson seedless grapes were treated with water (control) or with *P. aphidis* ($10^6$ or $10^8$ spores/ml) one day after harvest and transferred into 0° C. environment for 2.5 months of storage. Three days after grapes were out of storage and kept in 20° C., grapes treated with *P. aphidis* displayed 50% less decayed berries. The findings are presented in Table 2 below.

TABLE 2

Decay on post-harvested grapes

| Treatment | Decay (%) | SE | SNK |
|---|---|---|---|
| PA $10^8$ | 10.8 | 1.2 | b |
| PA $10^6$ | 10.0 | 2.2 | b |
| Control | 19.2 | 1.0 | a |

Abbreviations: SNK (Student-Newman Keuls posthoc test, P = 0.01); SE (standard error; PA, *P. aphidis*)

Example 11

*P. aphidis* Induces Plant Growth

*P. aphidis* was found to promote growth of tomato plants. Tomato plants that were treated with a total of three applications (once a week) with *P. aphidis* were 20% taller, weighed 30% more and had 25% more leaves than untreated plants (see FIGS. 11A-11C, respectively). Treated plants were also more wooden (upright) and had a larger root system (data not shown). Without being bound by theory, the inventors speculate that *P. aphidis* application enhances photosynthesis by reducing water transpiration.

Example 12

*P. aphidis* Promotes Induced-Immune Genes Expression

Treatment with *P. aphidis* not only enhanced plant growth, but also induced the plant immune system. Shown in FIG. 12A, induction of PR1 gene expression was observed in tomato plants 6 and 10 days after foliar application of *P. aphidis*, while in plants treated with water, no induction was exhibited. PR1 and PDF1.2 expression was also upregulated in *Arabidopsis thaliana* plants after application of *P. aphidis* (FIG. 12B). When *Arabidopsis* mutants impaired in JA signaling jar1 and in SA accumulation and signaling NahG and npr1-1, respectively, were treated with *P. aphidis* followed by inoculation with *B. cinerea*, the inhibition persisted similarly to WT plants, as shown in FIGS. 13A, 13B and 13C. Thus, it appears that the induced resistance is SA-, JA- and NPR1-independent. The inventors now determine whether the extracted metabolites can either induce resistance or control infection of *B. cinerea* in-planta.

Example 13

Characterization of the Conditions Needed for *P. aphidis* Mass Production

The inventors first calibrate a method for obtaining sufficient active inocula for laboratory and field experiments. *P. aphidis* isolate L12 is grown in different liquid growth media at various temperatures and spore concentration and activity is monitored in a bioassay against *B. cinerea*. In preliminary experiments, the inventors used the common medium potato dextrose agar (PDA) at various temperatures and established 25 to 28° C. as the optimal temperature range for colony diameter and secretion, as shown in FIGS. 5A-5C. When the inventors grew the fungi in liquid potato dextrose broth (PDB) in Erlenmeyer flasks at a constant agitation of 150 rpm, $10^8$ conidia/ml were obtained after 10 days at 26° C. Next, different liquid media (e.g. yeast malt peptone dextrose, glucose-peptone medium, CZAPEX-DOX) are explored at various temperatures using a Multigen fermentor, in order to obtain the optimal conditions for mass production of spores and active secretion as determined in bioassays against *B. cinerea*. In parallel, utilization of different carbon source of *P. aphidis* on Biolog SF-N plates is examined. The plates are also used for activity bioassay by applying low melting agar inoculated with either *Agrobacterium tumefaciens* or *B. cinerea* spores and examining growth inhibition of *P. aphidis* secretion in each different carbon source. Based on those results, an attempt is made to establish optimal conditions and media for maximum sporulation and activity.

Example 14

Exploration of *P. aphidis*-Host Interactions

*P. aphidis* L12 was first isolated from the surface of strawberry leaves and designated as an epiphyte. The inventors now examine the required conditions for *P. aphidis* L12 establishment and spread on the plant's aerial parts and its root system. The time needed for the fungi to establish themselves on the host and their ability to spread to different parts of the plant is monitored using microscopy. Next, the inventors propose to verify the epiphytic designation of L12. Tomato leaves are sprayed with L12 and allowed to establish themselves on the plant. The location of the fungi on both sprayed and unsprayed plants parts and in cross sections after surface sterilization is monitored. In addition, the inventors construct a fluorescent L12 isolate expressing GFP as described for *P. flocculosa*. The inventors then monitor the establishment of L12-GFP using a fluorescence binocular. The inventors also use confocal microscopy to detect L12-GFP inside the plant tissue. This allows studying the establishment *P. aphidis* L12 on plants and determining whether it can also penetrate the plant and grow as an endophyte.

Example 15

Assaying Fractions Secreted by *P. aphidis* Against Various Fungal and Bacterial Plant Pathogens In Vitro In preliminary results, the inventors demonstrated that compounds secreted from *P. aphidis* isolate L12 can inhibit various fungal pathogens, as illustrated in FIG. 7A, and that an ethyl-acetate extracts of these compounds can inhibit several bacterial pathogens in a dose-responsive manner, as demonstrated in FIG. 7B. Hexane extracts also inhibited bacterial and fungal pathogens, as demonstrated by FIG. 7C.

Next, the biocontrol ability of the L12-secreted fraction against the fungal pathogen *B. cinerea* and the bacterial pathogen *Clavibacter michiganensis* are further explored, and the investigation is expanded to other pathogens. First, the inventors examine the capacity of the whole secreted fraction of L12 to inhibit pathogens in vitro. The inventors use the secreted fraction plated on PDA by growing the fungi on dialysis tubing covering a PDA plate for 10 days and then removing the tubing with the fungi. The inventors concentrate the secreted fraction from the PDB culture filtrate and examine the dose-responsive effect against the pathogens. More specifically, in order to obtain the secreted fraction, L12 are grown in 1 liter PDB for 10 days in the dark with constant agitation (150 rpm), and the culture is centrifuged to remove the fungi. The culture filtrate is transferred through solid-phase extraction cartridges and eluted with 1 ml methanol. The eluted 'culture filtrate' fraction is then used for in-vitro bioassay experiments, first with *B. cinerea* and *C. michiganensis*, and then with other pathogens (e.g. *Sclerotinia sclerotiorum, Oidium lycopersicum, Agrobacterium tumefaciens, Xanthomonas campestris* pv. *vesicatoria* and *X. campestris* pv. *campestris*). The eluted fraction is applied in different concentrations on 6-mm filter discs that is then dried in a laminar flow hood and used in inhibition bioassays against different pathogens on plates in comparison to filter discs with methanol only. Alternatively, the eluted fraction is applied (at different concentrations) to plates containing suitable media for bioassays with the different pathogens.

In addition, metabolites are extracted from the culture filtrate using ethyl acetate and hexane. The culture filtrate is titrated to pH 2.0 using 1 N HCl and extraction with 100 ml ethyl acetate is repeated three times using separating funnels. The ethyl-acetate/hexane fractions is collected and evaporated in a rotor evaporator at 42° C. [Paz, Z., et al., (2007) J. Appl. Microbiol. 103(6):2570-2579]. The remaining PDB culture filtrate is concentrated using Sep-Pak C18. Each of the dry fractions is reconstituted with 1 ml methanol and used for in-vitro experiments as described before: each fraction is applied separately in different concentrations on 6-mm filter discs that is dried in a laminar flow hood and then used in inhibition bioassays against different pathogens on plates in comparison to filter discs with methanol only. Alternatively, the fractions are applied (at different concentrations) to plates containing suitable media for bioassays with the different pathogens. To verify whether the active compound is heat-sensitive, the inventors repeat the experiments with culture filtrate that has been boiled prior to extraction. Next, the inventors identify the active fraction and subsequently the active compound/s.

Example 16

Assaying the Effects of *P. aphidis* Against Various Fungal and Bacterial Plant Pathogens In Vivo In preliminary experiments presented in FIGS. 9A and 9B, the inventors demonstrated L12 inhibition of *B. cinerea* on detached leaves and on whole plants. The inventors extend their in-vivo experiments to other pathogens (*S. sclerotiorum*, Powdery mildew, *X. campestris* pv. *vesicatoria* and *C. michiganensis*). Tomato plants are sprayed with different concentrations ($10^4$, $10^8$ and $10^{12}$ spores/ml) of L12, and the L12 isolate is allowed to establish itself on the plants. The plants are inoculated with the above pathogens and disease symptoms as compared to plants sprayed with water are monitored.

Example 17

Isolation and Identification of the Active Compound(s) from the Secreted Fraction As indicated in the presented results, *P. aphidis* L12 has significant potential as an efficient biological agent against a variety of plant pathogens. A characterization of the conditions is required for efficient spore production and metabolite secretion, and the identification of active compounds may assist in developing an efficient biocontrol agent against a broad range of pathogens.

To isolate and identify the active compound(s) from the secreted fraction, L12 is grown in PDB for 10 days in the dark with constant agitation (150 rpm). A crude extract of L12 is obtained as described above, and the dry fractions are reconstituted in 1:9 (v/v) methanol:water and subjected to chromatography. Reverse-phase liquid chromatography (RPLC) separation is performed on the crude extract according to [Paz, Z., et al., (2007) J. Appl. Microbiol. 103(6):2570-2579]. Each of the detected compounds is collected and bioassayed against *B. cinerea*. The active compound(s) are then identified using HPLC-MS and if necessary, NMR.

What is claimed is:

1. An agricultural pesticidal composition comprising:
(A) an agricultural biocontrol agent that comprises at least one of:
  (a) *Pseudozyma aphidis* cells or an isolate thereof;
  (b) *Pseudozyma aphidis* spores;
  (c) conditioned culture medium of *Pseudozyma aphidis*;
  (d) secretion(s) from *Pseudozyma aphidis*;
  (e) extract(s) of any of (a) to (d); or
  (f) a combination of at least two of the biocontrol agents defined in (a) to (e); and
(B) one or more carrier(s), diluent(s), and/or excipient(s);
wherein said agricultural biocontrol agent is present at a concentration effective in treating, preventing, inhibiting, eliminating or delaying the onset of pest infection or infestation in a plant or plant material to which, or in the vicinity of which, the agricultural pesticidal composition is applied.

2. The agricultural pesticidal composition according to claim 1, wherein said concentration is effective in treating, preventing, inhibiting, eliminating or delaying the onset of Oomycetes infection or infestation caused by at least one of: *Pythium* spp., *Pythium aphanidermatum*, *Pythium ultimum*, *Pythium debaryanum Pythium irregulare*, *Pythium splendens*, *Pythium arrhenomanes*, *Pythium graminicola*, *Phytophthora* spp., *Phytophthora medicaginis*, *Phytophthora megasperma* f.sp. *medicaginis*, Downy mildews, *Peronospora trifoliorum*, *Peronospora*, *Bremia*, *Peronosclerospora*, *Plasmopara* spp., *Pseudoperonospora* and *albugo* spp.

3. The agricultural pesticidal composition according to claim 1, wherein said concentration is effective in treating, preventing, inhibiting, eliminating or delaying the onset of insect infestation.

4. The agricultural pesticidal composition according to claim 1, wherein said concentration is effective in treating, preventing, inhibiting, eliminating or delaying the onset of viral infection or infestation.

5. The agricultural pesticidal composition according to claim 1, wherein said plant or plant material is farm or industrial produce, and said effective concentration extends shelf-life or storage time of said produce.

6. The agricultural pesticidal composition according to claim 1, wherein said plant or plant material is any one of seed(s), roots, bulbs, tubers, corms, leaves, flowers, stems, callus tissue, nuts, grains, fruit, cuttings, root stock, harvested crops, roots, bulbs, tubers, corms, leaves, flowers, seeds, stems, callus tissue, nuts, grains, fruit, cuttings, root stock or scions.

7. The agricultural pesticidal composition according to claim 6, wherein said plant or plant material is seed(s), and wherein said concentration is effective in treating, preventing, inhibiting, eliminating or delaying the onset of said infection or infestation, and wherein said infection or infestation is a fungal infection or infestation, a bacterial infection or infestation, or an Oomycetes infection or infestation, wherein said fungal infection or infestation is caused by at least one of: *Fusarium* spp., *Fusarium oxysporum*, *Botrytis cinerea*, *Penicillium digitatum*, *Alternaria brassicicola*, *Uromyces appendiculatus*, *Leveillula taurica*, *Sclerotinia sclerotiorum* and *Puccinia coronate*, said bacterial infection or infestation is caused by at least one of: *Clavibacter michiganensis*, *Agrobacterium tumefaciens*, *Erwinia amylovora*, *Pseudomonas syringae* pv. *lachrymans*, *Pseudomonas syringae* pv. tomato, *Streptomyces scabies*, *Xanthomonas campestris* pv. *campestris* and *Xanthomonas capestris* pv. *Vesicatoria* and said Oomycetes infection or infestation is caused by at least one of: *Pythium* spp., *Pythium aphanidermatum*, *Pythium ultimum*, *Pythium debaryanum Pythium irregulare*, *Pythium splendens*, *Pythium arrhenomanes*, *Pythium graminicola*, *Phytophthora* spp., *Phytophthora medicaginis*, *Phytophthora megasperma* f.sp. *medicaginis*, Downy mildews, *Peronospora trifoliorum*, *Peronospora*, *Bremia*, *Peronosclerospora*, *Plasmopara* spp., *Pseudoperonospora* and *albugo* spp.

8. The agricultural pesticidal composition according to claim 1, wherein said isolate of *Pseudozyma aphidis* is designated L12 isolate.

9. The agricultural pesticidal composition according to claim 1, wherein said concentration is effective for conferring resistance in plants against said infection or infestation.

10. The composition according to claim 9, wherein said concentration is effective for up-regulating or inducing the expression of plant immune-related genes, wherein said plant immune-related genes encode at least one of pathogenesis-related proteins family and defensins family.

11. An agricultural composition comprising:
(A) an agricultural biocontrol agent that comprises at least one of:
  (a) *Pseudozyma aphidis* cells or an isolate thereof;
  (b) *Pseudozyma aphidis* spores;
  (c) conditioned culture medium of *Pseudozyma aphidis*;

(d) secretion(s) from *Pseudozyma aphidis*;
(e) extract(s) of any of (a) to (d); or
(f) a combination of at least two of the biocontrol agents defined in (a) to (e); and (B) one or more carrier(s), diluent(s), and/or excipient(s); wherein said agricultural biocontrol agent is present at a concentration effective for promoting growth of said plant or plant material to which the agricultural composition is applied.

12. The composition according to claim 11, wherein said concentration is effective for inducing an increase in at least one of: plant weight, plant height, number of plant leaves, root system, plant thickness and plant biomass.

13. The composition according to claim 11, wherein said concentration is effective for reducing transpiration rate of said plant.

14. A method of treating, preventing, inhibiting, eliminating or delaying the onset of pest infection or infestation in a plant or a plant material, comprising the step of applying onto said plant or plant material, or in the vicinity of said plant or plant material, an agricultural pesticidal composition comprising:
   (A) an agricultural biocontrol agent that comprises at least one of:
      (a) *Pseudozyma aphidis* cells or an isolate thereof;
      (b) *Pseudozyma aphidis* spores;
      (c) conditioned culture medium of *Pseudozyma aphidis*;
      (d) secretion(s) from *Pseudozyma aphidis*;
      (e) extract(s) of any of (a) to (d); or
      (f) a combination of at least two of the biocontrol agents defined in (a) to (e); and
   (B) one or more carrier(s), diluent(s), and/or excipient(s); wherein said agricultural biocontrol agent is present at a concentration effective in treating, preventing, inhibiting, eliminating or delaying the onset of said pest infection or infestation in said plant or plant material to which, or in the vicinity of which, the agricultural pesticidal composition is applied.

15. The method according to claim 14, wherein said method is for treating, inhibiting, eliminating or delaying the onset of Oomycetes infection or infestation caused by at least one of: *Pythium* spp., *Pythium aphanidermatum*, *Pythium ultimum*, *Pythium debaryanum Pythium irregulare*, *Pythium splendens*, *Pythium arrhenomanes*, *Pythium graminicola*, *Phytophthora* spp., *Phytophthora medicaginis*, *Phytophthora megasperma* f.sp. *medicaginis*, Downy mildews, *Peronospora trifoliorum*, *Peronospora*, *Bremia*, *Peronosclerospora*, *Plasmopara* spp., *Pseudoperonospora* and *albugo* spp.

16. The method according to claim 14, wherein said method is for treating, inhibiting, eliminating or delaying the onset of insect infestation.

17. The method according to claim 14, wherein said method is for treating, inhibiting, eliminating or delaying the onset of viral infection or infestation.

18. The method according to claim 14, wherein said plant or plant material is farm or industrial produce, and said effective concentration extends shelf-life or storage time of said produce.

19. The method according to claim 14, wherein said plant or plant material is any one of seed(s), roots, bulbs, tubers, corms, leaves, flowers, stems, callus tissue, nuts, grains, fruit, cuttings, root stock, harvested crops, roots, bulbs, tubers, corms, leaves, flowers, seeds, stems, callus tissue, nuts, grains, fruit, cuttings, root stock or scions.

20. The method according to claim 19, wherein said plant or plant material is seed(s), and wherein said concentration is effective in treating, preventing, inhibiting, eliminating or delaying the onset of said infection or infestation, and wherein said infection or infestation is a fungal infection or infestation, a bacterial infection or infestation, or an Oomycetes infection or infestation, wherein said fungal infection or infestation is caused by at least one of: *Fusarium* spp., *Fusarium oxysporum*, *Botrytis cinerea*, *Penicillium digitatum*, *Alternaria brassicicola*, *Uromyces appendiculatus*, Leveillula *taurica*, *Sclerotinia sclerotiorum* and *Puccinia coronate*, said bacterial infection or infestation is caused by at least one of: *Clavibacter michiganensis*, *Agrobacterium tumefaciens*, *Erwinia amylovora*, *Pseudomonas syringae* pv. *lachrymans*, *Pseudomonas syringae* pv. tomato, *Streptomyces scabies*, *Xanthomonas campestris* pv. *campestris* and *Xanthomonas capestris* pv. *Vesicatoria* and said Oomycetes infection or infestation is caused by at least one of: *Pythium* spp., *Pythium aphanidermatum*, *Pythium ultimum*, *Pythium debaryanum Pythium irregulare*, *Pythium splendens*, *Pythium arrhenomanes*, *Pythium graminicola*, *Phytophthora* spp., *Phytophthora medicaginis*, *Phytophthora megasperma* f.sp. *medicaginis*, Downy mildews, *Peronospora trifoliorum*, *Peronospora*, *Bremia*, *Peronosclerospora*, *Plasmopara* spp., *Pseudoperonospora* and *albugo* spp.

21. The method according to claim 14, wherein said isolate of *Pseudozyma aphidis* is designated L12 isolate.

22. The method according to claim 14, wherein said concentration is effective for conferring resistance in plants against said infection or infestation.

23. The method according to claim 22, wherein said concentration is effective for up-regulating or inducing the expression of plant immune-related genes, wherein said plant immune-related genes encode at least one of pathogenesis-related proteins family and defensins family.

24. A method for promoting growth of a plant or a plant material, comprising the step of applying onto said plant or plant material or in the vicinity of said plant or plant material, an agricultural composition comprising:
   (A) an agricultural biocontrol agent that comprises at least one of:
      (a) *Pseudozyma aphidis* cells or an isolate thereof;
      (b) *Pseudozyma aphidis* spores;
      (c) conditioned culture medium of *Pseudozyma aphidis*;
      (d) secretion(s) from *Pseudozyma aphidis*;
      (e) extract(s) of any of (a) to (d); or
      (f) a combination of at least two of the biocontrol agents defined in (a) to (e); and
   (B) one or more carrier(s), diluent(s), and/or excipient(s); wherein said agricultural biocontrol agent is present at a concentration effective for promoting growth of said plant or plant material to which, or in the vicinity of which, the agricultural composition is applied.

25. The method according to claim 24, wherein said method leads to an increase in at least one of: plant weight, plant height, number of plant leaves, root system, plant thickness and plant biomass.

26. The method according to claim 24, wherein said concentration is effective for reducing transpiration rate of said plant.

27. An agricultural pesticidal composition comprising:
   (A) an agricultural biocontrol agent that comprises at least one of:
      (a) *Pseudozyma aphidis* isolate L12 cells;
      (b) spores of *Pseudozyma aphidis* isolate L12;
      (c) conditioned culture medium of *Pseudozyma aphidis* isolate L12;

(d) secretion(s) from *Pseudozyma aphidis* isolate L12;
(e) extracts of any of (a) to (d); or
(f) a combination of at least two of the biocontrol agents defined in (a) to (e) and (B) one or more carrier(s), diluent(s), and/or excipient(s);

wherein said agricultural biocontrol agent is present at a concentration effective in treating, preventing, inhibiting, eliminating or delaying the onset of pest infection or infestation in a plant or plant material to which, or in the vicinity of which, the agricultural pesticidal composition is applied.

28. The agricultural pesticidal composition according to claim 27, wherein said concentration is effective in treating, preventing, inhibiting, eliminating or delaying the onset of said infection or infestation, and wherein said infection or infestation is a fungal infection or infestation, a bacterial infection or infestation, or an Oomycetes infection or infestation, wherein said fungal infection or infestation is caused by at least one of: *Fusarium* spp., *Fusarium oxysporum, Botrytis cinerea, Penicillium digitatum, Alternaria brassicicola, Uromyces appendiculatus, Leveillula taurica, Sclerotinia sclerotiorum* and *Puccinia coronate*, said bacterial infection or infestation is caused by at least one of: *Clavibacter michiganensis, Agrobacterium tumefaciens, Erwinia amylovora, Pseudomonas syringae* pv. *lachrymans, Pseudomonas syringae* pv. tomato, *Streptomyces scabies, Xanthomonas campestris* pv. *campestris* and *Xanthomonas capestris* pv. *Vesicatoria* and said Oomycetes infection or infestation is caused by at least one of: *Pythium* spp., *Pythium aphanidermatum, Pythium ultimum, Pythium debaryanum Pythium irregulare, Pythium splendens, Pythium arrhenomanes, Pythium graminicola, Phytophthora* spp., *Phytophthora medicaginis, Phytophthora megasperma* f.sp. *medicaginis*, Downy mildews, *Peronospora trifoliorum, Peronospora, Bremia, Peronosclerospora, Plasmopara* spp., *Pseudoperonospora* and *albugo* spp.

29. A method of treating, preventing, inhibiting, eliminating or delaying the onset of bacterial or fungal infection or infestation in a plant or a plant material, comprising the step of applying onto said plant or plant material or in the vicinity of said plant or plant material the agricultural pesticidal composition according to claim 27.

* * * * *